US010415055B2

(12) United States Patent
Chen et al.

(10) Patent No.: US 10,415,055 B2
(45) Date of Patent: *Sep. 17, 2019

(54) ENHANCED EXPRESSION AND STABILITY REGIONS

(71) Applicant: Regeneron Pharmaceuticals, Inc., Tarrytown, NY (US)

(72) Inventors: Gang Chen, Yorktown Heights, NY (US); Robert Babb, River Edge, NJ (US); James P. Fandl, LaGrangeville, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/916,349

(22) Filed: Mar. 9, 2018

(65) Prior Publication Data

US 2018/0327777 A1 Nov. 15, 2018

Related U.S. Application Data

(60) Continuation of application No. 15/384,886, filed on Dec. 20, 2016, now Pat. No. 9,932,605, which is a continuation of application No. 14/967,689, filed on Dec. 14, 2015, now Pat. No. 9,562,238, which is a continuation of application No. 13/752,647, filed on Jan. 29, 2013, now Pat. No. 9,222,106, which is a division of application No. 12/793,898, filed on Jun. 4, 2010, now Pat. No. 8,389,239, which is a continuation of application No. 12/132,846, filed on Jun. 4, 2008, now Pat. No. 7,771,997.

(60) Provisional application No. 60/933,213, filed on Jun. 4, 2007.

(51) Int. Cl.

| | |
|---|---|
| ***C12N 15/85*** | (2006.01) |
| ***C12N 15/86*** | (2006.01) |
| ***C07K 16/00*** | (2006.01) |
| ***C12P 21/02*** | (2006.01) |

(52) U.S. Cl.

CPC .............. *C12N 15/85* (2013.01); *C07K 16/00* (2013.01); *C12N 15/86* (2013.01); *C07K 2319/30* (2013.01); *C12N 2740/10043* (2013.01); *C12N 2800/30* (2013.01); *C12N 2840/203* (2013.01); *C12P 21/02* (2013.01)

(58) Field of Classification Search

None

See application file for complete search history.

(56) References Cited

U.S. PATENT DOCUMENTS

| | | | |
|---|---|---|---|
| 6,689,606 | B2 | 2/2004 | Antoniou et al. |
| 7,771,997 | B2 | 8/2010 | Chen et al. |
| 8,389,239 | B2 | 3/2013 | Chen et al. |
| 9,222,106 | B2 | 12/2015 | Chen et al. |
| 9,562,238 | B2 | 2/2017 | Chen et al. |
| 2016/0097059 | A1 | 4/2016 | Chen et al. |
| 2017/0096681 | A1 | 4/2017 | Chen et al. |

FOREIGN PATENT DOCUMENTS

| | | |
|---|---|---|
| CA | 2 671 825 | 8/2008 |
| EP | 2 121 917 B1 | 11/2009 |
| WO | 02/081632 A2 | 10/2002 |

OTHER PUBLICATIONS

Aldrich T.L. et al., "Ease Vectors for Rapid Stable Expression of Recombinant Antibodies", Biotechnol. Prog. 19:1433-1438 (2003).

Bouhassira E.E. et al., "Transcriptional Behaviour of LCR Enhancer Elements Integrated at the Same Chromosomal Locus by Recombinase-Mediated Cassette Exchange", Blood 90(9):3332-3344 (Nov. 1, 1997).

Fukushige S. et al., "Genomic Targeting With a Positive-Selection Lox Integration Vector Allows Highly Reproducible Gene Expression in Mammalian Cells", Proc. Natl. Acad. Sci. USA 89:7905-7909 (Sep. 1992).

Kito M. et al., "Construction of Engineered CHO Strains for High-Level Production of Recombinant Proteins", App Microbiol Biotechnol 60:442-448 (2002).

Koduri R.K. et al., "An Efficient Homologous Recombination Vector pTV(I) Contains a Hot Spot for Increased Recombinant Protein Expression in Chinese Hamster Ovary Cells" Gene 280:87-95 (2001).

Kwaks T.H.J. et al., "Employing Epigenetics to Augment the Expression of Therapeutic Proteins in Mammalian Cells", Trends in Biotechnology 24(3):137-142 (Mar. 2006).

Li Q. et al., "Locus Control Regions", Blood 100(9):3077-3086 (Nov. 1, 2002).

Mielke C. et al., "Anatomy of Highly Expressing Chromosomal Sites Targeted by Retroviral Vectors", Biochemistry 35:2239-2252 (1996).

Shmerling D. et al., "Strong and Ubiquitous Expression of Transgenes Targeted into the B-Actin Locus by Cre/Lox Cassette Replacement", Genesis 42:229-235 (2005).

Svetlova E.Y. et al., "Mammalian Recombination Hot Spot in a DNA Loop Anchorage Region: a Model for the Study of Common Fragile Sites", Journal of Cellular Biochemistry Supplement 36:170-178 (2001).

*Primary Examiner* — Addison D Ault

(74) *Attorney, Agent, or Firm* — Scully, Scott, Murphy & Presser, P.C.; Kristan Lansbery

(57) ABSTRACT

Expression-enhancing nucleotide sequences for expression in eukaryotic systems are provided that allow for enhanced and stable expression of recombinant proteins in eukaryotic cells. Enhanced expression and stability regions (EESYRs) are provided for expression of a gene of interest in a eukaryotic cell. Chromosomal loci, sequences, and vectors are provided for enhanced and stable expression of genes in eukaryotic cells.

26 Claims, 14 Drawing Sheets

Specification includes a Sequence Listing.

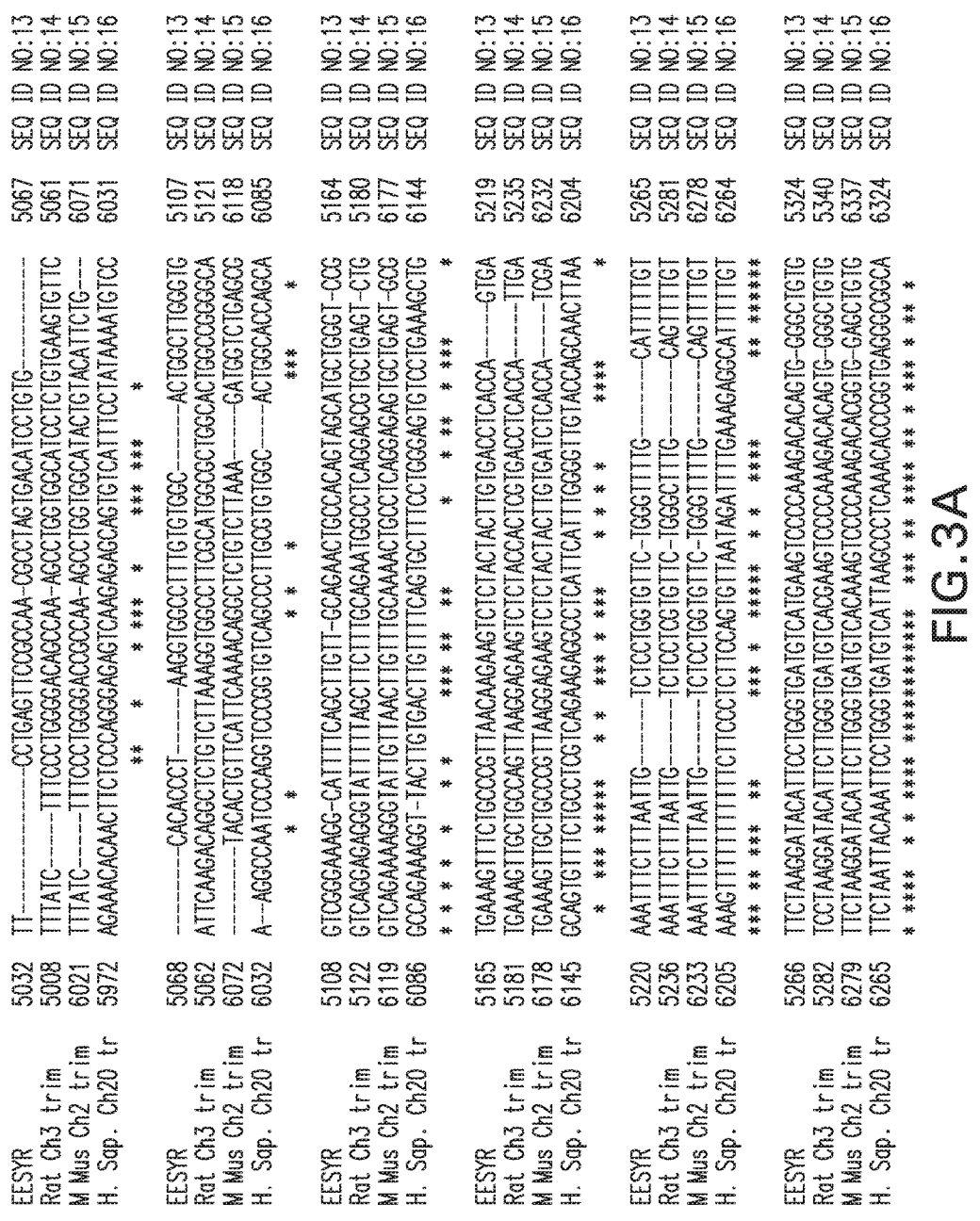

```
EESYR            5032  TT-------------CCTGAGTTCCGCCAA-CGCCTAGTGACATCCTGTG----------  5067  SEQ ID NO:13
Rat Ch3 trim     5008  TTTATC-----TTTCCCTGGGGACAGCCAA-AGCCTGGTGGCATCCTCTGTGAAGTGTTC  5061  SEQ ID NO:14
M Mus Ch2 trim   6021  TTTATC-----TTTCCCTGGGGACCGCCAA-AGCCTGGTGGCATACTGTACATTCTG---  6071  SEQ ID NO:15
H. Sap. Ch20 tr  5972  AGAAACACAACTTCTCCCAGGGAGAGTCAAGAGAGCAGTGTCATTTCCTATAAAATGTCC  6031  SEQ ID NO:16
                                      **   *    * ***  *    *** ***    *

EESYR            5068  --------CACACCCT------AAGGTGGCCTTTGTGTGGC------ACTGGCTTGGGTG  5107  SEQ ID NO:13
Rat Ch3 trim     5062  ATTCAAGACAGGCTCTGTCTTAAAGGTGGCCTTCGCATGGCGCTGGCACTGCCCGGGGCA  5121  SEQ ID NO:14
M Mus Ch2 trim   6072  --------TACACTGTTCATTCAAAACAGGCTCTGTCTTAAA-----GATGGTCTGAGCG  6118  SEQ ID NO:15
H. Sap. Ch20 tr  6032  A--AGGCCAATCCCAGGTCCCGGTGTCAGCCCTTGCGTGTGGC----ACTGGCACCAGCA  6085  SEQ ID NO:16
                                *  *               * *   *              ***     *

EESYR            5108  GTCGGGAAAGG-CATTTTCAGCTTGTT-GCAGAACTGCCACAGTAGCATGCTGGGT-CCG  5164  SEQ ID NO:13
Rat Ch3 trim     5122  GTCAGGAGAGGGTATTTTTAGCTTCTTTGCAGAATGGCCTCAGGAGCGTGCTGAGT-CTG  5180  SEQ ID NO:14
M Mus Ch2 trim   6119  GTCAGAAAAGGGTATTGTTAACTTGTTTGCAAAACTGCCTCAGGAGAGTGCTGAGT-GCG  6177  SEQ ID NO:15
H. Sap. Ch20 tr  6086  GCCAGAAAGGT-TACTTGTGACTTGTTTTCAGTGCTTTCCTGGGAGTGTCCTGAAAGCTG  6144  SEQ ID NO:16
                       * * * *  *   * *     *** **  **       *   * **  * ***       *

EESYR            5165  TGAAAGTTTCTGCCCGTTAACAAGAAGTCTCTACTACTTGTGACCTCACCA-----GTGA  5219  SEQ ID NO:13
Rat Ch3 trim     5181  TGAAAGTTGCTGCCAGTTAAGGAGAAGTCTCTACCACTCGTGACCTCACCA-----TTGA  5235  SEQ ID NO:14
M Mus Ch2 trim   6178  TGAAAGTTGCTGCCCGTTAAGGAGAAGTCTCTACTACTTGTGATCTCACCA-----TCGA  6232  SEQ ID NO:15
H. Sap. Ch20 tr  6145  GCAGTGTTTCTGCCTCGTCAGAAGAGGCCTCATTCATTTGGGGTTGTACCAGCAACTTAA  6204  SEQ ID NO:16
                         *  *** *****   * *  *** * ***    * * * *     ****        *

EESYR            5220  AAATTTCTTTAATTG------TCTCCTGGTGTTC-TGGGTTTTG-------CATTTTTGT  5265  SEQ ID NO:13
Rat Ch3 trim     5236  AAATTTCTTTAATTG------TCTCCTCGTGTTC-TGGGCTTTG-------CAGTTTTGT  5281  SEQ ID NO:14
M Mus Ch2 trim   6233  AAATTTCTTTAATTG------TCTCCTGGTGTTC-TGGGTTTTG-------CAGTTTTGT  6278  SEQ ID NO:15
H. Sap. Ch20 tr  6205  AAAGTTTTTTTTTTTCTTCCCTCTTCCAGTGTTAATAGATTTTGAAAGAGGCATTTTTGT  6264  SEQ ID NO:16
                       *** ** ***  **        *** *  *****  * *  ****       ** ******

EESYR            5266  TTCTAAGGATACATTCCTGGGTGATGTCATGAAGTCCCCAAAGACACAGTG-GGGCTGTG  5324  SEQ ID NO:13
Rat Ch3 trim     5282  TCCTAAGGATACATTCTTGGGTGATGTCACGAAGTCCCCAAAGACACAGTG-GGGCTGTG  5340  SEQ ID NO:14
M Mus Ch2 trim   6279  TTCTAAGGATACATTCTTGGGTGATGTCACAAAGTCCCCAAAGACACGGTG-GAGCTGTG  6337  SEQ ID NO:15
H. Sap. Ch20 tr  6265  TTCTAATTACAAATTCCTGGGTGATGTCATTAAGCCCTCAAACACCCGGTGAGGGCGGCA  6324  SEQ ID NO:16
                       * ****  * * **** ************  *** ** **** ** * *** * ** *
```

FIG. 3A

```
EESYR            5325  TTGGATTGGGAAAGAT-------------GATTTATCTGG-GGTGTCAAAAGGAAAAGAAG  5371  SEQ ID NO:13
Rat Ch3 trim     5341  TTAGATCGGGACAGACAATATTGCTGAGGATTTATCTGAAGGTGTCAAAAGGAGAAGAAG  5400  SEQ ID NO:14
M Mus Ch2 trim   6338  TTAGATGGGGAAAGACAGT-CTGCTGAGGATTTATCTGGAACTGTCAGAAGGAAAAGAAG  6396  SEQ ID NO:15
H. Sap. Ch20 tr  6325  CTGAATGGGGAAAGACAATA-TGCTAACAAGTTATCTGAGGGTGTCAGAAAGAAATGATG  6383  SEQ ID NO:16
                        *  ** **** ***               * *******    ***** ** ** * ** *

EESYR            5372  GGAAACAGG-CACTTGGGA-AAATGTCCTCCCGCCCACCCGAATTTTGGCTT-GGCAACC  5428  SEQ ID NO:13
Rat Ch3 trim     5401  GGAAACAGGGCACTCAGGG-AAATGGCCTCTAGTCT----GAGTTCTGGCTC-AGCAACA  5454  SEQ ID NO:14
M Mus Ch2 trim   6397  GTAAATGGGGCACTTGGGA-AAGTGGCCTCTAGTTT----GACTTCTGGCTT-AGCAAAG  6450  SEQ ID NO:15
H. Sap. Ch20 tr  6384  AAAAACAGTACAGTTGGGGGAAATGTTTTCCAGCCT----GCTTTCTGGTTTTAGCCGACT  6439  SEQ ID NO:16
                         ***  *  ** *  **  ** **   **  *       *  ** *** *   ** *

EESYR            5429  GT-GGTGGAGGAGCAAGAAACACGTGGACGTTTGA-GGAGGCAT-GGGGTCCTAGGAGGA  5485  SEQ ID NO:13
Rat Ch3 trim     5455  GA-GGTGGGGAGATAAGGCACACACAGTGGTTAGAAGGAGTCATCAGGGTTCTGGGAGGA  5513  SEQ ID NO:14
M Mus Ch2 trim   6451  GT-TGTGGGGAGATAAGGCATACACAGTAGTTAGCAGGAGGCAACAGGGTCCTGGGAGGA  6509  SEQ ID NO:15
H. Sap. Ch20 tr  6440  GCATGGGAAGAGATAAGACACACATGGCTTTTATAAGGAGCCATCGGGATCTCTAGGGGA  6499  SEQ ID NO:16
                       *   * *  *    ***  * **   *   **    **** **   ** *     * ***

EESYR            5486  CAGGAACCAGAAGGAGAGAGCTGGGCTGACAGCCTGCAGGCATTGCACAGTTTC--AGAA  5543  SEQ ID NO:13
Rat Ch3 trim     5514  CAGGAGGCAGGAG----AGGCAGGGCTGACAGTGTGCAATCATTGTGTAGTCTC--CCAA  5567  SEQ ID NO:14
M Mus Ch2 trim   6510  CGCGAGGCAGAAGGAG-AGGCTGGGCTGACAGCATGCAATCATTGCATAGTCTC--CAAA  6566  SEQ ID NO:15
H. Sap. Ch20 tr  6500  CATGAGGCAGGACAAAAGAATTGGGCTGAAAGCATCCAATCATCACATATTCACGGAGAA  6559  SEQ ID NO:16
                       *  ** **** **         ******* **  * **  ***     * *  *    **

EESYR            5544  GGAGATTACAGCATGACTGAG------TTTTTAGGGATCCAACAGGGACCTG---GGTAG  5594  SEQ ID NO:13
Rat Ch3 trim     5568  GGAGATTACAACATGGCTGAA------TTTTCAGGGGTCCAACGGAGACTGT---AGTGG  5618  SEQ ID NO:14
M Mus Ch2 trim   6567  GGAGATTGCAACATGGCTGAG------TTTTCAGAGGTCCTACAGAGCCCGT---GGTAG  6617  SEQ ID NO:15
H. Sap. Ch20 tr  6560  AGAGATTACAATATAGCAGAGGAAGCTCTTCCAGGGCTCCTACAGGGACCTTTGGGACAA  6619  SEQ ID NO:16
                        ****** **  **  * **        **  ** * *** ** * * *

EESYR            5595  AGATTCTGTGGGCTCTGAGGCAACTTGACCTCAGCCAGATGGTATTTGAATAACCTGCTC  5654  SEQ ID NO:13
Rat Ch3 trim     5619  AGATTCTGTGGGTTCTGAGACAACTTGACTTCAGCCAGATGGCATTTGAATAAC------  5672  SEQ ID NO:14
M Mus Ch2 trim   6618  AGATTCTGTGGGTTCTGAGACAACTTGACTTTAGCCAGATGGTATTTGAGTAATCTGGG-  6676  SEQ ID NO:15
H. Sap. Ch20 tr  6620  AGATTCAGTGGGCTTTGGGACAGCTTGACTTCAACTAGATGGTATTTGAATAATCTGCT-  6678  SEQ ID NO:16
                       ****** ***** * ** * ** ****** * * * ****** ****** ***
```

FIG.3B

```
EESYR             5655  TTAGAGGGAAAACAGACATAGCAAACAGAGCCACGTTTAGTGATGAAACTCTCACTTTGC  5714  SEQ ID NO:17
Rat Ch3 trim      5673  -------------AGCTCCAGCAAGCACAGCCACATTTAGGGATGAAACTCTCACTTTGA  5719  SEQ ID NO:18
M Mus Ch2 trim    6677  --AGAGAGAAAACAGCTACAGCAAACAGGGCCACATTTAGTGACGAAACTCTCACTTTGA  6734  SEQ ID NO:19
H. Sap. Ch20 tr   6679  --GGAGAGAAAACAGATATAGCACACACTGTCACATTTAGCGTTGAAACTCTCGGTTTGA  6736  SEQ ID NO:20
                                     **    ****  **  * *** ***** *  *********  ****

EESYR             5715  CTG---AGTCATGTGCGGCCATGCCCAGGGGTCAGGCTGACACTCAACTCAAAAACAAGT  5771  SEQ ID NO:17
Rat Ch3 trim      5720  CTGT-GAGTCACGTGTAGCTGTGTCCCGAGGTCAGGCTGGCCCTCAGCTCAAAAACAAGT  5778  SEQ ID NO:18
M Mus Ch2 trim    6735  CTGTTGAGTCATTTGCAG-TGGCCCCTGAGGTCAGGCTGGCCCTCAGCTCAAAAACAAGC  6793  SEQ ID NO:19
H. Sap. Ch20 tr   6737  CTAT-GAGTAATGTTCAGCCATGCCCAAGGGTCAGGCCTACACTCA-CTCAGAAACAAGT  6794  SEQ ID NO:20
                        **    *** *  *   *    * **   ********   * **** **** *******

EESYR             5772  GAGAAATTGAAG-----------ACAATCCGTGGTGGCAGCTACTGGAA-GGGCCACCAC  5819  SEQ ID NO:17
Rat Ch3 trim      5779  GAGGGATTGAAGCAATTACTCAGATAATTCACAGCCACAGCTACGGGGA-GGGCCGC---  5834  SEQ ID NO:18
M Mus Ch2 trim    6794  GAGGAACTGAAGCAATTACTCAGATAATCCACAGCCACAGCCACTGGAAAGGGCCAC---  6850  SEQ ID NO:19
H. Sap. Ch20 tr   6795  GGGGAATTGAAGCAATTATTCAGATAATCCATAGACATAGCTACTGGCCAGTGCTGC---  6851  SEQ ID NO:20
                        * *  * *****          * *** *   *    *** ** **   * **  *

EESYR             5820  ATCCCCAGAAAGAGT-------GGAGCTGCTAAAAAGCCAT----------TTGTGATAGGCA  5865  SEQ ID NO:17
Rat Ch3 trim      5835  ATCCCCAGAAACATC-------GGGGTTACTATAAAGCTA-----------GTGGTGGTCA  5877  SEQ ID NO:18
M Mus Ch2 trim    6851  ATCCCCAGAGACAGCACAGCAGGGGTGGGGGTGGGGCTATGAGAAAGTTAGTGATTGTAG  6910  SEQ ID NO:19
H. Sap. Ch20 tr   6852  -ACCCCTGATTTAGCCCA---GAAACAGTAATGCTATTATAAGCT-GTTGGTGATTTGTG  6906  SEQ ID NO:20
                          **** **   *        *                *           *** *

EESYR             5866  CAGTTATCTTGAATGCATGGAGCAGAG---ATTACGGAAAAATCGAGAATGTTAATGAGG  5922  SEQ ID NO:17
Rat Ch3 trim      5878  CAGTTATCTTGAATGTATGGAGCAGAGGAGATTACAGAAAAACCTAGAATGTTAATGAGG  5937  SEQ ID NO:18
M Mus Ch2 trim    6911  CAGTTATCTAGAATGTGCGGAGCAGAGGAGGTTACACAAAAACCTAGAATG---------  6961  SEQ ID NO:19
H. Sap. Ch20 tr   6907  GAGCAATCTTGAATTTATTAAGGAAAGGAGATTATAGAAAAATCCAGAATGCCAATG-GG  6965  SEQ ID NO:20
                         **  **** ****      ** * **    ***   ***** * ******
```

FIG. 3C

ENHANCED EXPRESSION AND STABILITY REGIONS

CROSS-REFERENCE TO RELATED APPLICATIONS

This application is a continuation of U.S. application Ser. No. 15/384,886, filed on Dec. 20, 2016, which is a continuation of U.S. application Ser. No. 14/967,689, filed on Dec. 14, 2015, now U.S. Pat. No. 9,562,238, which is a continuation of U.S. application Ser. No. 13/752,647, filed on Jan. 29, 2013, now U.S. Pat. No. 9,222,106, which is a divisional of U.S. application Ser. No. 12/793,898, filed on Jun. 4, 2010, now U.S. Pat. No. 8,389,239, which is a continuation of U.S. application Ser. No. 12/132,846, filed on Jun. 4, 2008, now U.S. Pat. No. 7,771,997, which claims benefit under 35 U.S.C. 119(e) of U.S. Provisional Application No. 60/933,213, filed Jun. 4, 2007, all of which are herein specifically incorporated by reference in their entirety.

SEQUENCE LISTING

This application hereby incorporates by reference the Sequence Listing submitted in Computer Readable Form as file 3051B_ST25.txt created on Sep. 18, 2012 (79,397 bytes).

BACKGROUND

Field of the Invention

The invention provides for expressing recombinant proteins in eukaryotic cells. In particular, the invention includes methods and compositions for improved expression of proteins in eukaryotic cells by employing expression-enhancing nucleotide sequences. The invention includes enhanced expression and stability region (EESYR) sequences that facilitate enhanced and stable expression of recombinant proteins in eukaryotic cells, and methods of using such sequences.

Description of Related Art

The development of expression systems is an important goal for providing a reliable and efficient source of a given protein for research and therapeutic use. Recombinant protein expression in mammalian cells is often preferred for manufacturing therapeutic proteins due to, for example, the ability of mammalian expression systems to appropriately post-translationally modify recombinant proteins.

Several vectors are available for expression in mammalian hosts, each containing various combinations of cis- and, in some cases, trans-regulatory elements to achieve high levels of recombinant protein with short incubation times. Despite the availability of numerous such vectors, the expression of a recombinant protein achieved in mammalian systems is often unacceptably low or otherwise unsatisfactory. Moreover, developing a cell line that reliably expresses sufficiently high levels of a desired protein often requires time consuming cloning and amplification steps. Accordingly, there is a need in the art for improved mammalian expression systems.

BRIEF SUMMARY

In one aspect, an isolated nucleotide sequence comprising an expression-enhancing sequence selected from a sequence of SEQ ID NO:1-6, or an expression-enhancing fragment thereof, is provided.

In one embodiment, the expression-enhancing sequence comprises an expression-enhancing sequence of SEQ ID NO:5 located at a position within SEQ ID NO:5 selected from nucleotides spanning positions numbered 10-13,515; 20-12,020; 1,020-11,020; 2,020-10,020; 3,020-9,020; 4,020-8,020; 5,020-7,020; 6,020-6,920; 6,120-6,820; 6,220-6,720; 6,320-6,620; 6,420-6,520; 6,460-6,500; 6,470-6,490; and 6,475-6,485. In another embodiment, an expression-enhancing sequence is provided that is selected from the group consisting of nucleotides 5,000-7,400 of SEQ ID NO:5; 5,000-6,500 of SEQ ID NO:5; 6,400-7,400 of SEQ ID NO:5; and nucleotides 6,400-6,500 of SEQ ID NO:5.

In another embodiment, the recombination recognition site is positioned as described above, providing that the expression-enhancing sequence comprises a sequence that is at least 90% identical, more preferably at least 95% identical, most preferably at least 99% identical, to the expression-enhancing sequence of SEQ ID NO:5 or an expression-enhancing fragment thereof.

In one embodiment, the expression-enhancing sequence further comprises at least one recombinase recognition site comprising a sequence independently selected from a loxp site, a lox 511 site, a lox 2272 site, and a frt site. In one embodiment, the recombinase recognition site is within the expression-enhancing sequence. In another embodiment, the recombinase recognition site is immediately adjacent in the 5' direction to the terminal nucleotide of the 5' end or immediately adjacent in the 3' direction to the terminal nucleotide of the 3' end of the expression-enhancing sequence.

In one embodiment, at least two recombinase recognition sites are present within the expression-enhancing sequence. In a specific embodiment, two recombinase recognition sites of opposite orientation are present within the expression-enhancing sequence. In another embodiment, three recombinase recognition sites are present within the expression-enhancing sequence.

In one aspect, an isolated nucleotide sequence is provided that comprises an expression-enhancing sequence that is at least 80% identical, preferably at least 90% identical, more preferably at least 95% identical, most preferably at least 99% identical to an expression-enhancing sequence of SEQ ID NO:1-6 or an expression-enhancing fragment thereof. In one embodiment, the expression-enhancing sequence displays the recited identity to a sequence of SEQ ID NO:5 as described above.

In one aspect, an isolated eukaryotic cell is provided that comprises an expression-enhancing sequence selected from SEQ ID NO:1-6 or an expression-enhancing fragment thereof. In one embodiment, the expression-enhancing sequence comprises an expression enhancing sequence of SEQ ID NO:5 as described above.

In one embodiment, the eukaryotic cell is a mouse, rat, hamster, or human cell. In a specific embodiment, the eukaryotic cell is a CHO cell.

In one embodiment, the eukaryotic cell further comprises at least one recombinase recognition sequence within the expression-enhancing sequence. In a specific embodiment, the at least one recombinase recognition sequence is independently selected from a loxp site, a lox 511 site, a lox 2272 site, and a frt site. In one embodiment, the recombinase recognition site is immediately adjacent in the 5' direction to the terminal nucleotide of the 5' end or immediately adjacent in the 3' direction to the terminal nucleotide of the 3' end of the expression-enhancing sequence.

In one embodiment, at least two recombinase recognition sites are present within the expression-enhancing sequence.

In a specific embodiment, two recombinase recognition sites are of opposite orientation and are present within the expression-enhancing sequence. In another embodiment, three recombinase recognition sequences are present, and one of the three recombinase recognition sequences is in an orientation opposite to the two remaining recombinase recognition sequences.

In one embodiment, the recombinase recognition site in the expression-enhancing sequence of SEQ ID NO:5 is located at a position within SEQ ID NO:5 selected from nucleotides spanning positions numbered 10-13,515; 20-12,020; 1,020-11,020; 2,020-10,020; 3,020-9,020; 4,020-8,020; 5,020-7,020; 6,020-6,920; 6,120-6,820; 6,220-6,720; 6,320-6,620; 6,420-6,520; 6,460-6,500; 6,470-6,490; and 6,475-6,485. In another embodiment, the recombinase recognition site in in a sequence that is selected from the group consisting of nucleotides 5,000-7,400 of SEQ ID NO:5; 5,000-6,500 of SEQ ID NO:5; 6,400-7,400 of SEQ ID NO:5; and nucleotides 6,400-6,500 of SEQ ID NO:5. In a specific embodiment, the recombinase recognition site is located within nucleotides 6400-6500 of SEQ ID NO:5. In another specific embodiment, the recombinase recognition site is inserted before, after, or within the “act” triplet of nucleotides 6471 to 6473 of SEQ ID NO:5 in an expression-enhancing sequence of SEQ ID NO:5.

In another specific embodiment, the recombination recognition site is positioned as described above, with the caveat that the expression-enhancing sequence comprises a sequence that is at least 90% identical, more preferably at least 95% identical, most preferably at least 99% identical, to nucleotides 5218 through 6048 of SEQ ID NO:5 or an expression-enhancing fragment thereof.

In a specific embodiment, the cell is a CHO cell and the recombinase recognition site is inserted in the CHO cell genome at or within the “act” triplet of nucleotides 6,471 to 6,473 of SEQ ID NO:5.

In one embodiment, a first GOI is inserted within the expression-enhancing sequence of SEQ ID NO:5 as described above, and the first GOI is optionally operably linked to a promoter, wherein the promoter-linked GOI (or the GOI) is flanked 5' by a first recombinase recognition site and 3' by a second recombinase recognition site. In another embodiment, a second GOI is inserted 3' of the second recombinase recognition site, and the second GOI is flanked 3' by a third recombinase recognition site.

In a specific embodiment, the GOI is operably linked to a promoter capable of driving expression of the GOI, wherein the promoter comprises a eukaryotic promoter that is regulatable by an activator or inhibitor. In another specific embodiment, the eukaryotic promoter is operably linked to a prokaryotic operator, and the eukaryotic cell optionally further comprises a prokaryotic repressor protein.

In another embodiment, one or more selectable markers are included between the first and the second and/or the second and the third recombinase recognition sites. In a specific embodiment, the first and/or the second genes of interest and/or the one or more selectable markers are operably linked to a promoter, wherein the promoter may be the same or different. In a specific embodiment, the promoter comprises a eukaryotic promoter (such as, for example, a CMV promoter), optionally controlled by a prokaryotic operator (such as, for example, a tet operator). In a specific embodiment, the cell further comprises a gene encoding a prokaryotic repressor (such as, for example, a tet repressor).

In another embodiment, the cell further comprises a gene capable of expressing a recombinase. In a specific embodiment, the recombinase is a Cre recombinase.

In one aspect, an isolated eukaryotic cell is provided that comprises an expression-enhancing sequence that is at least 80%, more preferably at least 90%, more preferably at least 95%, most preferably at least 99% identical to an expression-enhancing sequence of SEQ ID NO:1-6 or an expression-enhancing fragment thereof. In a specific embodiment, expression-enhancing sequence is a sequence within SEQ ID NO:5 as described above.

In one aspect, a eukaryotic host cell is provided, comprising an expression-enhancing sequence selected from SEQ ID NO:1-6 or an expression-enhancing fragment thereof, comprising a first recombinase recognition site followed by a first eukaryotic promoter, a first marker gene, a second eukaryotic promoter, a second marker gene, a second recombinase recognition site, a third eukaryotic promoter, a third marker gene, and a third recombinase recognition site. In one embodiment, the expression-enhancing sequence is within SEQ ID NO:5 as described above.

In one embodiment, the first, second, and third recombinase recognition sites are different. In a specific embodiment, the recombinase recognition sites are selected from a loxp site, a lox 511 site, a lox 2272 site, and a frt site.

In one embodiment, the first marker gene is a drug resistance gene. In a specific embodiment, the drug resistance gene is a puromycin resistance gene. In another embodiment, the second and third marker genes encode two different fluorescent proteins. In one embodiment, the two different fluorescent proteins are selected from *Discosoma* coral (DsRed), green fluorescent protein (GFP), enhanced green fluorescent protein (eGFP), cyano fluorescent protein (CFP), enhanced cyano fluorescent protein (eCFP), and yellow fluorescent protein (YFP). In a specific embodiment, the two different fluorescent proteins are eCFP and DsRed.

In one embodiment, the first, second, and third promoters are the same. In another embodiment, the first, second, and third promoters are different. In another embodiment, the first promoter is different from the second and third promoters, and the second and third promoters are the same. In a specific embodiment, the first promoter is an SV40 late promoter, and the second an third promoters are each a human CMV promoter.

In one aspect, a eukaryotic host cell is provided, comprising an expression-enhancing sequence selected from SEQ ID NO:1-6, or an expression-enhancing fragment thereof, at least one recombinase recognition site within the expression-enhancing sequence, and at least one gene of interest (GOI) within the expression-enhancing sequence. In one embodiment, the expression-enhancing sequence is a sequence within SEQ ID NO:5, as described above.

In one embodiment, the cell comprises a first recombinase recognition site followed by a first promoter operably linked to a first GOI. In another embodiment, the first GOI is followed by a second recombinase recognition site. In another embodiment, the second recombinase recognition site is followed by a second promoter operably linked to a second GOI. In another embodiment, the second GOI is followed by a third recombinase recognition site. In another embodiment, at least one marker is operably linked to a third promoter and is located between the second recombinase recognition site and the second promoter. In one embodiment, the first recombinase recognition site is oriented in an opposite orientation to the second and third recombinase recognition sites. In one embodiment the first and second promoters are eukaryotic promoters operably linked to a prokaryotic operator. In one embodiment, the first and second promoters are CMV promoters operably linked to tet operator sequences. In another embodiment, the cell further comprises a gene capable of expressing a prokaryotic repressor. In one embodiment, the prokaryotic repressor is a tet repressor. In one embodiment, the cell comprises a gene capable of expressing a Cre recombinase.

In one embodiment, a first and a second marker gene are located between the second recombinase recognition site and the second promoter, and an IRES is between the first and second marker genes. In another embodiment, the first codon (ATG) of the first marker gene is immediately 5' to the second recombinase recognition site, and the second codon of the first marker gene is immediately 3' to the second recombinase recognition site. In another embodiment, the first marker gene contains an intron and the second recombinase recognition site is located within the intron such that the amino-terminal half of the first marker gene and the 5' half of the intron are located 5' of the second recombinase recognition site and the 3' half of the intron and carboxy-terminal half of the first marker gene are immediately 3' to the second recombinase recognition site.

In one embodiment, the first, second, and third recombinase recognition sites are different. In a specific embodiment, the recombinase recognition sites are selected from a loxp site, a lox 511 site, a lox 2272 site, and a frt site.

In one embodiment, the first marker gene is a drug resistance gene. In a specific embodiment, the drug resistance gene is a hygromycin resistance gene. In another embodiment, the second marker gene encodes a fluorescent protein. In one embodiment, the fluorescent protein is selected from DsRed, GFP, eGFP, CFP, eCFP, and YFP.

In one embodiment, the first, second, and third promoters are the same. In another embodiment, the first, second, and third promoters are different. In another embodiment, the third promoter is different from the first and second promoters, and the first and second promoters are the same. In a specific embodiment, the third promoter is an SV40 late promoter, and the first and second promoters are each a human CMV promoter.

In one embodiment, the first and second promoters are operably linked to a prokaryotic operator. In a specific embodiment, the operator is a tet operator.

In one embodiment, the host cell line has an exogenously added gene encoding a recombinase integrated into its genome, operably linked to a promoter. In a specific embodiment, the recombinase is Cre recombinase. In another embodiment, the host cell has a gene encoding a regulatory protein integrated into its genome, operably linked to a promoter. In a specific embodiment, the regulatory protein is a tet repressor protein.

In one embodiment, the first GOI and the second GOI encode a light chain, or fragment thereof, of an antibody or a heavy chain, or fragment thereof, of an antibody. In a specific embodiment, the first GOI encodes a light chain of an antibody and the second GOI encodes a heavy chain of an antibody.

In one aspect, a method is provided for making a protein of interest, comprising: (a) providing a host cell that comprises an expression-enhancing sequence selected from a sequence of SEQ ID NO:1-6; (b) introducing into the host cell, within the expression-enhancing sequence, a gene of interest (GOI) operably linked to a promoter; (c) maintaining the host cell of (a) under conditions that allow the GOI to express a protein of interest; and, (c) recovering the protein of interest.

In one embodiment, the cell is a CHO cell and the nucleotide sequence is an expression-enhancing sequence of SEQ ID NO:5 as described above.

In one embodiment, the GOI is introduced into the cell employing a targeting vector for homologous recombination, wherein the targeting vector comprises a 5' homology arm homologous to a sequence present in at least one of SEQ ID NO:1-6, a GOI, and a 3' homology arm homologous to a sequence present in at least one of SEQ ID NO:1-6. In another embodiment, the construct further comprises two, three, four, or five or more genes of interest. In another embodiment, one or more of the genes of interest are operably linked to a promoter.

In another embodiment, the GOI is introduced employing an integrase technology, for example, integrase technology employing att sites such as Invitrogen's Gateway™ and Multisite Gateway™ cloning systems which employ bacteriophage lambda att site recombination.

In another embodiment, the expression-enhancing sequence comprises one or more recombinase recognition sites as described above, and the GOI is introduced into the expression-enhancing sequence through the action of a recombinase that recognizes the recombinase recognition site.

In one embodiment, the expression-enhancing sequence comprises two recombinase recognition sites.

In one embodiment, the expression-enhancing sequence comprises a first, a second, and a third recombinase recognition site. In one embodiment, the first, second, and third recombinase recognition sites are different. In another embodiment, the first, second, and third recombinase recognition sites are not in the same orientation. In a specific embodiment, the first site is 5' to the second site, and the second site is 5' to the third site. In another specific embodiment, the second and third sites are in opposite orientation with respect to the first site.

In another embodiment, a first and a second GOI are introduced into the expression-enhancing sequence. In one embodiment, the first GOI is introduced between the first and the second recombinase recognition sites, and the second GOI is introduced between the second and the third recombinase recognition sites. In a specific embodiment, the recombinase recognition sites are independently selected from a loxp site, a lox 511 site, a lox 2272 site, and a frt site.

In another embodiment, the first GOI flanked by recombinase recognition sites on a first vector and the second GOI flanked by recombinase recognition sites on a second vector are introduced into a cell comprising an expression-enhancing sequence that comprises three recombinase recognition sites in a single step.

In one embodiment, the GOI is operably linked to a eukaryotic promoter. In another embodiment, the eukaryotic promoter is operably linked to a prokaryotic operator. In a specific embodiment, the eukaryotic promoter is a CMV promoter and the prokaryotic operator is a tet operator.

In another embodiment, the cell comprises a gene capable of expressing a prokaryotic repressor. In a specific embodiment, the prokaryotic repressor is a tet repressor.

In another embodiment, the cell comprises a gene capable of expressing a recombinase. In a specific embodiment, the recombinase is a Cre recombinase.

In one aspect, a eukaryotic cell is provided, wherein the eukaryotic cell comprises at least one expression-enhancing sequence of SEQ ID NO: 1-6 and at least one exogenously added gene within the expression-enhancing sequence. In one embodiment, the exogenously added gene is operably linked to an exogenously added promoter.

In one embodiment, the expression-enhancing sequence is a sequence of SEQ ID NO:5, and the at least one exogenously added gene integrated or inserted within the expression-enhancing sequence is a human gene. In a specific embodiment, the eukaryotic cell is a CHO cell, the exogenously added gene is a human gene, and the human gene is operably linked to an exogenously added eukaryotic promoter.

In one aspect, a targeting vector for homologous recombination is provided, wherein the targeting vector comprises a 5' homology arm, a GOI, and a 3' homology arm, wherein each homology arm is homologous to a sequence within one of SEQ ID NO:1-6. In one embodiment, the 5' and 3' homology arms are homologous to sequences within SEQ ID NO:5. In one embodiment, the targeting vector comprises two, three, four, or five or more genes of interest. In one embodiment, the GOI is operably linked to a promoter. In another embodiment, each of the two, three, four, or five or more genes of interest are each operably linked to a promoter.

In one aspect, an expression vector is provided, comprising an expression-enhancing nucleotide sequence selected from SEQ ID NO: 1-6 or an expression-enhancing fragment thereof. In one embodiment, the expression-enhancing sequence is within SEQ ID NO:5 as described above.

In one embodiment, the vector further comprises a promoter. In a specific embodiment, the promoter is a human CMV promoter.

In one embodiment, the vector further comprises a cloning site for an expressible gene of interest (GOI). In one embodiment, the nucleotide sequence selected from SEQ ID NO: 1-6 or expression-enhancing fragment thereof is located 3' with respect to the coning site for the expressible GOI. In another embodiment, the nucleotide sequence selected from SEQ ID NO: 1-6 or expression-enhancing fragment thereof is located 5' with respect to the coning site for the expressible GOI.

In a specific embodiment, the vector comprises a nucleotide sequence selected from SEQ ID NO:1-6 or an expression-enhancing fragment, a human CMV promoter, a GOI, and a termination sequence, wherein the nucleotide sequence selected from SEQ ID NO: 1-6, or the expression-enhancing fragment thereof, is located 5' with respect to the CMV promoter. In a specific embodiment, the vector further comprises an intron selected from a CMV-MIE intron and a rabbit β-globin intron.

In one aspect, an expression vector is provided, comprising an expression-enhancing nucleotide sequence that is at least 80% identical, preferably at least 90% identical, more preferably at least 95% identical, most preferably at least 99% identical to a sequence selected from SEQ ID NO:1-6 or an expression-enhancing fragment thereof.

In one aspect, a method is provided for making a protein of interest, comprising: (a) introducing into a host cell an expression vector comprising an expression-enhancing sequence selected from a sequence within SEQ ID NO:1-6 and a GOI that encodes for a protein of interest, wherein the GOI is operably linked to a promoter and operably linked to the expression-enhancing sequence; (b) culturing the host cell of (a) under conditions that allow expression of the GOI; and (c) recovering the protein of interest.

In one embodiment, the enhanced expression and stability region sequence is an expression-enhancing sequence of SEQ ID NO:1-6. In one embodiment, the expression-enhancing sequence is within SEQ ID NO:5 as described above.

In one embodiment, the recombinant protein is selected from the group consisting of a subunit of an immunoglobulin or fragment thereof and a receptor or ligand-binding fragment thereof. In a specific embodiment, the recombinant protein is selected from the group consisting of an antibody light chain or antigen-specific fragment thereof, and an antibody heavy chain or antigen-specific fragment thereof.

In any of the aspects and embodiments described above, the expression-enhancing sequence can be placed in the indicated orientation as indicated in SEQ ID NO:1-6, or in the reverse of the orientation indicated in SEQ ID NO:1-6.

Any of the aspects and embodiments of the invention can be used in conjunction with any other aspect or embodiment of the invention, unless otherwise specified or apparent from the context.

Other objects and advantages will become apparent from a review of the ensuing detailed description.

BRIEF DESCRIPTION OF THE FIGURES

FIGS. 3A-3C show an alignment of Chinese hamster ovary (CHO), mouse, human, and rat EESYR sequences for a fragment of SEQ ID NO:5.

DETAILED DESCRIPTION

Figure 1:
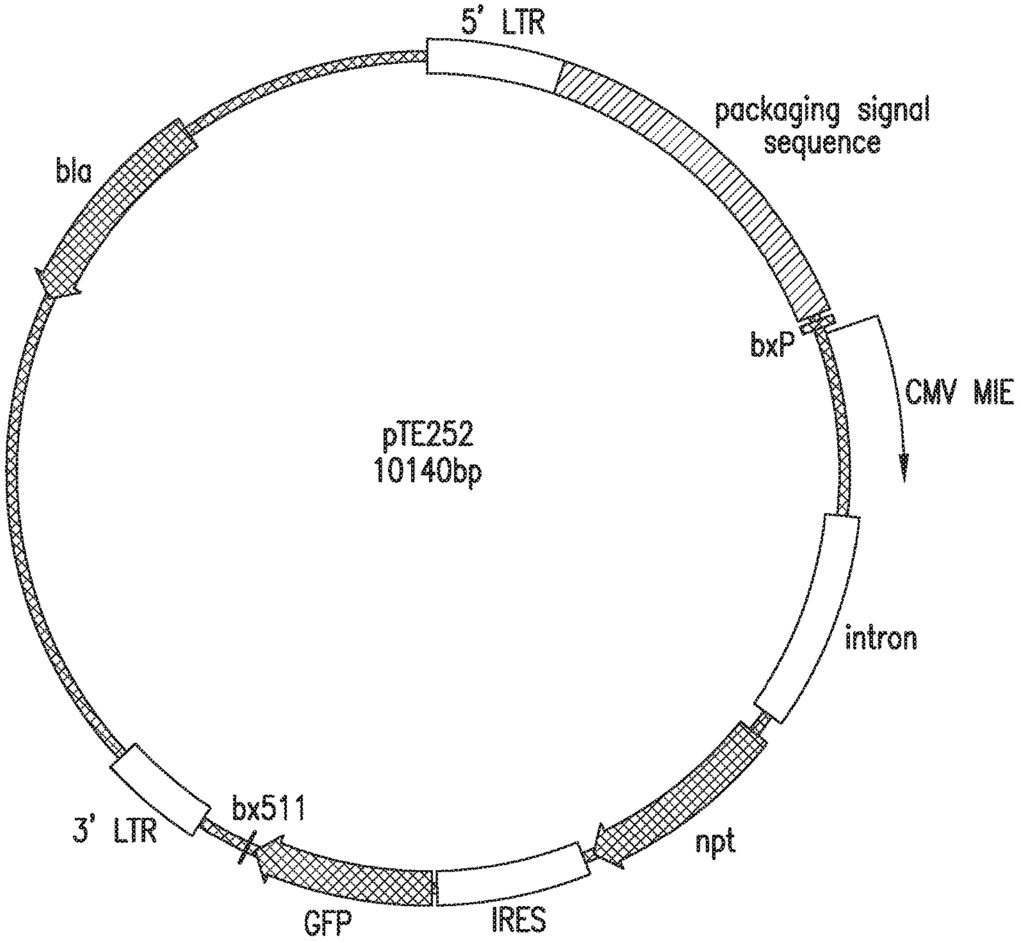
FIG. 1. Schematic diagram of a retroviral construct, pTE252, used for the introduction of nucleic acid construct into a cell genome. LTR: long terminal repeat; LoxP: Cre recombinase recognition sequence: ATAACTTCGTATAATGTATGCTATACGAAGTTGT (SEQ ID NO:7); Lox511: a mutation of LoxP sequences: ATAACTTCGTATAATGTATACTATACGAAGTTAG (SEQ ID NO:8); the Lox511 sequence is recognized by Cre recombinase but the Lox511 site does not recombine with a LoxP site. GFP: Green fluorescent protein; CMV MIE: human cytomegalovirus major immediate early promoter; npt: neomycin phosphotransferase; bla: beta lactamase; IRES: internal ribosomal entry site.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure.

Unless defined otherwise, or otherwise specified, all technical and scientific terms used herein have the same meaning as commonly understood by one of ordinary skill in the art to which this invention belongs.

Although any methods and materials similar or equivalent to those described herein can be used in the practice or testing of the present invention, particular methods and materials are now described. All publications mentioned herein are incorporated herein by reference in their entirety.

Definitions

DNA regions are operably linked when they are functionally related to each other. For example, a promoter is operably linked to a coding sequence if the promoter is capable of participating in the transcription of the sequence; a ribosome-binding site is operably linked to a coding sequence if it is positioned so as to permit translation. Generally, operably linked can include, but does not require, contiguity. In the case of sequences such as secretory leaders, contiguity and proper placement in a reading frame are typical features. An EESYR is operably linked to a GOI where it is functionally related to the gene of interest, for example, where its presence results in enhanced expression of the GOI.

The term "enhanced" when used to describe enhanced expression includes an enhancement of at least about 1.5-fold to at least about 2-fold enhancement in expression over what is typically observed by random integration into a genome, for example, as compared to a pool of random integrants of a single copy of the same expression construct. Fold-expression enhancement observed employing the sequences of the invention is in comparison to an expression level of the same gene, measured under substantially the same conditions, in the absence of a sequence of the invention. As used herein, the phrase "expression-enhancing" is used interchangeably with "enhanced expression and stability" when referring to a region or sequence. An "enhanced expression and stability region," also referred to herein as an "EESYR," is a region or sequence that exhibits more efficient recombination, insert stability, and higher level expression than is typically observed by random integration into a genome.

Enhanced recombination efficiency includes an enhancement of the ability of a locus to recombine (for example, employing recombinase-recognition sites). Enhancement refers to an efficiency over random recombination, which is typically 0.1%. A preferred enhanced recombination efficiency is about 10-fold over random, or about 1%. Unless specified, the claimed invention is not limited to a specific recombination efficiency.

Where the phrase "exogenously added gene" or "exogenously added GOI" is employed with reference to a EESYR, the phrase refers to any gene not present within the EESYR as the EESYR is found in nature. For example, an "exogenously added gene" within a CHO EESYR (e.g., an EESYR comprising a sequence of SEQ ID NO:5), can be a hamster gene not found within the CHO EESYR in nature (i.e., a hamster gene from another locus in the hamster genome), a gene from any other species (e.g., a human gene), a chimeric gene (e.g., human/mouse), or any other gene not found in nature to exist within the CHO EESYR.

Percent identity, when describing an EESYR, is meant to include homologous sequences that display the recited identity along regions of contiguous homology, but the presence of gaps, deletions, or insertions that have no homolog in the compared sequence are not taken into account in calculating percent identity. In explaining the usage of "percent identity" in this context, the following sequence comparison (SEQ ID NO: 9-SEQ ID NO: 12) will be referred to:

```
EESYR         5595  AGATTCTGTGGGCTCTGAGGCAACTTGACCTCAGCCAGATGGTATTTGAATAACCTGCTC  5654
Rat Ch3       5619  AGATTCTGTGGGTTCTGAGACAACTTGACTTCAGCCAGATGGCATTTGAATAAC------  5672
M Mus Ch2     6618  AGATTCTGTGGGTTCTGAGACAACTTGACTTTAGCCAGATGGTATTTGAGTAATCTGGG-  6676
H. Sap Ch20   6620  AGATTCAGTGGGCTTTGGGACAGCTTGACTTCAACTAGATGGTATTTGAATAATCTGCT-  6678
                    ****** ***** * ** * ** ****** * * * ****** ****** ***
```

in which the "EESYR" 5595-5654 sequence is SEQ ID NO: 9, the "Rat Ch3" 5619-5672 sequence is SEQ ID NO: 10, the "M Mus Ch2" 6618-6676 sequence is SED ID NO: 11, and the "H. Sap. Ch20" sequence is SEQ ID NO: 12. As used herein, a "percent identity" determination between the "EESYR" sequence above (for a CHO cell EESYR or fragment thereof) with a rat homolog ("Rat Ch3") would not include a comparison of CHO sequences 5649 through 5654, since the rat homolog has no homologous sequence to compare in an alignment (i.e., the CHO EESYR has an insertion at that point, or the rat homolog has a gap or deletion, as the case may be). Thus, in the comparison above, the percent identity comparison would extend from the "AGATTC" at the 5' end to the "AATAAC" at the 3' end. In that event, the rat homolog differs only in that it has a "T" at CHO EESYR position 5607, an "A" at CHO EESYR position 5614, a "T" at CHO EESYR position 524, and a "C" at CHO EESYR position 5637. Since the comparison is over 54 contiguous bases in a 60 base pair stretch, with only four differences (which are not gaps, deletions, or insertions), there is over 90% identity between the two sequences (CHO and rat) from CHO EESYR position 5595 to CHO EESYR position 5654 (because "percent identity" does not include penalties for gaps, deletions, and insertions).

General Description

The invention is based at least in part on the discovery that there are sequences in a genome that exhibit more efficient recombination, insert stability, and higher level expression than other regions or sequences in the genome. The invention is also based at least in part on the finding that when such expression-enhancing sequences are identified, a suitable gene or construct can be exogenously added in or near the sequences and that the exogenously added gene can be advantageously expressed. Such sequences, termed enhanced expression and stability regions ("EESYRs"), can be engineered to include recombinase recognition sites for placement of genes of interest to create cell lines that are capable of expressing proteins of interest. EESYRs can also be included as in expression constructs such as, for example, expression vectors. Expression vectors comprising EESYRs can be used to express proteins transiently, or can be integrated into a genome by random or targeted recombination such as, for example, homologous recombination or recombination mediated by recombinases that recognize specific recombination sites (e.g., Cre-lox-mediated recombination). Expression vectors comprising EESYRs can also be used to assess efficacy of other DNA sequences, for example, cis-acting regulatory sequences.

The CHO EESYR described in detail herein was identified by random integration of DNA comprising lox sites into a CHO cell genome, followed by selection to identify sequences where expression was enhanced. Random integration and introduction of the lox site was achieved using a retroviral construct. Selection and screening were achieved using drug resistance markers and detectable labels (e.g., fluorescent proteins with FACS screening), employing recombination methods that used site-specific recombination (e.g., lox sites and Cre recombinase). Selection continued until at least a 1.5- to 2-fold enhanced expression over expression observed when randomly integrating an expression construct into the CHO cell genome. Following identification of the EESYR, recombinase recognition sites (in the example provided, lox sites) were maintained in the EESYR for introducing expression cassettes that comprise an expressible GOI, along with any other desirable elements such as, for example, promoters, enhancers, markers, operators, etc.

Figure 2:
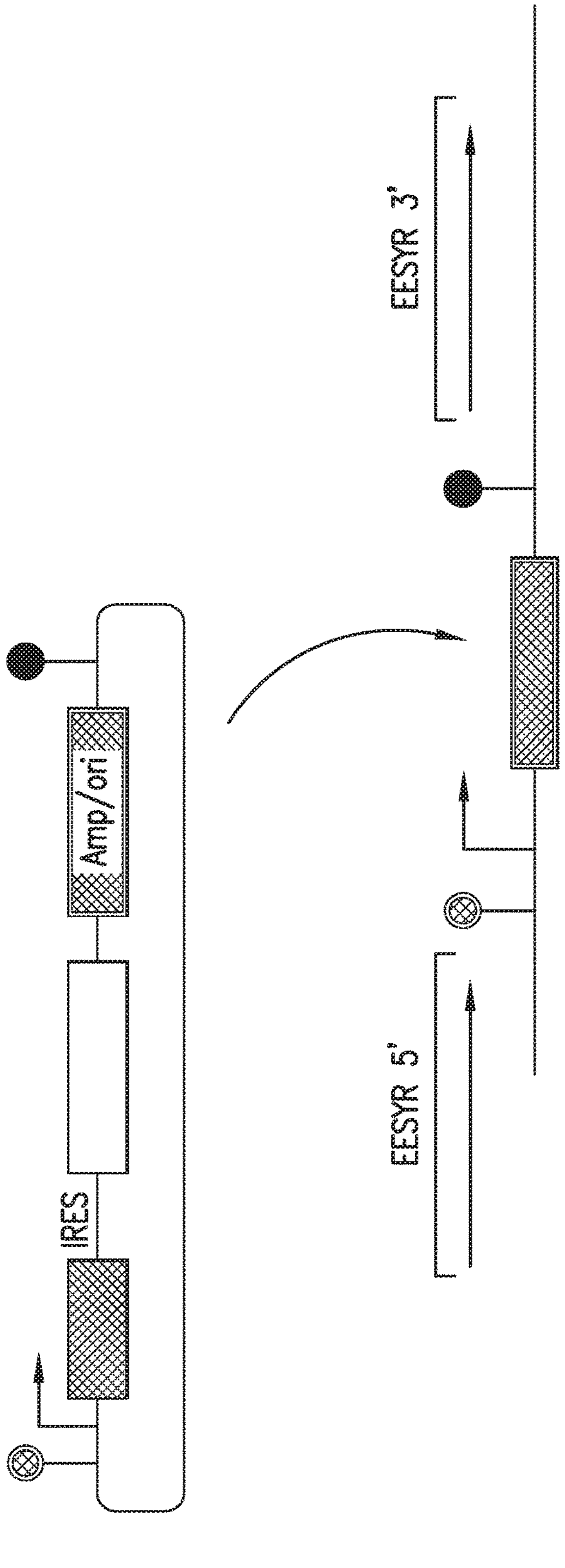
FIG. 2 illustrates a plasmid construct used to identify an EESYR.

An illustration of a plasmid construct used in identifying an EESYR disclosed in this application is shown in FIG. 2. The plasmid rescue construct comprises an expression cassette driven by an promoter, wherein the cassette is flanked on the 5' and 3' ends with recombinase recognition sites (represented by ball-and-stick in FIG. 2). Insertion within an EESYR locus is shown, wherein the insertion results in the plasmid rescue construct replacing an expression cassette that comprises a promoter and a marker, wherein the expression cassette within the EESYR locus is flanked on its 5' and 3' ends by recombinase recognition sites (see FIG. 2).

Compositions and methods are provided for stably integrating a nucleic acid sequence into a eukaryotic cell, wherein the nucleic acid sequence is capable of enhanced expression by virtue of being integrated in or near an EESYR. Cells are provided that contain a recombinase recognition sequence within or near an EESYR, convenient for inserting a GOI, in order to achieve expression of a protein of interest from the GOI. Compositions and methods are also provided for using EESYRs in connection with expression constructs, for example, expression vectors, and for adding an exogenous EESYR into a eukaryotic cell of interest.

Physical and Functional Characterization of an EESYR

The nucleic acid sequences referred to as EESYRs were empirically identified by sequences upstream and downstream of the integration site of a nucleic acid construct (comprising an expression cassette) of a cell line expressing a reporter protein at a high level. The EESYR nucleic acid sequences of the invention provide sequences with a new functionality associated with enhanced expression of a nucleic acid (for example, an exogenous nucleic acid comprising a GOI) that appear to function differently from that previously described for cis-acting elements such as promoters, enhancers, locus control regions, scaffold attachment regions or matrix attachment regions. EESYRs do not appear to have any open reading frames (ORFs), making it unlikely that EESYRs encode novel trans-activator proteins. Transfection experiments demonstrated that EESYR sequences display some characteristics of cis-acting elements. EESYR activity is not detected in transient transfection assays; EESYR sequences also appear to be distinct from promoter and enhancer elements, which are detected with these methods.

Although EESYR sequences described in detail herein were isolated from the genome of two cell lines, EESYR sequences from these two cell lines are the same. EESYR activity was identified in a 6.472 kb fragment of CHO genomic DNA 5' with respect to a unique integration site of a retroviral vector comprising a DsRed reporter encoding sequence and in a 7.045 kb fragment of CHO genomic DNA 3' with respect to the integration site. Expression vectors comprising the isolated 6.472 kb region and the isolated 7.045 kb region and shorter fragments thereof were able to confer upon CHO cells transfected with them high levels of expression of recombinant proteins.

The invention encompasses expression vectors comprising reverse orientated EESYR fragments. Reverse orientated EESYR fragments were also capable of conferring upon CHO cells transfected with them high levels of expression of recombinant proteins.

Other combinations of the fragments described herein can also be developed. Examples of other combinations of the fragments described herein that can also be developed include sequences that include multiple copies of the EESYR disclosed herein, or sequences derived by combining the disclosed EESYR with other nucleotide sequences to achieve optimal combinations of regulatory elements. Such combinations can be contiguously linked or arranged to provide optimal spacing of the EESYR fragments (e.g., by the introduction of spacer nucleotides between the fragments). Regulatory elements can also be arranged to provide optimal spacing of an EESYR with respect to the regulatory elements.

The EESYR sequences disclosed herein were isolated from CHO cells. Homologous expression-enhancing elements are expected to exist in cells from other mammalian species (such as, for examples, humans; see FIGS. 3A-3C) as well as in cell lines derived from other tissue types, and can be isolated by techniques that are well-known in the art, for example, by cross-species hybridization or PCR-based techniques. In addition, changes can be made in the nucleotide sequence set forth in SEQ ID NOs:1-6 by site-directed or random mutagenesis techniques that are well known in the art. The resulting EESYR variants can then be tested for EESYR activity as described herein. DNAs that are at least about 80% identical, preferably at least about 90% identical, more preferably at least about 95% identical, most preferably least about 99% identical in nucleotide sequence to SEQ ID NOs:1-6 or fragments thereof having EESYR activity are isolatable by routine experimentation, and are expected to exhibit EESYR activity. For fragments of EESYR, percent identity refers to that portion of the reference native sequence that is found in the EESYR fragment. Accordingly, homologs of EESYR and variants of EESYR are also encompassed by embodiments of the invention. FIGS. 3A-3C show an alignment of mouse, human, and rat sequences with varying homology to a fragment of SEQ ID NO:5.

Cell populations expressing enhanced levels of a protein of interest can be developed using the methods provided herein. The absolute level of expression will vary with the specific protein, depending on how efficiently the protein is processed by the cell. Cell pools developed with EESYR are stable over time, and can be treated as stable cell lines for most purposes. Cloning steps can be delayed until later in the process of development than is customary for recombinant proteins.

EESYRs and Expression-Enhancing Fragments Thereof

Figure 4A:
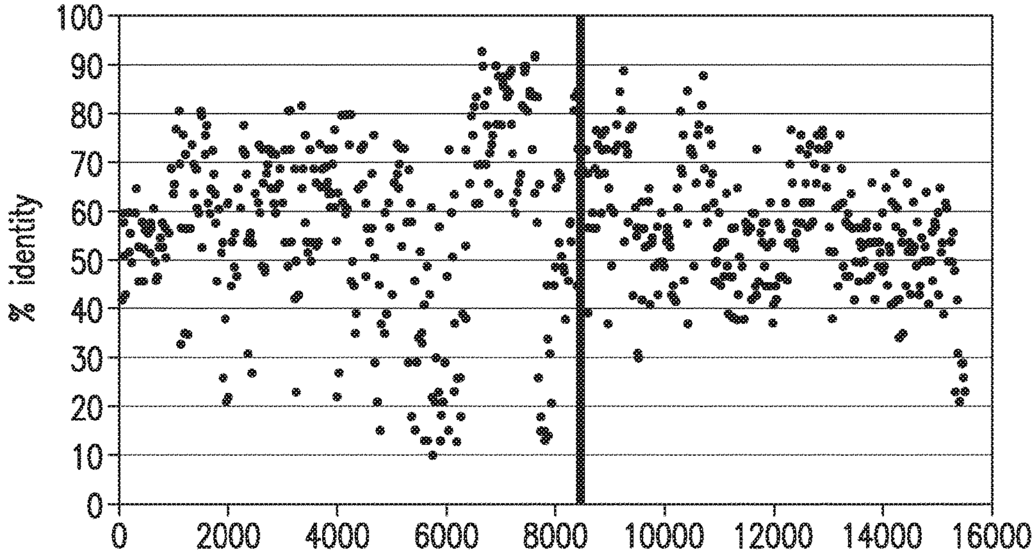
FIGS. 4A-4B show an alignment of SEQ ID NO:5 with mouse, human, and rat sequences.
Figure 4B:
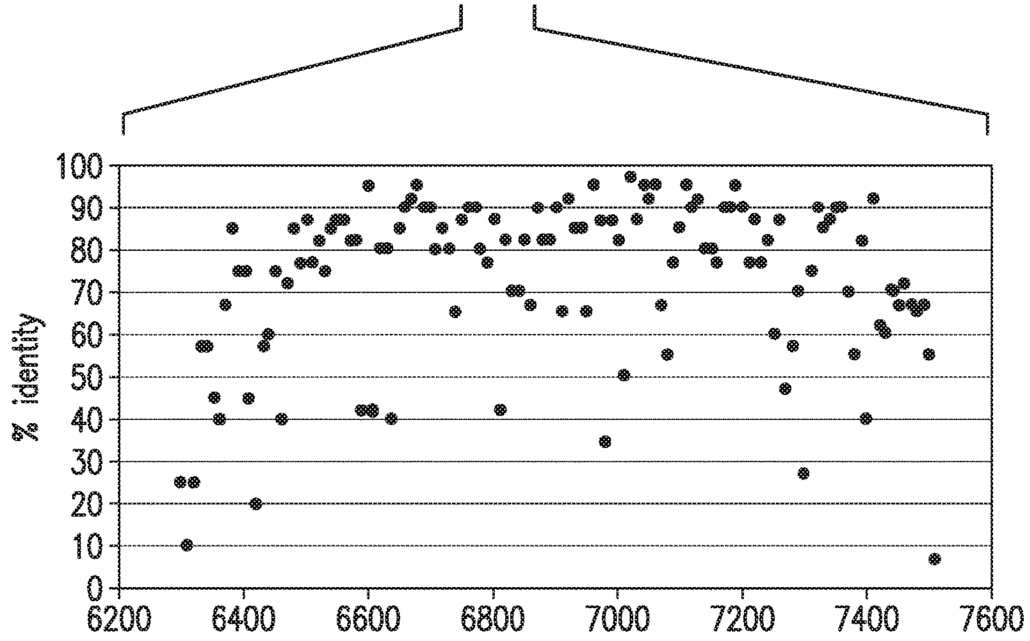

The EESYR genomic locus is conserved among human, mouse and rat genomes. FIG. 4A shows percent identity among EESYR sequences. EESYR sequences, homologous to the 13.515 kb of cloned CHO EESYR DNA of SEQ ID NO:5, were identified among the published human, rat and mouse genomes using BLAST. Sequences were aligned to determine the percent homology using MacVector (9.0). Twenty-five bp increments of the alignment are graphed as the percent identity among CHO, human, mouse and rat EESYR sequences for each consecutive 25 bp segment. As shown in FIG. 4A, the vertical line marks the location of site-specific recombination events to express recombinant protein genes of interest. Percent identity of EESYR sequences adjacent to a site-specific recombination location in an EESYR is shown in FIG. 4B. Ten base pair increments of the aligned sequences corresponding to nt 5022-6110 of a CHO cell EESYR sequence (nucleotides 5022 through 6110 of SEQ ID NO:5) are graphed as the percent identity among CHO, human, mouse and rat EESYR sequences for each consecutive 10 bp segment. Sequences were aligned using MacVector™ 9.0. As shown in FIG. 4B, a significant identity of sequence is present in this fragment of the EESYR cloned from CHO cells. It should be noted that the comparison of FIG. 4B indicates a length of about 1400 bases, whereas the sequence of SEQ ID NO:5 contains 13,515 bases. The FIG. 4B bases appear to extend over a longer stretch due to the existence of gaps. Nucleotide spans recited are those corresponding to numbering in SEQ ID NO:5 unless otherwise indicated. The span of nucleotides from about 6200 to about 7600 as shown in FIG. 4B corresponds to nucleotides of SEQ ID NO:5 numbered about 5,200 to about 6,000.

Accordingly, the invention also includes an expression-enhancing fragment of a nucleotide sequence of SEQ ID NO:5, wherein the expression-enhancing fragment includes the nucleotide sequence indicated by positions about residues 5022 through about 6110 of SEQ ID NO:5, or about 5218 through about 6048 of SEQ ID NO:5; or about 6200 through about 7600, about 6500 to about 7400, or about 6400 to about 6500 shown in FIG. 4B. The invention also encompasses an expression-enhancing fragment of a nucleotide sequence that is at least 80% identical, preferably at least 90% identical, more preferably at least 95% identical, most preferably at least 99% identical to the nucleotide sequence indicated by positions about 6200 through about 7600, or about 6500 through about 7400, or about 6400 through about 6500 shown in FIG. 4B. The invention includes vectors comprising such a fragment, including for transient or stable transfection. The invention also includes a eukaryotic cell comprising such a fragment wherein the fragment is exogenous and is integrated into the cell genome, and cells comprising such a fragment having at least one recombinase recognition site that is within, immediately 5', or immediately 3' to the fragment.

In one embodiment, the expression-enhancing fragment of SEQ ID NO:5 is located at a position within SEQ ID NO:5 selected from nucleotides spanning positions numbered 10-13,515; 20-12,020; 1,020-11,020; 2,020-10,020; 3,020-9,020; 4,020-8,020; 5,020-7,020; 6,020-6,920; 6,120-6,820; 6,220-6,720; 6,320-6,620; 6,420-6,520; 6,460-6,500; 6,470-6,490; and 6,475-6,485.

Figure 5:
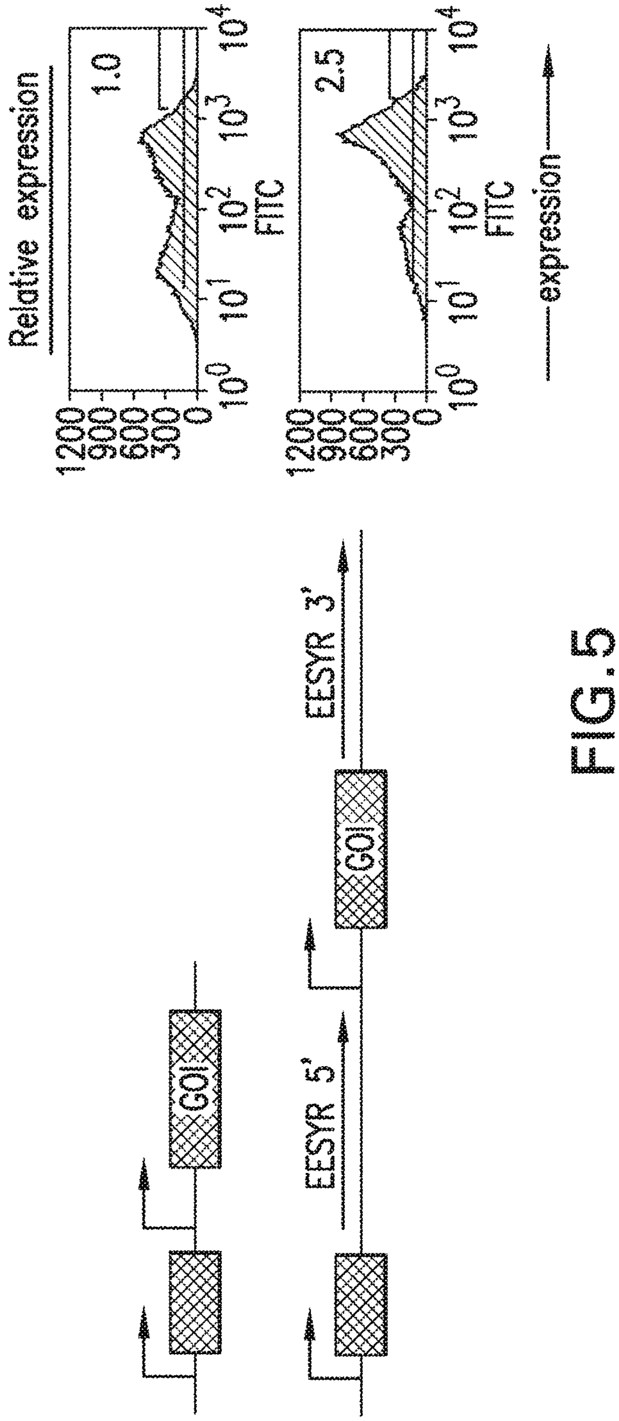
FIG. 5 illustrates that an EESYR, operably linked to a gene of interest (GOI), exhibits enhanced expression over a GOI that is not operably linked to an EESYR. For each plot, major ticks on the y-axis represent 0, 300, 600, 900, and 1200; major ticks on the x-axis represent $10^0$, $10^1$, $10^2$, $10^3$, and $10^4$.

In one embodiment, the EESYR is employed to enhance the expression of a GOI, as illustrated in FIG. 5. FIG. 5 shows a GOI operably linked with a promoter (with an upstream marker having its own promoter) integrated in a non-EESYR position in a CHO cell genome, and a FACS readout showing the distribution of expression in a stably transfected population of cells. In comparison, a GOI operably linked to a promoter integrated at an EESYR position in a CHO cell genome is shown, and a FACS readout showing the distribution of expression in a stably transfected population of cells is also shown. In this embodiment, the GOI expressed within the EESYR locus shows an enhanced expression of about two-fold in comparison to the GOI expressed at a non-EESYR locus.

In various embodiments, expression of a GOI can be enhanced by placing the GOI within an EESYR, 5' to an EESYR, or 3' to an EESYR. The precise distance between the GOI and the EESYR, where the GOI is either 5' or 3' to the EESYR, should be such that the EESYR is operably linked to the GOI. An EESYR is operably linked to the GOI where expression of the GOI—at the selected distance from the EESYR (in the 5' or 3' direction)—retains the ability to enhance expression of the GOI over, for example, expression typically observed due to a random integration event. In various embodiments, enhancement is at least about 1.5-fold to about 2-fold or more. Preferably, enhancement in expression as compared to a random integration, or random expression, is about 2-fold or more.

Figure 6:
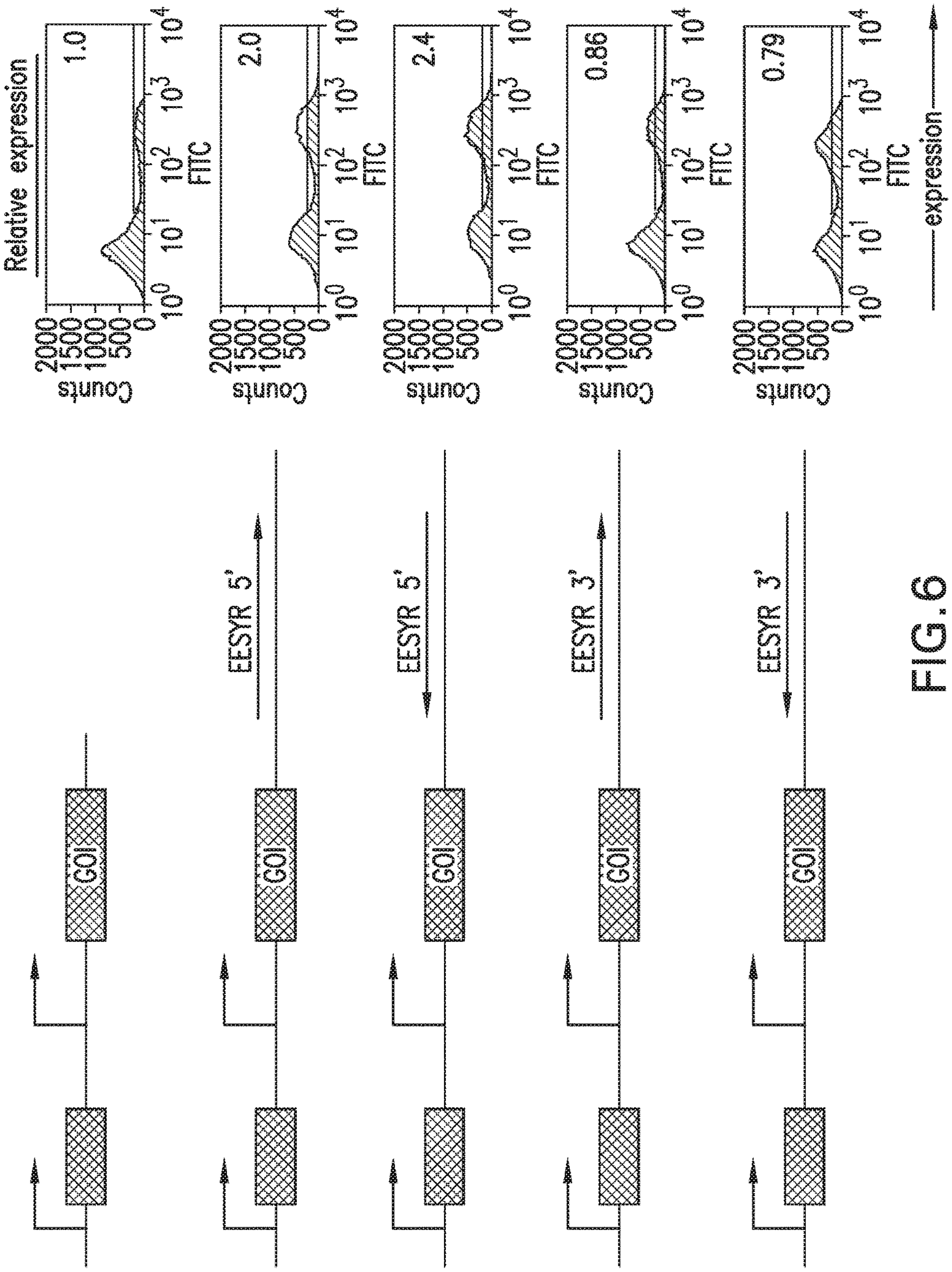
FIG. 6 shows EESYRs compared in their relative ability to enhance expression of an operably linked GOI. For each plot, y-axis major ticks represent Counts of 0, 500, 1,000, 1,500, and 2,000; x-axis major ticks represent FITC of $10^0$, $10^1$, $10^2$, $10^3$, and $10^4$.

FIG. 6 shows an embodiment wherein SEQ ID NO:1 ("EESYR 5') and SEQ ID NO:2 ("EESYR 3'") are compared in their relative ability to enhance expression of an operably linked GOI, wherein the GOI is operably linked to a promoter as well (a marker and a promoter operably linked to the marker are shown 5' to the GOI promoter). Orientation of the EESYR is shown by the direction of the arrow beneath the term "EESYR." The constructs are randomly integrated into a CHO cell genome. Expression is relative to the randomly integrated construct that does not comprise any EESYR. FACS readouts showing relative expression are shown on the right. In FIG. 6, the first EESYR construct employs SEQ ID NO:1; the second EESYR construct employs SEQ ID NO:3; the third EESYR construct is SEQ ID NO:2; the fourth EESYR construct is SEQ ID NO:4. As shown in the figure, SEQ ID NO:3 displays a 2.4-fold enhancement in expression, and SEQ ID NO:1 displays a 2-fold enhancement of expression.

Figure 7:
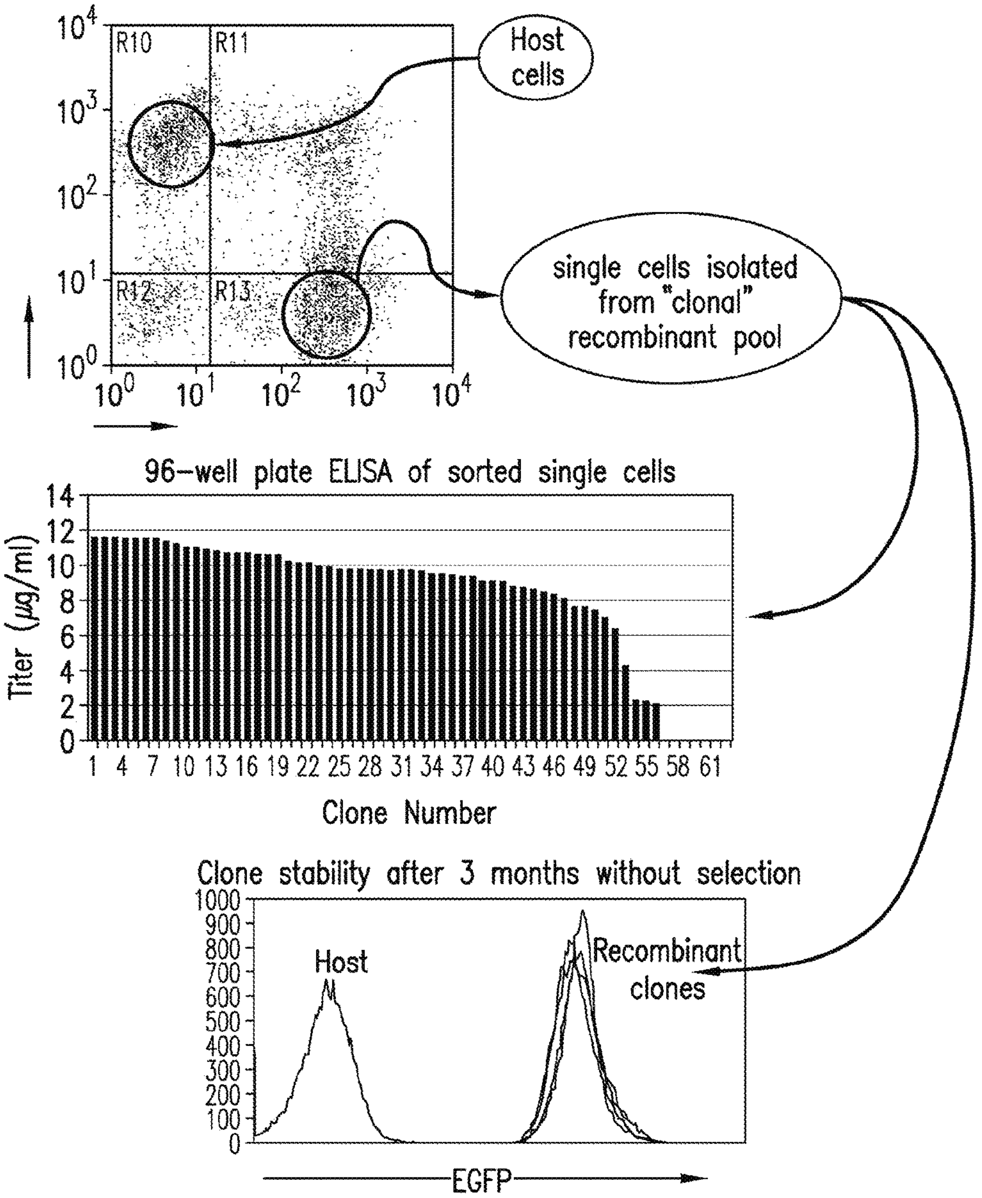
FIG. 7 illustrates clonal characteristics of cells with respect to EESYR functionality. For the top plot, major tick labels on both the y- and x-axes of the top plot represent $10^0$, $10^1$, $10^2$, $10^3$, and $10^4$; quadrant identifiers are R10 and R11 (top, left to right) and R12 and R13 (bottom, left to right). For the middle plot, which shows 96-well plate ELISA results of sorted single cells, the y-axis of the center plot represents Titer (μg/ml), with major tick labels of 0, 2, 4, 6, 8, 10, 12, and 14; whereas the x-axis represents Clone Number (in triplicate) from 1 to 63. For the bottom plot, which shows clone stability after three months without selection, y-axis major ticks represent increments of 100 from 0 to 1000. For the bottom plot, the left peak is for "Host," whereas the right peak is for "Recombinant clones."

EESYR recombinant cell pools display clonal characteristics. FIG. 7 illustrates clonal characteristics of EESYR recombinant pools. In the two-color FACS plot representing a dual parameter histogram of cells labeled with red or green markers (red cells are host CHO cells; green cells are recombinants expressing a GOI), EESYR recombinant pools show clustering in the plot that reflects substantially identical growth and expression, flow cytometry profile, and Southern analysis (not shown). A histogram of ELISAs of single cells demonstrate uniform expression in all clones. Clonal stability is also high after three months without selection.

Figure 8A:
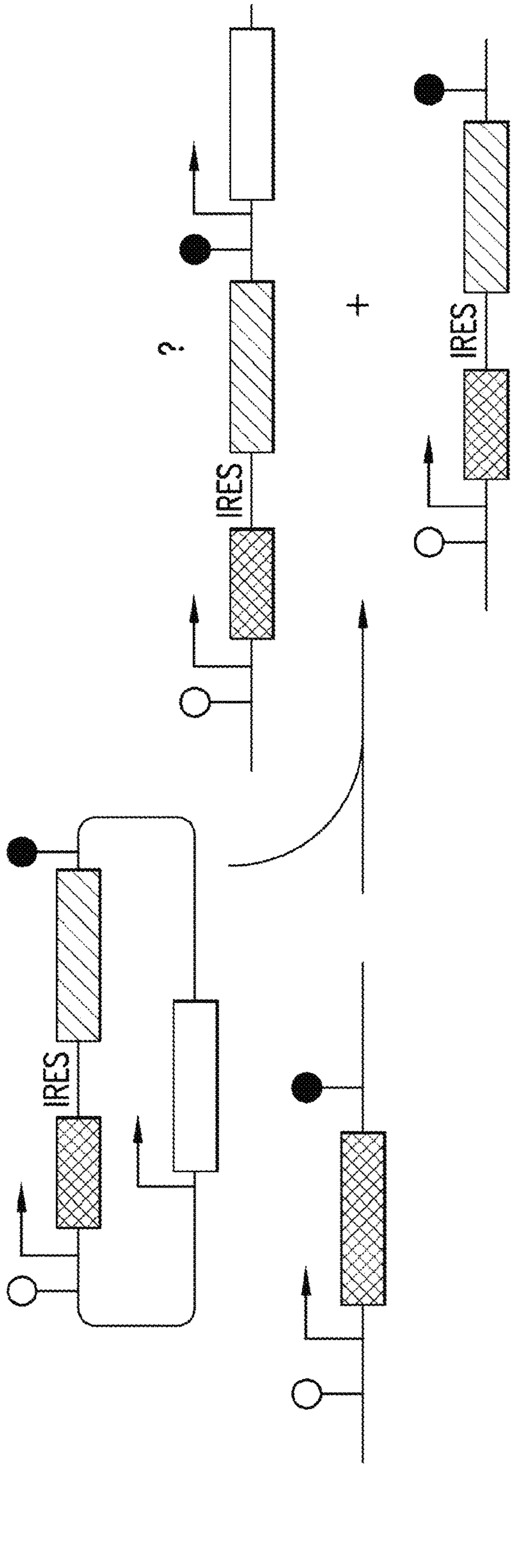
FIGS. 8A-8B illustrate that EESYR cells undergo specific and efficient recombination. In Panel B, y- and x-axes major ticks represent $10^0$, $10^1$, $10^2$, $10^3$, and $10^4$; for each plot, quadrants are (left to right, top) R2 and R3, and (left to right, bottom) R4 and R5.
Figure 8B:
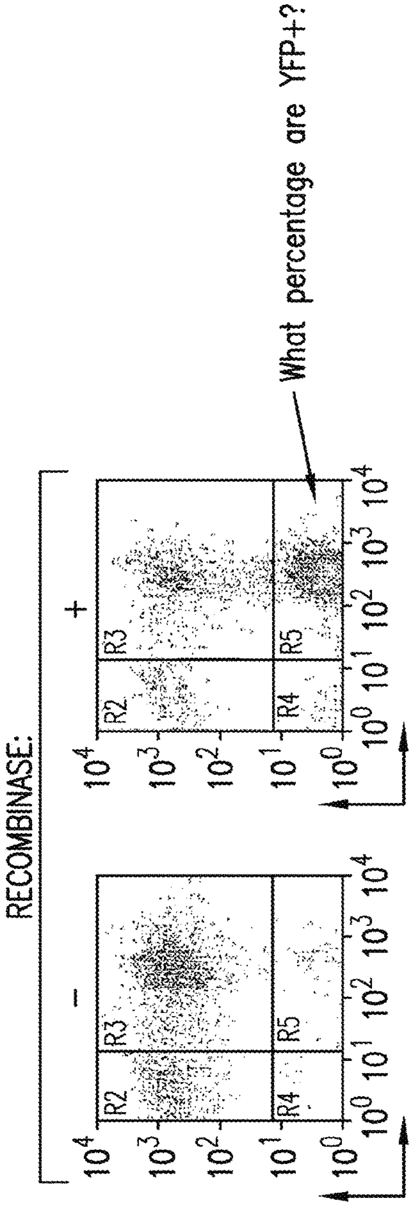

EESYR recombinants undergo specific and efficient recombination, as shown in FIGS. 8A-8B. FIG. 8A shows two markers separated by an IRES and flanked by recombinase recognition sites, and a third marker not flanked by recombinase recognition sites as a random integration control. When recombined at an EESYR locus comprising a marker flanked by two recombinase recognition sites, recombination is specific. FIG. 8B shows little random integration in the absence of recombinase, but efficient and site-specific integration in the presence of recombinase.

Figure 9:
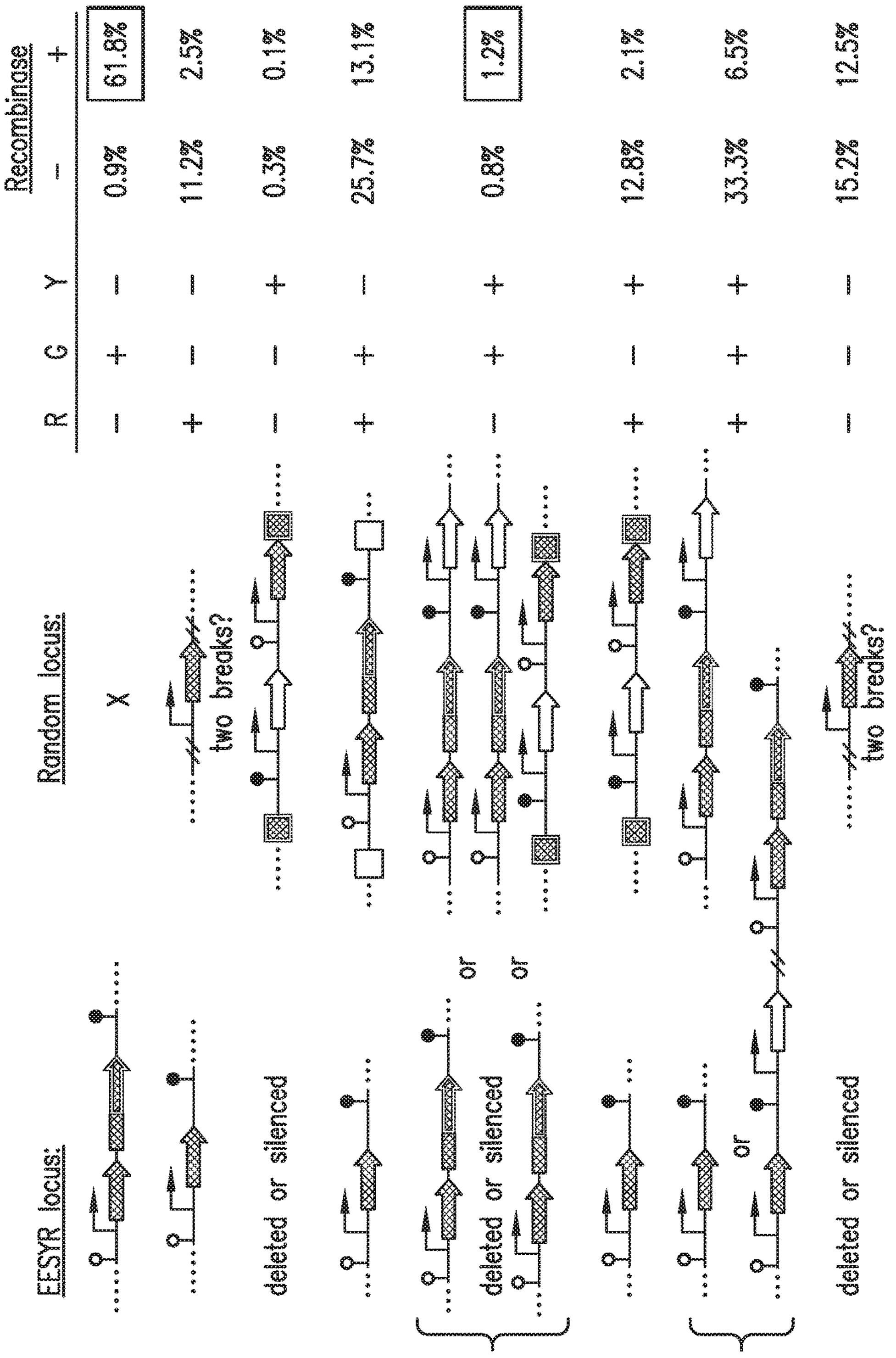
FIG. 9 illustrates the rarity of random integration events in EESYR cells.

Random integration using site specific recombination at an EESYR is rare (see FIG. 9). FIG. 9 shows that when random integration events are visualized, such events represent only a tiny fraction of integration events.

Figure 10:
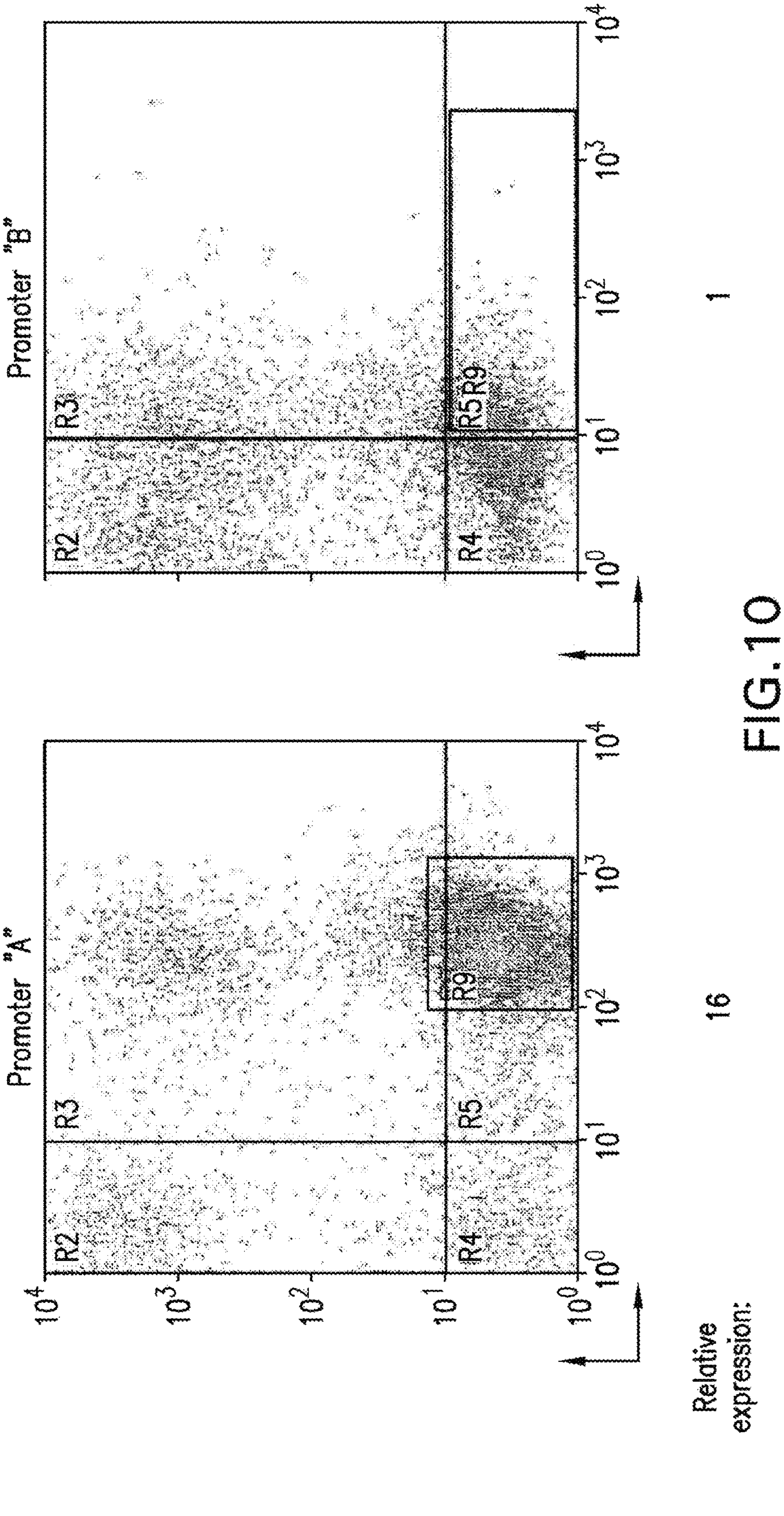
FIG. 10 illustrates testing of cis-acting elements employing EESYR sequences. Major ticks of the y- and x-axes major ticks represent $10^0$, $10^1$, $10^2$, $10^3$, and $10^4$.
Figure 11A:
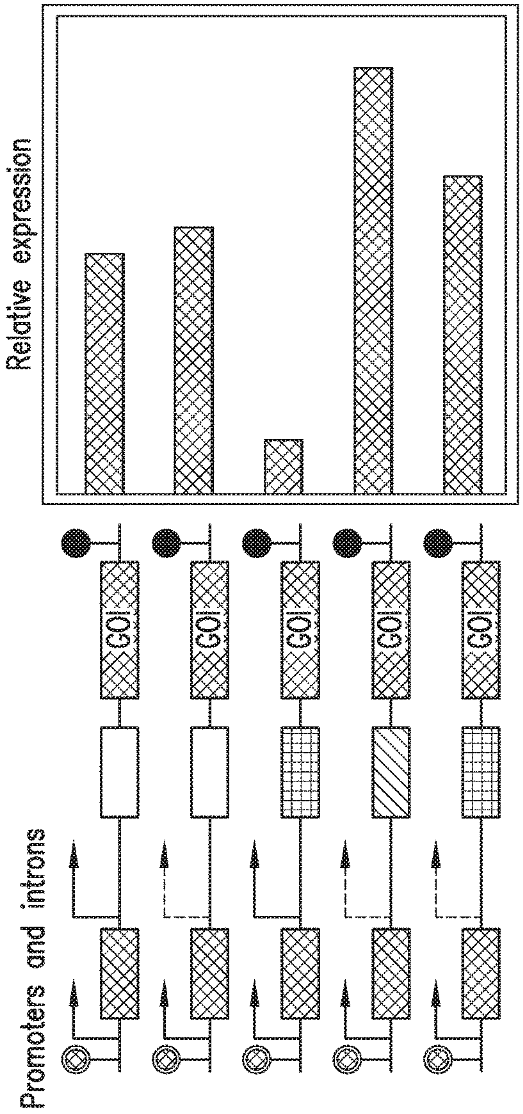
FIGS. 11A-11B illustrate testing promoters, introns, and UTRs using an EESYR system.
Figure 11B:
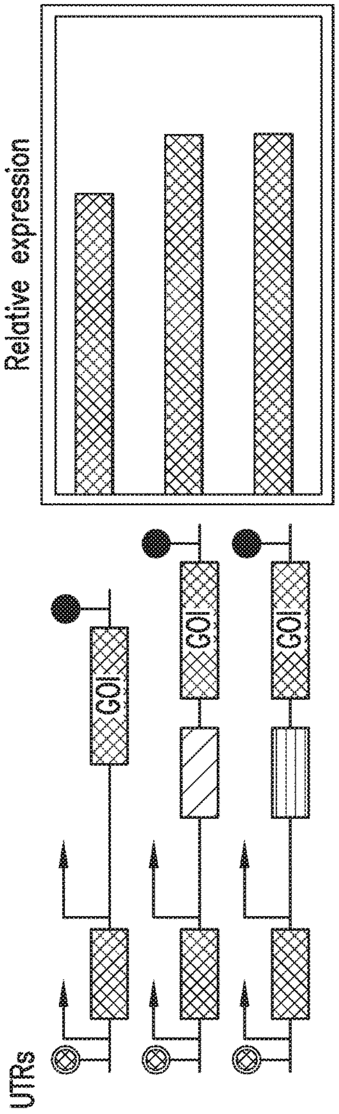

In another embodiment, EESYR cis-acting elements can be assessed using the methods and compositions of the invention. As shown in FIG. 10, EESYR recombinant cells, allows comparison of cis-acting elements equivalently. Because EESYR recombinants behave as a clonal population, differences in gene expression as the result of, for example, the presence or absence of suspected cis-acting elements, can be directly compared. Isogenic cell lines allow direct comparison of cis-acting elements. Using an EESYR system, cis-acting elements, such as, for example, promoters, introns, and UTRs, are preferably located between recombination sites. Expression optimization can also be achieved, including, for example, expression cassette orientation and codon optimization. By way of example, FIGS. 11A-11B show cassettes flanked with recombination recognition sites that contain a promoter, a marker, various cis-elements (here, introns in FIG. 11A; UTRs in FIG. 11B), and a GOI were integrated at an EESYR (SEQ ID NO: 1 at the 5' end, SEQ ID NO:2 at the 3' end). Relative expression of the GOI is shown on the right.

Figure 12A:
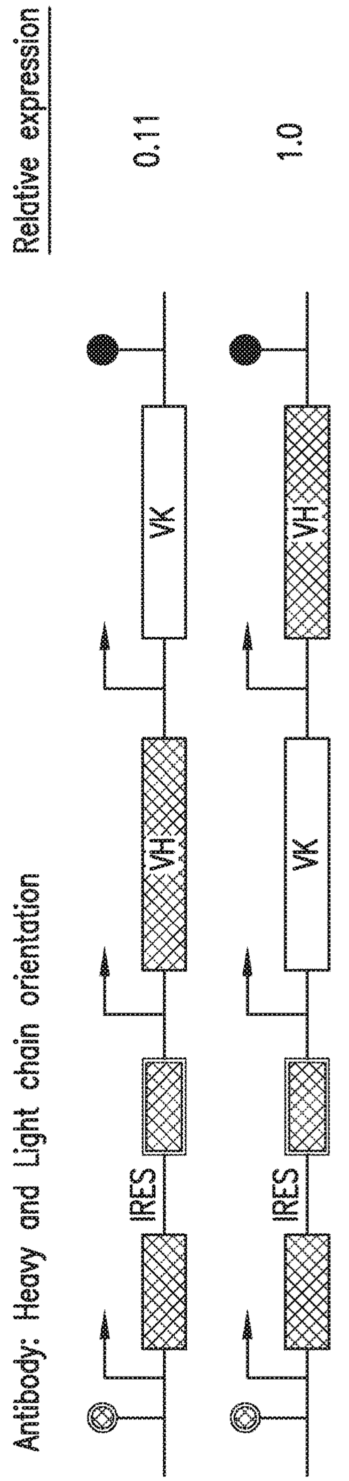
FIGS. 12A-12B illustrate optimizing protein expression using an EESYR system.
Figure 12B:
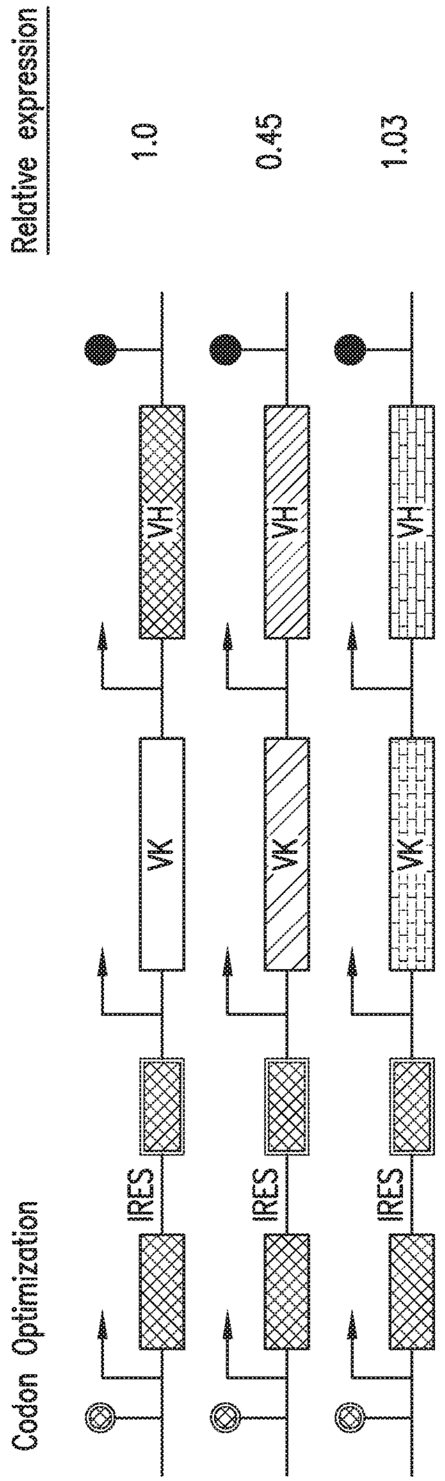

FIGS. 12A-12B show an example of how protein optimization can be achieved using the methods and compositions of the invention. FIGS. 12A-12B confirm that optional placement of a cDNA for a light chain antibody gene is 5' to the cDNA for a heavy chain antibody gene.

Proteins of Interest

A nucleic acid sequence encoding a protein of interest can be conveniently integrated into a cell comprising an EESYR having a recombinase recognition site through, for example, a recombinase-mediated cassette exchange (RMCE) process. Any protein of interest suitable for expression in eukaryotic cells can be used. For example, the protein of interest can be an antibody or fragment thereof, a chimeric antibody or fragment thereof, an ScFv or fragment thereof, an Fc-tagged protein or fragment thereof, a growth factor or a fragment thereof, a cytokine or a fragment thereof, or an extracellular domain of a cell surface receptor or fragment thereof.

Nucleic Acid Constructs

Recombinant expression vectors can comprise synthetic or cDNA-derived DNA fragments encoding a protein, operably linked to a suitable transcriptional and/or translational regulatory element derived from mammalian, viral or insect genes. Such regulatory elements include transcriptional promoters, enhancers, sequences encoding suitable mRNA ribosomal binding sites, and sequences that control the termination of transcription and translation, as described in detail below. Mammalian expression vectors can also comprise nontranscribed elements such as an origin of replication, other 5' or 3' flanking nontranscribed sequences, and 5' or 3' nontranslated sequences such as splice donor and acceptor sites. A selectable marker gene to facilitate recognition of transfectants may also be incorporated.

Transcriptional and translational control sequences in expression vectors useful for transfecting vertebrate cells may be provided by viral sources. For example, commonly used promoters and enhancers are derived from viruses such as polyoma, adenovirus 2, simian virus 40 (SV40), and human cytomegalovirus (CMV). Viral genomic promoters, control and/or signal sequences may be utilized to drive expression, provided such control sequences are compatible with the host cell chosen. Non-viral cellular promoters can also be used (e.g., the β-globin and the EF-1α promoters), depending on the cell type in which the recombinant protein is to be expressed.

DNA sequences derived from the SV40 viral genome, for example, the SV40 origin, early and late promoter, enhancer, splice, and polyadenylation sites may be used to provide other genetic elements useful for expression of a heterologous DNA sequence. Early and late promoters are particularly useful because both are obtained easily from the SV40 virus as a fragment that also comprises the SV40 viral origin of replication (Fiers et al., Nature 273:113, 1978). Smaller or larger SV40 fragments may also be used. Typically, the approximately 250 bp sequence extending from the Hind III site toward the BglI site located in the SV40 origin of replication is included.

Bicistronic expression vectors used for the expression of multiple transcripts have been described previously (Kim S. K. and Wold B. J., Cell 42:129, 1985; Kaufman et al. 1991, supra) and can be used in combination with an EESYR sequence of the invention. Other types of expression vectors will also be useful, for example, those described in U.S. Pat. No. 4,634,665 (Axel et al.) and U.S. Pat. No. 4,656,134 (Ringold et al.).

Host Cells and Transfection

The eukaryotic host cells used in the methods of the invention are mammalian host cells, including, for example, CHO cells and mouse cells. In a preferred embodiment, the invention provides a nucleic acid sequence that encodes an EESYR sequence from CHO cell. An integration site, for example, a recombinase recognition site, can be placed within an EESYR, or 5' or 3' to the EESYR sequence. One example of a suitable integration site is a lox p site. Another example of a suitable integration site is two recombinase recognition sites, for example, a lox p site and a lox 5511 site. In one embodiment, the EESYR sequence is located on chromosome 6 of a CHO cell genome. In specific embodiments, the EESYR sequence is located within a sequence selected from the group consisting of nucleic acids comprising nucleotides 1-6473 and 4607-6473 of SEQ ID NO: 1; and 1-7045, 1-3115, 1-2245, 1-935, and 1-465 of SEQ ID NO:2.

The invention includes a mammalian host cell transfected with an expression vector of the invention. While any mammalian cell may be used, the host cell is preferably a CHO cell.

Transfected host cells include cells that have been transfected with expression vectors that comprise a sequence encoding a protein or polypeptide. Expressed proteins will preferably be secreted into the culture medium, depending on the nucleic acid sequence selected, but may be retained in the cell or deposited in the cell membrane. Various mammalian cell culture systems can be employed to express recombinant proteins. Examples of suitable mammalian host cell lines include the COS-7 lines of monkey kidney cells, described by Gluzman (1981) Cell 23:175, and other cell lines capable of expressing an appropriate vector including, for example, CV-1/EBNA (ATCC CRL 10478), L cells, C127, 3T3, CHO, HeLa and BHK cell lines. Other cell lines developed for specific selection or amplification schemes will also be useful with the methods and compositions provided herein. A preferred cell line is the CHO cell line designated K1. In order to achieve the goal of high volume production of recombinant proteins, the host cell line should be pre-adapted to bioreactor medium in the appropriate case.

Several transfection protocols are known in the art, and are reviewed in Kaufman (1988) Meth. Enzymology 185: 537. The transfection protocol chosen will depend on the host cell type and the nature of the GOI, and can be chosen based upon routine experimentation. The basic requirements of any such protocol are first to introduce DNA encoding the protein of interest into a suitable host cell, and then to identify and isolate host cells which have incorporated the heterologous DNA in a relatively stable, expressible manner.

One commonly used method of introducing heterologous DNA into a cell is calcium phosphate precipitation, for example, as described by Wigler et al. (Proc. Natl. Acad. Sci. USA 77:3567, 1980). DNA introduced into a host cell by this method frequently undergoes rearrangement, making this procedure useful for cotransfection of independent genes.

Polyethylene-induced fusion of bacterial protoplasts with mammalian cells (Schaffner et al., (1980) Proc. Natl. Acad. Sci. USA 77:2163) is another useful method of introducing heterologous DNA. Protoplast fusion protocols frequently yield multiple copies of the plasmid DNA integrated into the mammalian host cell genome, and this technique requires the selection and amplification marker to be on the same plasmid as the GOI.

Electroporation can also be used to introduce DNA directly into the cytoplasm of a host cell, for example, as described by Potter et al. (Proc. Natl. Acad. Sci. USA 81:7161, 1988) or Shigekawa et al. (BioTechniques 6:742, 1988). Unlike protoplast fusion, electroporation does not require the selection marker and the GOI to be on the same plasmid.

More recently, several reagents useful for introducing heterologous DNA into a mammalian cell have been described. These include Lipofectin™ Reagent and Lipofectamine™ Reagent (Gibco BRL, Gaithersburg, Md.). Both of these reagents are commercially available reagents used to form lipid-nucleic acid complexes (or liposomes) which, when applied to cultured cells, facilitate uptake of the nucleic acid into the cells.

A method for amplifying the GOI is also desirable for expression of the recombinant protein, and typically involves the use of a selection marker (reviewed in Kaufman supra). Resistance to cytotoxic drugs is the characteristic most frequently used as a selection marker, and can be the result of either a dominant trait (e.g., can be used independent of host cell type) or a recessive trait (e.g., useful in particular host cell types that are deficient in whatever activity is being selected for). Several amplifiable markers are suitable for use in the expression vectors of the invention (e.g., as described in Maniatis, Molecular Biology: A Laboratory Manual, Cold Spring Harbor Laboratory, N Y, 1989; pgs 16.9-16.14).

Useful selectable markers for gene amplification in drug-resistant mammalian cells are shown in Table 1 of Kaufman, R. J., supra, and include DHFR-MTX resistance, P-glycoprotein and multiple drug resistance (MDR)—various lipophilic cytotoxic agents (e.g., adriamycin, colchicine, vincristine), and adenosine deaminase (ADA)-Xyl-A or adenosine and 2'-deoxycoformycin.

Other dominant selectable markers include microbially derived antibiotic resistance genes, for example neomycin, kanamycin or hygromycin resistance. However, these selection markers have not been shown to be amplifiable (Kaufman, R. J., supra,). Several suitable selection systems exist for mammalian hosts (Maniatis supra, pgs 16.9-16.15). Cotransfection protocols employing two dominant selectable markers have also been described (Okayama and Berg, Mol. Cell Biol 5:1136, 1985).

Useful regulatory elements, described previously or known in the art, can also be included in the nucleic acid constructs used to transfect mammalian cells. The transfection protocol chosen and the elements selected for use therein will depend on the type of host cell used. Those of skill in the art are aware of numerous different protocols and host cells, and can select an appropriate system for expression of a desired protein, based on the requirements of the cell culture system used.

Other features of the invention will become apparent in the course of the following descriptions of exemplary embodiments which are given for illustration of the invention and are not intended to be limiting thereof.

EXAMPLES

The following examples are put forth so as to provide those of ordinary skill in the art how to make and use the methods and compositions described herein, and are not intended to limit the scope of what the inventors regard as their invention. Efforts have been made to ensure accuracy with respect to numbers used (e.g., amount, temperature, etc.) but some experimental error and deviation should be accounted for. Unless indicated otherwise, parts are parts by weight, molecular weight is average molecular weight, temperature is in degrees Centigrade, and pressure is at or near atmospheric.

Example 1. Generation of RGC9 and RGC16 Cell Lines

CHO K1 cells ($1\times10^7$) were infected with pantropic retrovirus produced with plasmid pTE252 (FIG. 1), having a lox p site in it, at an MOI of less than 1 to generate a stable pool of cells with mostly one retroviral insertion per cell. Cells in the stable pool that expressed a marker protein at a high level were selected and expanded. Selection rounds were conducted to identify cell populations capable of enhanced expression. Thirty-six clones were isolated and expanded into 36 cell lines. Clones exhibiting the highest recombination efficiency were identified and cloned, wherein the clones each contained at least one recombinase recognition site in an enhanced expression locus. Eight cell populations with the best recombination efficiency were selected, and reassessed for enhanced protein expression. Two cell populations were selected and designated RGC9 and RGC16. Southern blot analysis of the cell populations from the original 36 cell lines that corresponded to these two cell lines showed that a single copy of a reporter construct was integrated into the CHO cell genome at the same locus in the case of both cell populations, and the location of integration was determined to be at the triplet "act" at nucleotide position 6,471 to 6,473 of SEQ ID NO:5. At least one of these two cell lines were employed in experiments described below.

Example 2. Expression of FcFP1 Protein in Serum-Free Production Medium

RGC38 cells were derived from RGC9 cells and were adapted to grow in suspension in a serum-free production medium. RGC38 cells were used as host cells for the expression of FcFP1 protein (Fc fusion protein-1). RGC38 cells were transfected in a ten-centimeter plate with a FcFP1 expression vector, pTE851 and a Cre plasmid, pRG858. The FcFP1 plasmid has, in 5' to 3' direction, a LoxP site, a SV40 late promoter, a hygromycin resistant gene, an IRES, an eGFP, a CMV MIE promoter, a gene encoding a FcFP1 protein, and a Lox511 site. Cells were cultured in F12 medium with 400 gig/ml hygromycin for two weeks after transfection. Cells expressing eGFP but not DsRed were isolated using flow cytometry and designated as RS421-1. Isolated cells were essentially isogenic, though derived from different founder cells. RS421-1 cells were expanded in suspension cultures in serum-free production medium. FcP1 protein in conditioned medium of 3-day old cultures was examined in SDS-PAGE with Coomassie blue staining. FcF1 protein in the conditioned medium was abundant and could be seen without purification.

Example 3. Regulated Expression of FcFP1 Protein in Serum-Free Production Medium RGC49 cells were derived from RGC16, were adapted to grow in serum-free production medium, and contained a stably integrated tetR-YFP expression plasmid, pcDNA6/TR. The tetR protein allows regulation of transcription from promoters that comprise a tet operator sequence by tetracycline or doxycycline. RGC49 cells were co-transfected with pTE851 and pRG858. The transfected cells were selected with 400 μg/ml hygromycin for two weeks. Cells expressing eGFP but not YFP were isolated using flow cytometry and designated as RS569-1. RS569-1 cells were expanded in suspension cultures in serum-free production medium in the presence or absence of doxycycline. FcP1 protein in conditioned medium of 3-day old cultures was examined by SDS-PAGE and Coomassie blue staining. The RS569-1 cells expressed FcFP1 protein similarly to RS421-1 upon in the presence of 1 μg/ml doxycycline in the culture medium. Very little FcFP1 protein was detected from the RS569-1 cells in the absence of doxycycline.

Example 4. Dual Lox Cell Line Construction

RGC23 cells were derived from RGC16, were adapted to grow in Sigma CHO SSM serum-free medium (Saint Louis, Mo.), and carried DsRed. RGC23 cells were transfected with a Cre plasmid, pRG858 and a eGFP and FcFP2 protein expression vector, pTE357. The FcFP2 vector has, in 5' to 3' direction, a LoxP site, a SV40 late promoter, a hygromycin resistant gene, a CMV MIE promoter, a gene encoding FcFP2 protein, an IRES, an eGFP, and a Lox511 site. Cells expressing both DsRed and eGFP were collected and a single cell was isolated. The isolated cell was expanded in culture, and the resulting cell line was designated RS398-2-6. RS398-2-6 was then transfected with pRG858 (Cre plasmid) and pRG1231, a eCFP expression plasmid. pRG1231 has, in 5' to 3' direction, a LoxP site, a CMV MIE promoter, a puromycin resistant gene, an IRES, an eCFP, and a Lox511 site. Cells expressing DsRed and eCFP but not eGFP were isolated by flow cytometry as a pool and designated as RS630.

Example 5. Antibody Heavy Chain and Light Chain Expression Using a Dual Lox Cell Line RS630 cells were transfected with pTE828, a 15G1 antibody heavy chain and eGFP expression vector, pTE829, a 15G1 antibody light chain and eYFP expression vector, and pRG858. pTE828 has, in 5' to 3' direction, a LoxP site, a SV40 late promoter, a hygromycin resistant gene, an IRES, an eGFP, a CMV MIE promoter, the heavy chain gene of 15G1 antibody, and a Lox511 site. pTE829 has, in 5' to 3' direction, a LoxP site, a SV40 late promoter, a neomycin resistant gene, an IRES, an eYFP, a CMV MIE promoter, the light chain gene of 15G1 antibody, and a Lox511 site. The transfected cultures were selected with hygromycin and G418 at 400 μg/ml each for two weeks. Cells expressed both YFP and eGFP but neither dsRed nor eCFP were isolated by flow cytometry. The isolated cells were expanded in suspension culture in serum-free production medium and were designated as RS631 cells. Aliquots of conditioned medium from 3-day old culture were analyzed by SDS-PAGE. The antibody products from RS631 cells were readily detected by Coomassie blue staining.

Example 6. Use of a Third Lox Site (Lox2272) at EESYR to Create Dual Expression Cassette Cells from any cell line carrying a DsRED gene flanked by a LoxP site and a Lox511 site at EESYR locus are transfected with pRG858 and a vector comprising, in 5' to 3' direction, a LoxP site, a first promoter, a YFP, a Lox2272 site, a second promoter, an eGFP, and a Lox511. Cells expressing eGFP and YFP, but not DsRed are isolated. Isolated cells are then transfected with pRG858, pRG1167 (a vector that has, in 5' to 3' direction, a LoxP site, a SV40 late promoter, a hygromycin resistant gene, a CMV MIE promoter, a DsRed and a Lox2272 site) or pRG1234 (a vector that has, in 5' to 3' direction, a Lox2272 site, a SV40 late promoter, a hygromycin resistant gene, a CMV MIE promoter, a DsRed and a Lox511 site). Cells capable of expressing either DsRED and eGFP but not YFP, or DsRED and YFP but not eGFP, are isolated.

Example 7. Antibody Expression from RGC38 Host Cells

RGC38 cells were transfected with pTE963 and pRG858. pTE963 has, in 5' to 3' direction, a LoxP site, a SV40 late promoter, a hygromycin resistant gene, an IRES, an eGFP, a CMV MIE promoter, the light chain gene of 15G1 antibody, a CMV MIE promoter, the heavy chain gene of 15G1 antibody, and a Lox511 site. The transfected cultures were selected with hygromycin at 400 μg/ml each for two weeks. Cells that expressed eGFP but not dsRed were isolated by flow cytometry. The isolated cells were expanded in suspension in serum-free production medium and were named as RS533 cells. For the production of 15G1 antibodies, RS533 cells were cultured in a bioreactor for 10 days. Aliquots of spent medium from day six to day ten were collected and their protein composition was analyzed by SDS-PAGE. The heavy chain and light chain peptide of the 15G1 antibody in the reactor spent medium were readily detected by Coomassie blue staining.

Example 8. Rescuing and Subcloning EESYR Sequences

A CHO cell line (designated RGC21) expressing high levels of a reporter gene, DsRed, was selected for isolation of EESYR sequences, since Southern blot analysis indicated that the high expression of DsRed expression observed for this cell line is driven by a single integration of an expression cassette encoding DsRed. Genomic sequences 5' to the expression cassette were rescued by transfecting RGC21 cells with linearized pTE494 plasmids, a vector that has, in 5' to 3' direction, a LoxP site, an ampicillin resistance gene, a bacterial origin or replication, a CMV MIE promoter, a neomycin phosphotransferase gene, an IRES, an eGFP and a Lox511 site. Cells expressing eGFP but not DsRed were isolated by flow cytometry as a pool. Genomic DNA was isolated, digested with XbaI restriction endonuclease, and self ligated to create pRG1106. Genomic sequences 3' to the expression cassette were rescued by transfecting RGC21 cells with circular pTE495 plasmids, a vector that has, in 5' to 3' direction, a LoxP site, a CMV MIE promoter, a neomycin phosphotransferase gene, an IRES, an eGFP, a bacterial origin or replication, an ampicillin resistance gene, and a Lox511 site. Cells expressing eGFP but not DsRed were isolated by flow cytometry as a pool. Genomic DNA was isolated, digested with MfeI restriction endonuclease, and self ligated to create pRG1099.

Example 9. Plasmid Construction for EESYR Analysis

EESYR sequences were excised from either pRG1106 or pRG1099 as AgeI fragments and inserted into the AgeI and NgoMIV sites of pTE575, a plasmid expressing FCFP2, to yield plasmid pTE809. The pTE575 plasmid has, in 5' to 3' direction, a SV40 late promoter, a hygromycin resistant gene, a CMV MIE promoter, and a gene encoding FCFP2 protein. In stably transfected CHO cells, pTE809 and pTE575 yielded 97.22% and 38.57% of cells expressing detectable levels of FCFP2 protein, respectively. The mean fluorescence of FcFP2 detected by an FITC conjugated antibody was 482.54 and 279.75 for cultures transfected with pTE809 and pTE575, respectively. Thus, the inclusion of EESYR in expression vectors increased the expression of FCFP2 protein in stable transfection.

The present invention may be embodied in other specific embodiments without departing from the spirit or essence thereof.

We claim:

1. An isolated cell comprising at least one exogenous nucleic acid integrated within, or adjacent to the 5' or 3' end of, an expression-enhancing expression and stability region (EESYR) sequence in the genome, wherein the EESYR sequence is at least 90% identical to SEQ ID NO: 6 and enhances expression of an exogenous gene integrated within, or adjacent to the 5' or 3' end of, the EESYR sequence by at least 1.5 fold over random integration of the exogenous gene.

2. The isolated cell of claim 1, wherein the EESYR sequence is SEQ ID NO: 6.

3. The cell of claim 2, wherein the at least one exogenous nucleic acid comprises at least one of an integration site and a first gene of interest (GOI).

4. The cell of claim 2, wherein the exogenous nucleic acid is introduced into or adjacent to the EESYR sequence by homologous recombination, site-directed integration, random mutagenesis, integrase technology, or through the action of a recombinase.

5. The cell of claim 3, wherein the integration site is a recombinase recognition site.

6. The cell of claim 5, wherein the recombinase recognition site is selected from the group consisting of a LoxP site, a Lox511 site, a Lox2272, and a Frt site.

7. The cell of claim 3, wherein a first gene of interest (GOI) is immediately adjacent to an integration site.

8. The cell of claim 3, wherein the first GOI encodes a protein selected from the group consisting of an immunoglobulin or an antigen-binding fragment thereof, an Fc fusion protein, and a receptor or ligand-binding fragment thereof.

9. The cell of claim 8, wherein the first GOI encodes a protein selected from the group consisting of an antibody light chain or antigen-binding fragment thereof, an antibody heavy chain or antigen-binding fragment thereof, and an Fc fusion protein.

10. The cell of claim 7, wherein the first GOI is immediately adjacent and 5' of a first recombinase recognition site, and immediately adjacent and 3' of a second recombinase recognition site.

11. The cell of claim 8, further comprising a second GOI immediately adjacent and 3' of the second recombinase recognition site.

12. The cell of claim 11, further comprising a third recombinase recognition site immediately adjacent and 3' of the second GOI.

13. The cell of claim 3, further comprising at least one marker gene.

14. The cell of claim 13, wherein the at least one marker gene is selected from the group consisting of a drug resistance gene and an expression reporter gene.

15. The cell of claim 3, wherein the first GOI is operably linked to a promoter.

16. The cell of claim 11, further comprising a promoter operably linked to the first GOI and a promoter operably linked to the second GOI.

17. The cell of claim 16, wherein the first GOI encodes a light chain of an antibody and the second GOI encodes a heavy chain of an antibody.

18. The cell of claim 16, wherein the first GOI encodes a heavy chain of an antibody and the second GOI encodes a light chain of an antibody.

19. The cell of claim 12, wherein the second and the third recombinase recognition sites are in an orientation opposite to the first recombinase recognition site.

20. The cell of claim 12, wherein the first, second, and third recombinase recognition sites are different.

21. The cell of claim 15, wherein the promoter is operably linked to an operator.

22. The cell of claim 21, wherein the promoter comprises a eukaryotic promoter, and the eukaryotic promoter is operably linked to a prokaryotic operator.

23. A method for making a protein of interest (POI), comprising: (a) providing a cell comprising an exogenous nucleic add integrated within, or adjacent to the 5' or 3' end of, an expression-enhancing expression and stability region (EESYR) sequence in the genome, wherein the EESYR sequence is at least 90% identical to SEQ ID NO: 6 and enhances expression of an exogenous gene integrated within, or adjacent to the 5' or 3' end of, the EESYR sequence by at least 1.5 fold over random integration of the exogenous gene, wherein the exogenous nucleic add encodes the POI; (b) culturing the cell of under conditions that allow expression of the POI; and; (c) recovering the POI.

24. The method of claim 23, wherein the EESYR sequence is SEQ ID NO: 6.

25. The method of claim 24, wherein the POI is selected from the group consisting of an immunoglobulin or an antigen-binding fragment thereof, an Fc fusion protein, and a receptor or ligand-binding fragment thereof.

26. The method of claim 24, wherein the POI is selected from the group consisting of an antibody light chain or antigen-binding fragment thereof, an antibody heavy chain or antigen-binding fragment thereof, and an Fc fusion protein.

* * * * *

SEQUENCE LISTING

```
<160> NUMBER OF SEQ ID NOS: 20

<210> SEQ ID NO 1
<211> LENGTH: 6473
<212> TYPE: DNA
<213> ORGANISM: Cricetulus griseus

<400> SEQUENCE: 1

tctagaaaca aaaccaaaaa tattaagtca ggcttggctt caggtgctgg ggtggagtgc      60

tgacaaaaat acacaaattc ctggctttct aaggcttttt cggggattca ggtattgggt     120

gatggtagaa taaaaatctg aaacataggt gatgtatctg ccatactgca tgggtgtgta     180

tgtgtgtgta tgtgtgtctg tgtgtgtgcc cagacagaaa taccatgaag gaaaaaaaca     240

cttcaaagac aggagagaag agtgacctgg gaaggactcc ccaatgagat gagaactgag     300

cacatgccag aggaggtgag gactgaacca ttcaacacaa gtggtgaata gtcctgcaga     360

cacagagagg gccagaagca ctcagaactc cagggggtca ggagtggttc tctggaggct     420

tctgcccttg gaggttcctg aggaggaggc ttccatattg aaaatgtagt tagtggccgt     480

ttccattagt acagtgacta gagagagctg agggaccact ggactgaggc ctagatgctc     540

agtcagatgg ccatgaaagc ctagacaagc acttccgggt ggaaaggaaa cagcaggtgt     600

gaggggtcag gggcaagtta gtgggagagg tcttccagat gaagtagcag gaacggagac     660

gcactggatg gccccacttg tcaaccagca aaagcttgga tcttgttcta agaggccagg     720

gacatgacaa gggtgatctc ggtttttaaa aggctttgtg ttacctaatc acttctatta     780

gtcagatact ttgtaacaca aatgagtact tggcctgtat tttagaaact tctgggatcc     840

tgaaaaaaca caatgacatt ctggctgcaa cacctggaga ctcccagcca ggccctggac     900

ccgggtccat tcatgcaaat actcagggac agattcttca ctaggtactg atgagctgtc     960

ttggatgcaa atgtggcctc ttcattttac tacaagtcac catgagtcag gaggtgctgt    1020

ttgcacagtg tgactaagtg atggagtgtt gactgcagcc attcccggcc ccagcttgtg    1080

agagagatcc ttttaaattg aaagtaagct caaagttacc acgaagccac acatgtataa    1140
```

-continued

```
actgtgtgaa taatctgtgc acatacacaa accatgtgaa taatctgtgt acatgtataa   1200
actgtgtgaa taatctgtgt gcagcctttc cttacctact accttccagt gatcaggttt   1260
ggactgcctg tgtgctactg gaccctgaat gtccccaccg ctgtcccctg tcttttacga   1320
ttctgacatt tttaataaat tcagcggctt cccctctgct ctgtgcctag ctataccttg   1380
gtactctgca ttttggtttc tgtgacattt ctctgtgact ctgctacatt ctcagatgac   1440
atgtgacaca gaaggtgttc cctctggaga catgtgatgt ccctgtcatt agtggaatca   1500
gatgccccca aactgttgtc cagtgtttgg gaaagtgaca cgtgaaggag gatcaggaaa   1560
agaggggtgg aaatcaagat gtgtctgagt atctcatgtc cctgagtggt ccaggctgct   1620
gacttcactc cccaagtga gggaggccat ggtgagtaca cacacctcac acatactata    1680
tccaacacac acacacacac acacacacac acgcacgcac gcacgcacgc acgcacacat   1740
gcacacacac gaactacatt tcacaaacca catacgcata ttacacccca aacgtatcac   1800
ctatacatac cacacataca caccccctcca cacatcacac acataccaca cccacacaca  1860
gcacacacat acataggcac acattcacac accacacata tacatttgtg tatgcataca   1920
tgcatacaca cacaggcaca cagacaccac acacatgcat tgtgtacgca cacatgcata   1980
cacacacata ggcacacatt gagcacacac atacatttgt gtacgcacac tacatagaca   2040
tatatgcatt tgtatatgca cacatgcatg cacacataca taggcacaca tagagcacac   2100
acatacattt gtgtatgcac acatgcacac accaatcaca tgggaagact caggttcttc   2160
actaaggttc acatgaactt agcagttcct ggttatctcg tgaaacttgg aagattgctg   2220
tggagaagag gaagcgttgg cttgagccct ggcagcaatt aaccccgccc agaagaagta   2280
ggtttaaaaa tgagagggtc tcaatgtgga acccgcaggg cgccagttca gagaagagac   2340
ctacccaagc caactgagag caaaggcaga gggatgaacc tgggatgtag tttgaacctc   2400
tgtaccagct gggcttcatg ctattttgtt atatctttat taaatattct tttagtttta   2460
tgtgcgtgaa taccttgctt gcataaatgt atgggcactg tatgtgttct tggtgccggt   2520
ggaggccagg agagggcatg gatcctccgg agctggcgtt tgagacagtt gtgacccaca   2580
gtgtggggtc tgggaactgg gtcttagtgt tccgcaagtg cagctggggc tcttaacctc   2640
tgagccatcc ctccagcttc aagaaactta ttttcttagg acatggggga agggatccag   2700
ggctttaggc ttgtttgttc agcaaatact cttttcgtgt attttgaatt ttattttatt   2760
ttactttttt gggatagaat cacattctgc agctcaggct gggcctgaac tcatcaaaat   2820
cctcctgtct cagtctacca ggtgataaga ttactgatgt gagcctggct ttgacaagca   2880
ctttagagtc cccagccctt ctggacactt gttccaagta taatatatat atatatatat   2940
atatatatat atatatatat atatattgtg tgtgtgtgtt tgtgtgtgta tgagacactt   3000
gctctaaggg tatcatatat atccttgatt tgcttttaat ttattttttta attaaaaatg  3060
attagctaca tgtcacctgt atgcgtctgt atcatctata tatccttcct tccttctctc   3120
tctttctctc ttcttcttct cacccccaag catctatttt caaatccttg tgccgaggag   3180
atgccaagag tctcgttggg ggagatggtg agggggcgat acaggggaag agcaggagga   3240
aagggggaca gactggtgtg ggtctttgga gagctcagga gaatagcagc gatcttccct   3300
gtccctggtg tcacctctta cagccaacac cattttgtgg cctggcagaa gagttgtcaa   3360
gctggtcgca ggtctgccac acaaccccaa tctggcccca agaaaaggca cctgtgtgtg   3420
actctggggt taaaggcgct gcctggtcgt ctccagctgg acttgaaact cccgtttaat   3480
aaagagttct gcaaaataat acccgcagag tcacagtgcc aggttcccgt gctttcctga   3540
```

```
agcgccaggc acgggttccc taggaaatgg ggccttgctt gccaagctcc cacggcttgc   3600
cctgcaaacg gcctgaatga tctggcactc tgcgttgcca ctgggatgaa atggaaaaaa   3660
gaaaaagaag aagtgtctct ggaagcgggc gcgctcacac aaacccgcaa cgattgtgta   3720
aacactctcc attgagaatc tggagtgcgg ttgccctcta ctggggagct gaagacagct   3780
agtgggggcg gggggaggac cgtgctagca tccttccacg gtgctcgctg gctgtggtgc   3840
atgccgggaa ccgaaacgcg gaactaaagt caagtcttgc tttggtggaa ctgacaatca   3900
acgaaatcac ttcgattgtt ttcctctttt tactggaatt cttggatttg atagatgggg   3960
gaggatcaga gggggagggg aggggcgggg agacggaggg aggaggggag gaggggagga   4020
ggggaggagg ggaggagggg aagggatgga ggaaaatact aacttttcta attcaacatg   4080
acaaagattc ggagaaagtg caccgctagt gaccgggagg aggaatgccc tattgggcat   4140
tatattccct gtcgtctaat ggaatcaaac tcttggttcc agcaccaagg attctgagcc   4200
tatcctattc aagacagtaa ctacagccca cacggaagag gctatacaac tgaagaaata   4260
aaattttcac tttatttcat ttctgtgact gcatgttcac atgtagagag ccacctgtgt   4320
ctaggggctg atgtgctggg cagtagagtt ctgagcccgt taactggaac aacccagaac   4380
tcccaccaca gttagagctt gctgagagag ggaggccctt ggtgagattt ctttgtgtat   4440
ttatttagag acagggtctc atactgtagt ccaagctagc ctccagctca cagaaattct   4500
cctgttccgg tttccaaagt actggagtta tgagtgtgtg ttaattgaac gctaagaatt   4560
tgctgattga agaaaacctc aagtgggttt ggctaatccc cacgacccca gaggctgagg   4620
caggaggaat gagagaattc aaggtttgcc agagccacag ggtgagctca atgtggagac   4680
tgtgagggtg agctcaatgt ggagactgtg agggtgagct caatgtggag actgtgaggg   4740
tgagctcaat gtggagactg tgagggtgag ctcaatgtgg agactgtgag ggtgagctca   4800
atgtggagac ctgtatcaag ataataatag tagtagtaac aatgcaggcg agggtgtggt   4860
tgagtggtag agcagttagt tgatttgaca tgcttgaggt ctcccggtcc atctgtggcc   4920
ctgcaacagg aagggaggga ggaagggggg gaacgagaga gaggaaagag agacagaagc   4980
taagataggg aatgagagag gaaggaagaa acgggaagaa attcagactc cttcctgagt   5040
tccgccaacg cctagtgaca tcctgtgcac accctaaggt ggcctttgtg tggcactggc   5100
ttgggtggtc gggaaaggca ttttcagctt gttgcagaac tgccacagta gcatgctggg   5160
tccgtgaaag tttctgcccg ttaacaagaa gtctctacta cttgtgacct caccagtgaa   5220
aatttcttta attgtctcct ggtgttctgg gttttgcatt tttgtttcta aggatacatt   5280
cctgggtgat gtcatgaagt ccccaaagac acagtggggc tgtgttggat tgggaaagat   5340
gatttatctg ggtgtcaaa aggaaaagaa gggaaacagg cacttgggaa aatgtcctcc   5400
cgcccacccg aattttggct tggcaaccgt ggtggaggag caagaaacac gtggacgttt   5460
gaggaggcat ggggtcctag gaggacagga agcagaagga gagagctggg ctgacagcct   5520
gcaggcattg cacagtttca gaaggagatt acagcatgac tgagtttta gggatccaac   5580
agggacctgg gtagagattc tgtgggctct gaggcaactt gacctcagcc agatggtatt   5640
tgaataacct gctcttagag ggaaaacaga catagcaaac agagccacgt ttagtgatga   5700
aactctcact ttgcctgagt catgtgcggc catgcccagg ggtcaggctg acactcaact   5760
caaaaacaag tgagaaattg aagacaatcc gtggtggcag ctactggaag ggccaccaca   5820
tccccagaaa gagtggagct gctaaaaagc catttgtgat aggcacagtt atcttgaatg   5880
```

-continued

```
catggagcag agattacgga aaaatcgaga atgttaatga ggcaacattc gagttgagtc   5940

attcagtgtg ggaaacccag acgcttccat cccctaaaag gaacatcttg ctctcagtca   6000

aaatggaaat aaaaattggg gcttgaattt ggcaaatgat tcagaactct gtgtaggtat   6060

tttcacacgc acagtggata attttcatgt tggagtttat ttgtgctaaa aggcagaaaa   6120

gggtaaaaag cacatcttaa gagttatgag gttctacgaa taaaaataat gttacttaca   6180

gctattcctt aattagtacc cccttccacc tgtggtaatt tcctgagata gtcagtgggg   6240

aaaagatctc tccttctctt ctttctcccc ctcccctcct ctccctccct ccctccctcc   6300

ctccctcctc tccctccctc cccctttcct tctttctttg ctccttctcc tctgcctcct   6360

tctccctttc ttcttcattt attctaagta gcttttaaca gcacaccaat tacctgtgta   6420

taacgggaaa acacaggctc aagcagctta gagaagattg atctgtgttc act          6473
```

<210> SEQ ID NO 2
<211> LENGTH: 7045
<212> TYPE: DNA
<213> ORGANISM: Cricetulus griseus

<400> SEQUENCE: 2

```
actagcgtgc aattcagagg tgggtgaaga taaaaggcaa acatttgagg ccatttcctt     60

atttggcacg gcacttagga agtggaacat gcctaatcta ctggtttgta ccacctttcc    120

ctataatgga ctgtttggga agctcctggg caaccgattc tggcatctca ttggtcagag    180

gcctgttaaa tggtactctt atttgcaaag aaggctgtaa cttgtagctt taaaagcctc    240

tcctcaagaa agaagggaga aaggatatgg ctagacatat ctaatagact taaccactgt    300

gaaaagcctt agtatgaatc agatagaacc tatttttaac tcagttttga aaaaaataat    360

ctttatattt atttgtgtgt gtgtgtgtgt gtgtgtgtgt gtgtgtgtgt gtgtgtgtgt    420

gaaccacatg tagcaggtgc tggaggaggc cagaagaggg caccagatct cctggaactg    480

acaccacaca tggttatgag ctgcctgatg tgggtgctgg gaactgaact ctcgtgttct    540

gcaagagcag caactgttct cttaactgat gagccatctc tccagccccc cccataattt    600

taattgttca ttttagtaaa ttttattcat aatcaattat cacagtataa aacaatgatt    660

ttatatatat catatacata tcaaggatga cagtgagggg gatatgtgtg tgtgtgtgtg    720

tgtgtgtgtg tgtgtgtgtg tgtgttattt gtgtgtgtgc tttttaagaa ggtgccatag    780

tcactgcatt tctctgaagg atttcaaagg aatgagacat gtctgtctgc caggaaccct    840

atcttcctct ttgggaatct gacccaaatg aggtattctg aggaactgaa tgaagagctc    900

aagtagcagt gtcttaaacc caaatgtgct gtctagagaa agtcaacgtc atcagtgagc    960

tgaggagaga tttactgagc ggaagacaag cgctctttga tttaagtggc tcgaacagtc   1020

acggctgtgg agtggagcct gtgctcaggt ctgaggcagt ctttgctagc cagctgtgat   1080

gagcagtgaa gaaagggtgg agatggaggc agggtgggag cagggctatg gttcagacta   1140

ggtatcgtga gcacaccagc tggttgactt gtggtctgtg ggtcaggcgt tgtaaacgcc   1200

ctcagggtca ggcagtcaca ttgcttgaag ctgaatgggt gaggcaacac agagagtgca   1260

aagaaggcaa agtaccacct cttccccgac ccaggtcact tctgggttat agctgagact   1320

ccggacagca tgcaaccagc tggttagagc ttcagggaaa acttgatgtc tgcatgttgc   1380

tatgaaatgt gattcggtac atctggagaa aatttataat gctggctcag tcaagcactg   1440

aacaaaggta ccttggcttt gggagctaca tgacattgac ttgtaggcag actttttttt   1500

ttctgcccgc caattcccag ataaccaata tggaggctca atattaatta taaatgctcg   1560
```

-continued gctgatagct caggcttgtt actagctaac tcttccaact taaatgaacc catttctatt 1620
atctacattc tgccacgtga ctttaccttg tacttcctgt ttcctctcct tgtctgactc 1680
tgcccttctg cttcccagag tccttagtct ggttctcctg cctaacctta tcctgcccag 1740
ctgctgacca agcatttata attaatatta agtctcccag tgagactctc atccagggag 1800
gacttgggtg ctccccccctc ctcattgcca tccgtgtctt cctcttccct cgcttccccc 1860
tcctcttcct gctcttcctc ctccacccct cctttcatag tattgatggc aagggtgttc 1920
tagaatggag gagtgcccat aggcatgcaa agaaaccagt taggatgctc tgtgaggggt 1980
tgtaatcata agcgatggac acaattcaag ccacagagtg aagacggaag gatgcactgt 2040
gctctagagc aacttctggg gcagaatcac agggtgagtt tctgacttga gggcgaagag 2100
gccacgagga agggagtgag tttgtctgag ctagaagcta cggcccacct cttggtagca 2160
gacctgccca caagcatgct ttgttaatca tgtgggatct gattttcctc taaatctatg 2220
ttcaactctt aagaaaatgt gaattctcac attaaaattt agatatacgt cttttggtgg 2280
ggggggtgta aaaaatcctc aagaatatgg atttctgggg gccggagaga tggctcagag 2340
gttaagagaa ctggttgctc ttctagacat tctgagttca attcccagca accacatggt 2400
ggctcacaac catctgtaat gcgacctggt gccatcttct gacatgcatg gatacatgca 2460
ggcagaaagc tgtatacata gtaaattgat aaatcttttt ttaaaaagag tatggattct 2520
gccgggtgtt ggtggcgcac gcctttaatc ccagcactct ggaggcagag gcaggtggat 2580
ctctgtgagt tcgagaccag cctggtctat aagagctagt tccaggacag cctccaaagc 2640
cacagagaaa ccctgtctcg aaaaaccaaa aaaaaaaaaa aaaaaaaaaa aaaaaaaaga 2700
gtatggattc taagaaagcc gtaacagctg gagctgtgta cggagttcag cgtggtacta 2760
gaagaacaga cattcatgat gaaacacccc aggattttta cttagtatct agtttccatt 2820
gttgttttga gaccggctct tatgctctcc aggctggcct caaactgctg atcttcccgc 2880
ctctacctct caagtcctgg gactacttgg ctcataaaac agtttttgtc gggctccctg 2940
aagttatggt tgtacaaacc gtgggggtca atatactcac ttgggcagag agagaaggtc 3000
tgaatcccag acaatgactg catctcagga cagttgggaa gaggacaatg gcagaaggac 3060
ttagaaaaga tagactggag ggtggaaaag cagcaggaac agagaaacaa aacaggaagc 3120
ttgctatcca gggccactct ggagtcctgt ggcaagatgg aagcgggcta ggggaataca 3180
tttgtgctac tgtgtgtgtg tgtgtgtgtg tgtgtgtgtg tgtgtgtgat caatgcctat 3240
caatgttgaa ggggaaatat gtataccaca ttgattctgg gagcaattct cagtatctgg 3300
cctagagaaa ggaatggccc ctgcagaata gacagagtga atggtgccct ttatcatttg 3360
ctaaagtgaa ggagaaataa acatccttcc atagagtttc aggtaaatga accccacagt 3420
tcatctgtgc cgtggtggag gcctggccaa cagttaaaaa gattagacac ggacaaagtc 3480
tgaaggaaac acctcgaata ggaagaggag agccacctca ttctgtaact ttcctcaagg 3540
ggaagatgtt ccaagagtgg gaataaatgg tcaaaggggg gatttttaat taggaaaacg 3600
atttcctgta tcacttgtga aactggaggt tgatttgggg cataggacaa tagatttgat 3660
gctttgcaaa aagctgtttc aaagcagaga aatggaatag agacaattat gtagcgagga 3720
gggagggtgg ggcgaagatg gagacagaga agtggaagct gactttaggg aagaggaaca 3780
tagaccacag gggcggggcg gggggcaggg gcggggggcg gggctcaaag gaggcagtgg 3840
gaacgttgct agtgttcgca gcgtaagcgt gaatgtgcaa gcgtctttgt ggtgtgtgac 3900

-continued

```
caggagtagc gtggctggct tgtgtgctgc ttgtaatccc agtctttgag gtttccacac   3960
tgttccacag tgggtgtgat tttccctcgg agagcatgag ggctctgctt tccccacatc   4020
ctccccagcg ttcgttggta tttgtttcca agatgttagt gggtgagaca aagcctctct   4080
gttgatttgc ctttaacagg tgacaaaaaa agctcaacca ggagacattt ttgccttctt   4140
ggaaggtaat gctcccatgt agagcaatgg gacccatctc taaggtgagg ctactcttgc   4200
agtttgcacc cagctcttct gatgcaggaa ggaagttggt gggcaagcaa gactgtttgc   4260
ttcttgcgat ggacacattc tgcacacaaa ggctcaggag gggagaaggc tgtttgatgt   4320
ttagcactca ggaaggcccc tgatgcatct gtgattagct gtctccatct gtggagcaga   4380
cacggactaa ctaaaaacca gtgtttttaa attgtcaagc ctttaaggtg aggaaattga   4440
cttattgtgc tgggccatac gtagagcaag tgctctgcat tgggccaacc cccggctctg   4500
gtttctaggc accagaatgg cctagaacta actcacaatc ctcccattcc aggtctcagg   4560
tgctagaatg aaccactata ccagcctgcc tgcctgccta cctgccttcc taaattttaa   4620
atcatgggga gtaggggaga atacacttat cttagttagg gtttctattg ctgtgaagag   4680
acaccatgag catggcaact cttataaagg aaaacattta gttgggtggc agtttcagag   4740
gttttagtac attgtcatca tggctgggaa catgatggca tgcagacaga catggtgctg   4800
gagaaaggga tgagagtcct acatcttgca ggcaacagga cctcagctga gacactggct   4860
ggtaccctga gcataggaaa cctcacagcc caccctcaca gtgacatatt tccttcaaca   4920
aagccatacc tcctaatagt gccactccct atgagatgac agggccaatt acattcaaac   4980
tgctataaca ctttaaagta ttttattttt attattgtaa attatgtatg tagctgggtg   5040
gtggcagccg aggtgcacgc ctttaatccc agcacttggg aggcagaggc agatggatct   5100
ctgtgagttc aagaccagcc tggtctataa gagctagttg caaggaagga tatacaaaga   5160
acagttctag gatagccttc aaagccacag agaagtgctg tcttgaaaac caaaaattgt   5220
gctgggacct gtctctgctt tggttgcttc ccactccccc agagctggac tcttggtcaa   5280
cactgaatca gctgcaaaat aaactcctgg attcctctct tgtaacagga gcccgaagtc   5340
aggcgcccac ttgtcttctc gcaggattgc catagacttt ttctgtgtgc ccaccattcc   5400
agactgaagt agagatggca gtggcagaga ctgggaaggc tgcaacgaaa acaggaagtt   5460
attgcaccct gggaatagtc tggaaatgaa gcttcaaaac ttgcttcatg ttcagttgta   5520
cacagactca ctcccaggtt gactcacacg tgtaaatatt cctgactatg tctgcactgc   5580
ttttatctga tgcttccttc ccaaaatgcc aagtgtacaa ggtgagggaa tcacccttgg   5640
attcagagcc cagggtcgtc ctccttaacc tggacttgtc tttctccggc agcctctgac   5700
acccctcccc ccattttctc tatcagaagg tctgagcaga gttggggcac gctcatgtcc   5760
tgatacactc cttgtcttcc tgaagatcta acttctgacc cagaaagatg gctaaggtgg   5820
tgaagtgttt gacatgaaga cttggtctta agaactggag caggggaaaa aagtcggatg   5880
tggcagcatg tacccgaaat cccagaactg gggaggtaga gacggatgag tgcccggggc   5940
tagctggctg ctcagccagc ctagctgaat tgccaaattc caactcctat tgaaaaacct   6000
ttaccaaaca aacaaacaaa caaataataa caacaacaac aacaacaaac taccccatac   6060
aaggtgggcg gctcttggct cttgaggaat gactcaccca aacccaaagc ttgccacagc   6120
tgttctctgg cctaaatggg gtgggggtgg ggcagagaca gagacagaga gagacatgac   6180
ttcctgggct gggctgtgtg ctctaggcca ccaggaactt tcctgtcttg ctctctgtct   6240
ggcacagcca gagcaccagc acccagcagg tgcacacacc tccctccgtg cttcttgagc   6300
```

-continued aaacacaggt gccttggtct gtctattgaa ccggagtaag ttcttgcaga tgtatgcatg 6360
gaaacaacat tgtcctggtt ttatttctac tgttgtgata aaaaccgggg aactccagga 6420
agcagctgag gcagaggcaa atgcaaggaa tgctgcctcc tagcttgctc cccatggctt 6480
gccgggcctg ctttctgcaa gcccttctct ccccattggc atgcctgaca tgaacagcgt 6540
ttgaaatgct ctcaaatgtc actttcaaag aaggcttctc tgatcttgct aactaaatca 6600
gaccatgttt caccgtgcat tatctttctg ctgtctgtct gtctgtctgt ctgtctatct 6660
gtctatcatc tatcaatcat ctatctatct atcttctatt tatctaccta tcattcaatc 6720
atctatcttc taactagtta tcatttattt atttgtttac ttactttttt tatttgagac 6780
agtatttctc tgagtgacag ccttggctgt cctggaaccc attctgtaac caggctgtcc 6840
tcaaactcac agagatccaa ctgcctctgc ctctctggtg ctggggttaa agacgtgcac 6900
caccaacgcc ccgctctatc atctatttat gtacttatta ttcagtcatt atctatcctc 6960
taactatcca tcatctgtct atccatcatc tatctatcta tctatctatc tatctatcta 7020
tctatcatcc atctataatc aattg 7045

<210> SEQ ID NO 3
<211> LENGTH: 6473
<212> TYPE: DNA
<213> ORGANISM: Cricetulus griseus

<400> SEQUENCE: 3
agtgaacaca gatcaatctt ctctaagctg cttgagcctg tgttttcccg ttatacacag 60
gtaattggtg tgctgttaaa agctacttag aataaatgaa gaagaaaggg agaaggaggc 120
agaggagaag gagcaaagaa agaaggaaag ggggagggag ggagaggagg gagggaggga 180
gggagggagg gagaggaggg gagggggaga aagaagagaa ggagagatct tttccccact 240
gactatctca ggaaattacc acaggtggaa gggggtacta attaaggaat agctgtaagt 300
aacattattt ttattcgtag aacctcataa ctcttaagat gtgcttttta cccttttctg 360
ccttttagca caaataaact ccaacatgaa aattatccac tgtgcgtgtg aaaataccta 420
cacagagttc tgaatcattt gccaaattca agccccaatt tttatttcca ttttgactga 480
gagcaagatg ttccttttag gggatggaag cgtctgggtt tcccacactg aatgactcaa 540
ctcgaatgtt gcctcattaa cattctcgat ttttccgtaa tctctgctcc atgcattcaa 600
gataactgtg cctatcacaa atggcttttt agcagctcca ctctttctgg ggatgtggtg 660
gcccttccag tagctgccac cacggattgt cttcaatttc tcacttgttt ttgagttgag 720
tgtcagcctg accccctgggc atggccgcac atgactcagg caaagtgaga gtttcatcac 780
taaacgtggc tctgtttgct atgtctgttt tccctctaag agcaggttat tcaaatacca 840
tctggctgag gtcaagttgc ctcagagccc acagaatctc tacccaggtc cctgttggat 900
ccctaaaaac tcagtcatgc tgtaatctcc ttctgaaact gtgcaatgcc tgcaggctgt 960
cagcccagct ctctccttct gcttcctgtc ctcctaggac cccatgcctc ctcaaacgtc 1020
cacgtgtttc ttgctcctcc accacggttg ccaagccaaa attcgggtgg gcgggaggac 1080
attttcccaa gtgcctgttt cccttctttt ccttttgaca ccccagataa atcatctttc 1140
ccaatccaac acagccccac tgtgtctttg gggacttcat gacatcaccc aggaatgtat 1200
ccttagaaac aaaaatgcaa aacccagaac accaggagac aattaaagaa attttcactg 1260
gtgaggtcac aagtagtaga gacttcttgt taacgggcag aaactttcac ggacccagca 1320

-continued

```
tgctactgtg gcagttctgc aacaagctga aaatgccttt cccgaccacc caagccagtg   1380
ccacacaaag gccaccttag ggtgtgcaca ggatgtcact aggcgttggc ggaactcagg   1440
aaggagtctg aatttcttcc cgtttcttcc ttcctctctc attccctatc ttagcttctg   1500
tctctctttc ctctctctcg ttcccccccct tcctccctcc cttcctgttg cagggccaca   1560
gatggaccgg gagacctcaa gcatgtcaaa tcaactaact gctctaccac tcaaccacac   1620
cctcgcctgc attgttacta ctactattat tatcttgata caggtctcca cattgagctc   1680
accctcacag tctccacatt gagctcaccc tcacagtctc cacattgagc tcaccctcac   1740
agtctccaca ttgagctcac cctcacagtc tccacattga gctcaccctc acagtctcca   1800
cattgagctc accctgtggc tctggcaaac cttgaattct ctcattcctc ctgcctcagc   1860
ctctggggtc gtggggatta gccaaaccca cttgaggttt tcttcaatca gcaaattctt   1920
agcgttcaat taacacacac tcataactcc agtactttgg aaaccggaac aggagaattt   1980
ctgtgagctg gaggctagct tggactacag tatgagaccc tgtctctaaa taaatacaca   2040
aagaaatctc accaagggcc tccctctctc agcaagctct aactgtggtg ggagttctgg   2100
gttgttccag ttaacgggct cagaactcta ctgcccagca catcagcccc tagacacagg   2160
tggctctcta catgtgaaca tgcagtcaca gaaatgaaat aaagtgaaaa ttttatttct   2220
tcagttgtat agcctcttcc gtgtgggctg tagttactgt cttgaatagg ataggctcag   2280
aatccttggt gctggaacca agagtttgat tccattagac gacagggaat ataatgccca   2340
atagggcatt cctcctcccg gtcactagcg gtgcactttc tccgaatctt tgtcatgttg   2400
aattagaaaa gttagtattt tcctccatcc cttcccctcc tcccctcctc ccctcctccc   2460
ctcctcccct cctccctccg tctccccgcc cctcccctcc ccctctgatc ctccccccatc   2520
tatcaaatcc aagaattcca gtaaaaagag gaaaacaatc gaagtgattt cgttgattgt   2580
cagttccacc aaagcaagac ttgactttag ttccgcgttt cggttcccgg catgcaccac   2640
agccagcgag caccgtggaa ggatgctagc acggtcctcc ccccgccccc actagctgtc   2700
ttcagctccc cagtagaggg caaccgcact ccagattctc aatggagagt gtttacacaa   2760
tcgttgcggg tttgtgtgag cgcgcccgct tccagagaca cttcttcttt ttcttttttc   2820
catttcatcc cagtggcaac gcagagtgcc agatcattca ggccgtttgc agggcaagcc   2880
gtgggagctt ggcaagcaag gccccatttc ctagggaacc cgtgcctggc gcttcaggaa   2940
agcacgggaa cctggcactg tgactctgcg ggtattattt tgcagaactc tttattaaac   3000
gggagtttca agtccagctg gagacgacca ggcagcgcct ttaaccccag agtcacacac   3060
aggtgccttt tcttggggcc agattggggt tgtgtggcag acctgcgacc agcttgacaa   3120
ctcttctgcc aggccacaaa atggtgttgg ctgtaagagg tgacaccagg gacagggaag   3180
atcgctgcta ttctcctgag ctctccaaag acccacacca gtctgtcccc ctttcctcct   3240
gctcttcccc tgtatcgccc cctcaccatc tcccccaacg agactcttgg catctcctcg   3300
gcacaaggat ttgaaaatag atgcttgggg gtgagaagaa gaagagagaa agagagagaa   3360
ggaaggaagg atatatagat gatacagacg catacaggtg acatgtagct aatcattttt   3420
aattaaaaaa taaattaaaa gcaaatcaag gatatatatg atacccttag agcaagtgtc   3480
tcatacacac acaaacacac acacacaata tatatatata tatatatata tatatatata   3540
tatatatata ttatacttgg aacaagtgtc cagaagggct ggggactcta aagtgcttgt   3600
caaagccagg ctcacatcag taatcttatc acctggtaga ctgagacagg aggattttga   3660
tgagttcagg cccagcctga gctgcagaat gtgattctat cccaaaaaag taaaataaaa   3720
```

taaaattcaa aatacacgaa aagagtattt gctgaacaaa caagcctaaa gccctggatc 3780 ccttcccccca tgtcctaaga aaataagttt cttgaagctg gagggatggc tcagaggtta 3840
agagccccag ctgcacttgc ggaacactaa gacccagttc ccagacccca cactgtgggt 3900
cacaactgtc tcaaacgcca gctccggagg atccatgccc tctcctggcc tccaccggca 3960
ccaagaacac atacagtgcc catacattta tgcaagcaag gtattcacgc acataaaact 4020
aaaagaatat ttaataaaga tataacaaaa tagcatgaag cccagctggt acagaggttc 4080
aaactacatc ccaggttcat ccctctgcct ttgctctcag ttggcttggg taggtctctt 4140
ctctgaactg gcgccctgcg ggttccacat tgagaccctc tcatttttaa acctacttct 4200
tctgggcggg gttaattgct gccagggctc aagccaacgc ttcctcttct ccacagcaat 4260
cttccaagtt tcacgagata accaggaact gctaagttca tgtgaacctt agtgaagaac 4320
ctgagtcttc ccatgtgatt ggtgtgtgca tgtgtgcata cacaaatgta tgtgtgtgct 4380
ctatgtgtgc ctatgtatgt gtgcatgcat gtgtgcatat acaaatgcat atatgtctat 4440
gtagtgtgcg tacacaaatg tatgtgtgtg ctcaatgtgt gcctatgtgt gtgtatgcat 4500
gtgtgcgtac acaatgcatg tgtgtggtgt ctgtgtgcct gtgtgtgtat gcatgtatgc 4560
atacacaaat gtatatgtgt ggtgtgtgaa tgtgtgccta tgtatgtgtg tgctgtgtgt 4620
gggtgtggta tgtgtgtgat gtgtggaggg gtgtgtatgt gtggtatgta taggtgatac 4680
gtttggggtg taatatgcgt atgtggtttg tgaaatgtag ttcgtgtgtg tgcatgtgtg 4740
cgtgcgtgcg tgcgtgcgtg cgtgtgtgtg tgtgtgtgtg tgtgtgtgtt ggatatagta 4800
tgtgtgaggt gtgtgtactc accatggcct ccctcacttg gggagtgaa gtcagcagcc 4860 tggaccactc agggacatga gatactcaga cacatcttga tttccacccc tcttttcctg 4920
atcctccttc acgtgtcact ttcccaaaca ctggacaaca gtttgggggc atctgattcc 4980
actaatgaca gggacatcac atgtctccag agggaacacc ttctgtgtca catgtcatct 5040
gagaatgtag cagagtcaca gagaaatgtc acagaaacca aaatgcagag taccaaggta 5100
tagctaggca cagagcagag gggaagccgc tgaatttatt aaaaatgtca gaatcgtaaa 5160
agacagggga cagcggtggg gacattcagg gtccagtagc acacaggcag tccaaacctg 5220
atcactggaa ggtagtaggt aaggaaaggc tgcacacaga ttattcacac agtttataca 5280
tgtacacaga ttattcacat ggtttgtgta tgtgcacaga ttattcacac agtttataca 5340
tgtgtggctt cgtggtaact ttgagcttac tttcaattta aaaggatctc tctcacaagc 5400
tggggccggg aatggctgca gtcaacactc catcacttag tcacactgtg caaacagcac 5460
ctcctgactc atggtgactt gtagtaaaat gaagaggcca catttgcatc caagacagct 5520
catcagtacc tagtgaagaa tctgtccctg agtatttgca tgaatggacc cgggtccagg 5580
gcctggctgg gagtctccag gtgttgcagc cagaatgtca ttgtgttttt tcaggatccc 5640
agaagtttct aaaatacagg ccaagtactc atttgtgtta caaagtatct gactaataga 5700
agtgattagg taacacaaag ccttttaaaa accgagatca cccttgtcat gtccctggcc 5760
tcttagaaca agatccaagc ttttgctggt tgacaagtgg ggccatccag tgcgtctccg 5820
ttcctgctac ttcatctgga agacctctcc cactaacttg cccctgaccc ctcacacctg 5880
ctgtttcctt tccacccgga agtgcttgtc taggctttca tggccatctg actgagcatc 5940
taggcctcag tccagtggtc cctcagctct ctctagtcac tgtactaatg gaaacggcca 6000
ctaactacat tttcaatatg gaagcctcct cctcaggaac ctccaagggc agaagcctcc 6060

-continued

```
agagaaccac tcctgacccc ctggagttct gagtgcttct ggccctctct gtgtctgcag   6120

gactattcac cacttgtgtt gaatggttca gtcctcacct cctctggcat gtgctcagtt   6180

ctcatctcat tggggagtcc ttcccaggtc actcttctct cctgtctttg aagtgttttt   6240

ttccttcatg gtatttctgt ctgggcacac acacagacac acatacacac acatacacac   6300

ccatgcagta tggcagatac atcacctatg tttcagattt ttattctacc atcacccaat   6360

acctgaatcc ccgaaaaagc cttagaaagc caggaatttg tgtatttttg tcagcactcc   6420

accccagcac ctgaagccaa gcctgactta atatttttgg ttttgtttct aga          6473
```

<210> SEQ ID NO 4
<211> LENGTH: 7045
<212> TYPE: DNA
<213> ORGANISM: Cricetulus griseus

<400> SEQUENCE: 4

```
caattgatta tagatggatg atagatagat agatagatag atagatagat agatagatga     60

tggatagaca gatgatggat agttagagga tagataatga ctgaataata agtacataaa    120

tagatgatag agcggggcgt tggtggtgca cgtctttaac cccagcacca gagaggcaga    180

ggcagttgga tctctgtgag tttgaggaca gcctggttac agaatgggtt ccaggacagc    240

caaggctgtc actcagagaa atactgtctc aaataaaaaa agtaagtaaa caaataaata    300

aatgataact agttagaaga tagatgattg aatgataggt agataaatag aagatagata    360

gatagatgat tgatagatga tagacagata gacagacaga cagacagaca gacagcagaa    420

agataatgca cggtgaaaca tggtctgatt tagttagcaa gatcagagaa gccttctttg    480

aaagtgacat ttgagagcat ttcaaacgct gttcatgtca ggcatgccaa tggggagaga    540

agggcttgca gaaagcaggc ccggcaagcc atggggagca agctaggagg cagcattcct    600

tgcatttgcc tctgcctcag ctgcttcctg gagttccccg gtttttatca caacagtaga    660

aataaaacca ggacaatgtt gtttccatgc atacatctgc aagaacttac tccggttcaa    720

tagacagacc aaggcacctg tgtttgctca agaagcacgg agggaggtgt gtgcacctgc    780

tgggtgctgg tgctctggct gtgccagaca gagagcaaga caggaaagtt cctggtggcc    840

tagagcacac agcccagccc aggaagtcat gtctctctct gtctctgtct ctgccccacc    900

cccaccccat ttaggccaga gaacagctgt ggcaagcttt gggtttgggt gagtcattcc    960

tcaagagcca agagccgccc accttgtatg gggtagtttg ttgttgttgt tgttgttatt   1020

atttgtttgt ttgtttgttt ggtaaaggtt tttcaatagg agttggaatt tggcaattca   1080

gctaggctgg ctgagcagcc agctagcccc gggcactcat ccgtctctac ctccccagtt   1140

ctgggatttc gggtacatgc tgccacatcc gactttttttc ccctgctcca gttcttaaga  1200

ccaagtcttc atgtcaaaca cttcaccacc ttagccatct ttctgggtca gaagttagat   1260

cttcaggaag acaaggagtg tatcaggaca tgagcgtgcc ccaactctgc tcagaccttc   1320

tgatagagaa aatgggggga ggggtgtcag aggctgccgg agaaagacaa gtccaggtta   1380

aggaggacga ccctgggctc tgaatccaag ggtgattccc tcaccttgta cacttggcat   1440

tttgggaagg aagcatcaga taaaagcagt gcagacatag tcaggaatat ttacacgtgt   1500

gagtcaacct gggagtgagt ctgtgtacaa ctgaacatga agcaagtttt gaagcttcat   1560

ttccagacta ttcccagggt gcaataactt cctgttttcg ttgcagcctt cccagtctct   1620

gccactgcca tctctacttc agtctggaat ggtgggcaca cagaaaaagt ctatggcaat   1680

cctgcgagaa gacaagtggg cgcctgactt cgggctcctg ttacaagaga ggaatccagg   1740
```

```
agtttatttt gcagctgatt cagtgttgac caagagtcca gctctggggg agtgggaagc   1800
aaccaaagca gagacaggtc ccagcacaat ttttggtttt caagacagca cttctctgtg   1860
gctttgaagg ctatcctaga actgttcttt gtatatcctt ccttgcaact agctcttata   1920
gaccaggctg gtcttgaact cacagagatc catctgcctc tgcctcccaa gtgctgggat   1980
taaaggcgtg cacctcggct gccaccaccc agctacatac ataatttaca ataataaaaa   2040
taaaatactt taaagtgtta tagcagtttg aatgtaattg gccctgtcat ctcataggga   2100
gtggcactat taggaggtat ggctttgttg aaggaaatat gtcactgtga gggtgggctg   2160
tgaggtttcc tatgctcagg gtaccagcca gtgtctcagc tgaggtcctg ttgcctgcaa   2220
gatgtaggac tctcatccct ttctccagca ccatgtctgt ctgcatgcca tcatgttccc   2280
agccatgatg acaatgtact aaaacctctg aaactgccac ccaactaaat gttttccttt   2340
ataagagttg ccatgctcat ggtgtctctt cacagcaata gaaaccctaa ctaagataag   2400
tgtattctcc cctactcccc atgatttaaa atttaggaag gcaggtaggc aggcaggcag   2460
gctggtatag tggttcattc tagcacctga gacctggaat gggaggattg tgagttagtt   2520
ctaggccatt ctggtgccta gaaaccagag ccgggggttg gcccaatgca gagcacttgc   2580
tctacgtatg gcccagcaca ataagtcaat ttcctcacct taaaggcttg acaatttaaa   2640
aacactggtt tttagttagt ccgtgtctgc tccacagatg gagacagcta atcacagatg   2700
catcaggggc cttcctgagt gctaaacatc aaacagcctt ctcccctcct gagcctttgt   2760
gtgcagaatg tgtccatcgc aagaagcaaa cagtcttgct tgcccaccaa cttccttcct   2820
gcatcagaag agctgggtgc aaactgcaag agtagcctca ccttagagat gggtcccatt   2880
gctctacatg ggagcattac cttccaagaa ggcaaaaatg tctcctggtt gagctttttt   2940
tgtcacctgt taaaggcaaa tcaacagaga ggctttgtct cacccactaa catcttggaa   3000
acaaatacca acgaacgctg gggaggatgt ggggaaagca gagccctcat gctctccgag   3060
ggaaaatcac acccactgtg gaacagtgtg gaaacctcaa agactgggat tacaagcagc   3120
acacaagcca gccacgctac tcctggtcac acaccacaaa gacgcttgca cattcacgct   3180
tacgctgcga acactagcaa cgttcccact gcctcctttg agccccgccc cccgcccctg   3240
ccccccgccc cgcccctgtg gtctatgttc ctcttcccta aagtcagctt ccacttctct   3300
gtctccatct tcgccccacc ctccctcctc gctacataat tgtctctatt ccatttctct   3360
gctttgaaac agctttttgc aaagcatcaa atctattgtc ctatgcccca aatcaacctc   3420
cagtttcaca agtgatacag gaaatcgttt tcctaattaa aaatcccccc tttgaccatt   3480
tattcccact cttggaacat cttccccttg aggaaagtta cagaatgagg tggctctcct   3540
cttcctattc gaggtgtttc cttcagactt tgtccgtgtc taatcttttt aactgttggc   3600
caggcctcca ccacggcaca gatgaactgt ggggttcatt tacctgaaac tctatggaag   3660
gatgtttatt tctccttcac tttagcaaat gataaagggc accattcact ctgtctattc   3720
tgcaggggcc attcctttct ctaggccaga tactgagaat tgctcccaga atcaatgtgg   3780
tatacatatt tccccttcaa cattgatagg cattgatcac acacacacac acacacacac   3840
acacacacac acacagtagc acaaatgtat tcccctagcc cgcttccatc ttgccacagg   3900
actccagagt ggccctggat agcaagcttc ctgttttgtt tctctgttcc tgctgctttt   3960
ccaccctcca gtctatcttt tctaagtcct tctgccattg tcctcttccc aactgtcctg   4020
agatgcagtc attgtctggg attcagacct tctctctctg cccaagtgag tatattgacc   4080
```

-continued cccacggttt gtacaaccat aacttcaggg agcccgacaa aaactgtttt atgagccaag 4140
tagtcccagg acttgagagg tagaggcggg aagatcagca gtttgaggcc agcctggaga 4200
gcataagagc cggtctcaaa acaacaatgg aaactagata ctaagtaaaa atcctggggt 4260
gtttcatcat gaatgtctgt tcttctagta ccacgctgaa ctccgtacac agctccagct 4320
gttacggctt tcttagaatc catactcttt tttttttttt tttttttttt ttttttttgg 4380
tttttcgaga cagggtttct ctgtggcttt ggaggctgtc ctggaactag ctcttataga 4440
ccaggctggt ctcgaactca cagagatcca cctgcctctg cctccagagt gctgggatta 4500
aaggcgtgcg ccaccaacac ccggcagaat ccatactctt tttaaaaaaa gatttatcaa 4560
tttactatgt atacagcttt ctgcctgcat gtatccatgc atgtcagaag atggcaccag 4620
gtcgcattac agatggttgt gagccaccat gtggttgctg ggaattgaac tcagaatgtc 4680
tagaagagca accagttctc ttaacctctg agccatctct ccggccccca gaaatccata 4740
ttcttgagga tttttacac ccccccccacc aaaagacgta tatctaaatt ttaatgtgag 4800
aattcacatt ttcttaagag ttgaacatag atttagagga aaatcagatc ccacatgatt 4860
aacaaagcat gcttgtgggc aggtctgcta ccaagaggtg ggccgtagct tctagctcag 4920
acaaactcac tcccttcctc gtggcctctt cgccctcaag tcagaaactc accctgtgat 4980
tctgccccag aagttgctct agagcacagt gcatccttcc gtcttcactc tgtggcttga 5040
attgtgtcca tcgcttatga ttacaacccc tcacagagca tcctaactgg tttctttgca 5100
tgcctatggg cactcctcca ttctagaaca cccttgccat caatactatg aaaggagggg 5160
tggaggagga agagcaggaa gaggaggggg aagcgaggga agaggaagac acggatggca 5220
atgaggaggg gggagcaccc aagtcctccc tggatgagag tctcactggg agacttaata 5280
ttaattataa atgcttggtc agcagctggg caggataagg ttaggcagga gaaccagact 5340
aaggactctg ggaagcagaa gggcagagtc agacaaggag aggaaacagg aagtacaagg 5400
taaagtcacg tggcagaatg tagataatag aaatgggttc atttaagttg gaagagttag 5460
ctagtaacaa gcctgagcta tcagccgagc atttataatt aatattgagc ctccatattg 5520
gttatctggg aattggcggg cagaaaaaaa aaagtctgcc tacaagtcaa tgtcatgtag 5580
ctcccaaagc caaggtacct ttgttcagtg cttgactgag ccagcattat aaattttctc 5640
cagatgtacc gaatcacatt tcatagcaac atgcagacat caagttttcc ctgaagctct 5700
aaccagctgg ttgcatgctg tccggagtct cagctataac ccagaagtga cctgggtcgg 5760
ggaagaggtg gtactttgcc ttctttgcac tctctgtgtt gcctcaccca ttcagcttca 5820
agcaatgtga ctgcctgacc ctgagggcgt ttacaacgcc tgacccacag accacaagtc 5880
aaccagctgg tgtgctcacg atacctagtc tgaaccatag ccctgctccc accctgcctc 5940
catctccacc ctttcttcac tgctcatcac agctggctag caaagactgc ctcagacctg 6000
agcacaggct ccactccaca gccgtgactg ttcgagccac ttaaatcaaa gagcgcttgt 6060
cttccgctca gtaaatctct cctcagctca ctgatgacgt tgactttctc tagacagcac 6120
atttgggttt aagacactgc tacttgagct cttcattcag ttcctcagaa tacctcattt 6180
gggtcagatt cccaaagagg aagatagggt tcctggcaga cagacatgtc tcattccttt 6240
gaaatccttc agagaaatgc agtgactatg gcaccttctt aaaaagcaca cacacaaata 6300
acacacacac acacacacac acacacacac acacacacac atatcccct cactgtcatc 6360 cttgatatgt atatgatata tataaaatca ttgttttata ctgtgataat tgattatgaa 6420
taaaatttac taaaatgaac aattaaaatt atgggggggg ctggagagat ggctcatcag 6480
ttaagagaac agttgctgct cttgcagaac acgagagttc agttcccagc acccacatca 6540
ggcagctcat aaccatgtgt ggtgtcagtt ccaggagatc tggtgccctc ttctggcctc 6600
ctccagcacc tgctacatgt ggttcacaca cacacacaca cacacacaca cacacacaca 6660
cacacacaca caaataaata taaagattat ttttttcaaa actgagttaa aaataggttc 6720
tatctgattc atactaaggc ttttcacagt ggttaagtct attagatatg tctagccata 6780
tcctttctcc cttctttctt gaggagaggc ttttaaagct acaagttaca gccttctttg 6840
caaataagag taccatttaa caggcctctg accaatgaga tgccagaatc ggttgcccag 6900
gagcttccca aacagtccat tatagggaaa ggtggtacaa accagtagat taggcatgtt 6960
ccacttccta agtgccgtgc caaataagga aatggcctca aatgtttgcc ttttatcttc 7020
acccacctct gaattgcacg ctagt 7045

<210> SEQ ID NO 5
<211> LENGTH: 13515
<212> TYPE: DNA
<213> ORGANISM: Cricetulus griseus

<400> SEQUENCE: 5
tctagaaaca aaaccaaaaa tattaagtca ggcttggctt caggtgctgg ggtggagtgc 60
tgacaaaaat acacaaattc ctggctttct aaggcttttt cggggattca ggtattgggt 120
gatggtagaa taaaaatctg aaacataggt gatgtatctg ccatactgca tgggtgtgta 180
tgtgtgtgta tgtgtgtctg tgtgtgtgcc cagacagaaa taccatgaag gaaaaaaaca 240
cttcaaagac aggagagaag agtgacctgg gaaggactcc ccaatgagat gagaactgag 300
cacatgccag aggaggtgag gactgaacca ttcaacacaa gtggtgaata gtcctgcaga 360
cacagagagg gccagaagca ctcagaactc caggggggtca ggagtggttc tctggaggct 420
tctgcccttg gaggttcctg aggaggaggc ttccatattg aaaatgtagt tagtggccgt 480
ttccattagt acagtgacta gagagagctg agggaccact ggactgaggc ctagatgctc 540
agtcagatgg ccatgaaagc ctagacaagc acttccgggt ggaaaggaaa cagcaggtgt 600
gaggggtcag gggcaagtta gtgggagagg tcttccagat gaagtagcag gaacggagac 660
gcactggatg gccccacttg tcaaccagca aaagcttgga tcttgttcta agaggccagg 720
gacatgacaa gggtgatctc ggtttttaaa aggctttgtg ttacctaatc acttctatta 780
gtcagatact ttgtaacaca aatgagtact tggcctgtat tttagaaact tctgggatcc 840
tgaaaaaaca caatgacatt ctggctgcaa cacctggaga ctcccagcca ggccctggac 900
ccgggtccat tcatgcaaat actcagggac agattcttca ctaggtactg atgagctgtc 960
ttggatgcaa atgtggcctc ttcattttac tacaagtcac catgagtcag gaggtgctgt 1020
ttgcacagtg tgactaagtg atggagtgtt gactgcagcc attcccggcc ccagcttgtg 1080
agagagatcc ttttaaattg aaagtaagct caaagttacc acgaagccac acatgtataa 1140
actgtgtgaa taatctgtgc acatacacaa accatgtgaa taatctgtgt acatgtataa 1200
actgtgtgaa taatctgtgt gcagcctttc cttacctact accttccagt gatcaggttt 1260
ggactgcctg tgtgctactg gaccctgaat gtccccaccg ctgtcccctg tcttttacga 1320
ttctgacatt tttaataaat tcagcggctt cccctctgct ctgtgcctag ctataccttg 1380
gtactctgca ttttggtttc tgtgacattt ctctgtgact ctgctacatt ctcagatgac 1440
atgtgacaca gaaggtgttc cctctggaga catgtgatgt ccctgtcatt agtggaatca 1500

-continued gatgccccca aactgttgtc cagtgtttgg gaaagtgaca cgtgaaggag gatcaggaaa 1560
agaggggtgg aaatcaagat gtgtctgagt atctcatgtc cctgagtggt ccaggctgct 1620
gacttcactc ccccaagtga gggaggccat ggtgagtaca cacacctcac acatactata 1680
tccaacacac acacacacac acacacacac acgcacgcac gcacgcacgc acgcacacat 1740
gcacacacac gaactacatt tcacaaacca catacgcata ttacacccca aacgtatcac 1800
ctatacatac cacacataca cacccctcca cacatcacac acataccaca cccacacaca 1860
gcacacacat acataggcac acattcacac accacacata tacatttgtg tatgcataca 1920
tgcatacaca cacaggcaca cagacaccac acacatgcat tgtgtacgca cacatgcata 1980
cacacacata ggcacacatt gagcacacac atacatttgt gtacgcacac tacatagaca 2040
tatatgcatt tgtatatgca cacatgcatg cacacataca taggcacaca tagagcacac 2100
acatacattt gtgtatgcac acatgcacac accaatcaca tgggaagact caggttcttc 2160
actaaggttc acatgaactt agcagttcct ggttatctcg tgaaacttgg aagattgctg 2220
tggagaagag gaagcgttgg cttgagccct ggcagcaatt aaccccgccc agaagaagta 2280
ggtttaaaaa tgagagggtc tcaatgtgga acccgcaggg cgccagttca gagaagagac 2340
ctacccaagc caactgagag caaaggcaga gggatgaacc tgggatgtag tttgaacctc 2400
tgtaccagct gggcttcatg ctattttgtt atatctttat taaatattct tttagtttta 2460
tgtgcgtgaa taccttgctt gcataaatgt atgggcactg tatgtgttct tggtgccggt 2520
ggaggccagg agagggcatg gatcctccgg agctggcgtt tgagacagtt gtgacccaca 2580
gtgtggggtc tgggaactgg gtcttagtgt tccgcaagtg cagctggggc tcttaacctc 2640
tgagccatcc ctccagcttc aagaaactta ttttcttagg acatggggga agggatccag 2700
ggctttaggc ttgtttgttc agcaaatact cttttcgtgt attttgaatt ttattttatt 2760
ttactttttt gggatagaat cacattctgc agctcaggct gggcctgaac tcatcaaaat 2820
cctcctgtct cagtctacca ggtgataaga ttactgatgt gagcctggct ttgacaagca 2880
ctttagagtc cccagccctt ctggacactt gttccaagta taatatatat atatatatat 2940
atatatatat atatatatat atatattgtg tgtgtgtgtt tgtgtgtgta tgagacactt 3000
gctctaaggg tatcatatat atccttgatt tgcttttaat ttattttta attaaaaatg 3060
attagctaca tgtcacctgt atgcgtctgt atcatctata tatccttcct tccttctctc 3120
tctttctctc ttcttcttct cacccccaag catctatttt caaatccttg tgccgaggag 3180
atgccaagag tctcgttggg ggagatggtg agggggcgat acaggggaag agcaggagga 3240
aagggggaca gactggtgtg ggtctttgga gagctcagga gaatagcagc gatcttccct 3300
gtccctggtg tcacctctta cagccaacac cattttgtgg cctggcagaa gagttgtcaa 3360
gctggtcgca ggtctgccac acaaccccaa tctggcccca agaaaaggca cctgtgtgtg 3420
actctggggt taaaggcgct gcctggtcgt ctccagctgg acttgaaact cccgtttaat 3480
aaagagttct gcaaaataat acccgcagag tcacagtgcc aggttcccgt gctttcctga 3540
agcgccaggc acgggttccc taggaaatgg ggccttgctt gccaagctcc cacggcttgc 3600
cctgcaaacg gcctgaatga tctggcactc tgcgttgcca ctgggatgaa atggaaaaaa 3660
gaaaaagaag aagtgtctct ggaagcgggc gcgctcacac aaacccgcaa cgattgtgta 3720
aacactctcc attgagaatc tggagtgcgg ttgccctcta ctggggagct gaagacagct 3780
agtgggggcg gggggaggac cgtgctagca tccttccacg gtgctcgctg gctgtggtgc 3840
atgccgggaa ccgaaacgcg gaactaaagt caagtcttgc tttggtggaa ctgacaatca 3900

-continued

```
acgaaatcac ttcgattgtt ttcctctttt tactggaatt cttggatttg atagatgggg   3960
gaggatcaga gggggagggg aggggcgggg agacggaggg aggaggggag gaggggagga   4020
ggggaggagg ggaggagggg aagggatgga ggaaaatact aacttttcta attcaacatg   4080
acaaagattc ggagaaagtg caccgctagt gaccgggagg aggaatgccc tattgggcat   4140
tatattccct gtcgtctaat ggaatcaaac tcttggttcc agcaccaagg attctgagcc   4200
tatcctattc aagacagtaa ctacagccca cacggaagag gctatacaac tgaagaaata   4260
aaattttcac tttatttcat ttctgtgact gcatgttcac atgtagagag ccacctgtgt   4320
ctaggggctg atgtgctggg cagtagagtt ctgagcccgt taactggaac aacccagaac   4380
tcccaccaca gttagagctt gctgagagag ggaggccctt ggtgagattt ctttgtgtat   4440
ttatttagag acagggtctc atactgtagt ccaagctagc ctccagctca cagaaattct   4500
cctgttccgg tttccaaagt actggagtta tgagtgtgtg ttaattgaac gctaagaatt   4560
tgctgattga agaaaacctc aagtgggttt ggctaatccc cacgacccca gaggctgagg   4620
caggaggaat gagagaattc aaggtttgcc agagccacag ggtgagctca atgtggagac   4680
tgtgagggtg agctcaatgt ggagactgtg agggtgagct caatgtggag actgtgaggg   4740
tgagctcaat gtggagactg tgagggtgag ctcaatgtgg agactgtgag ggtgagctca   4800
atgtggagac ctgtatcaag ataataatag tagtagtaac aatgcaggcg agggtgtggt   4860
tgagtggtag agcagttagt tgatttgaca tgcttgaggt ctcccggtcc atctgtggcc   4920
ctgcaacagg aagggaggga ggaagggggg gaacgagaga gaggaaagag agacagaagc   4980
taagataggg aatgagagag gaaggaagaa acgggaagaa attcagactc cttcctgagt   5040
tccgccaacg cctagtgaca tcctgtgcac accctaaggt ggcctttgtg tggcactggc   5100
ttgggtggtc gggaaaggca ttttcagctt gttgcagaac tgccacagta gcatgctggg   5160
tccgtgaaag tttctgcccg ttaacaagaa gtctctacta cttgtgacct caccagtgaa   5220
aatttcttta attgtctcct ggtgttctgg gttttgcatt tttgtttcta aggatacatt   5280
cctgggtgat gtcatgaagt ccccaaagac acagtggggc tgtgttggat tgggaaagat   5340
gatttatctg gggtgtcaaa aggaaaagaa gggaaacagg cacttgggaa aatgtcctcc   5400
cgcccacccg aattttggct tggcaaccgt ggtggaggag caagaaacac gtggacgttt   5460
gaggaggcat ggggtcctag gaggacagga agcagaagga gagagctggg ctgacagcct   5520
gcaggcattg cacagtttca gaaggagatt acagcatgac tgagttttta gggatccaac   5580
agggacctgg gtagagattc tgtgggctct gaggcaactt gacctcagcc agatggtatt   5640
tgaataacct gctcttagag ggaaaacaga catagcaaac agagccacgt ttagtgatga   5700
aactctcact ttgcctgagt catgtgcggc catgcccagg ggtcaggctg acactcaact   5760
caaaaacaag tgagaaattg aagacaatcc gtggtggcag ctactggaag ggccaccaca   5820
tccccagaaa gagtggagct gctaaaaagc catttgtgat aggcacagtt atcttgaatg   5880
catggagcag agattacgga aaaatcgaga atgttaatga ggcaacattc gagttgagtc   5940
attcagtgtg ggaaacccag acgcttccat cccctaaaag gaacatcttg ctctcagtca   6000
aaatggaaat aaaaattggg gcttgaattt ggcaaatgat tcagaactct gtgtaggtat   6060
tttcacacgc acagtggata attttcatgt tggagtttat ttgtgctaaa aggcagaaaa   6120
gggtaaaaag cacatcttaa gagttatgag gttctacgaa taaaaataat gttacttaca   6180
gctattcctt aattagtacc cccttccacc tgtggtaatt tcctgagata gtcagtgggg   6240
```

```
aaaagatctc tccttctctt ctttctcccc ctcccctcct ctccctccct ccctccctcc   6300
ctccctcctc tccctccctc cccctttcct tctttctttg ctccttctcc tctgcctcct   6360
tctccctttc ttcttcattt attctaagta gcttttaaca gcacaccaat tacctgtgta   6420
taacgggaaa acacaggctc aagcagctta gagaagattg atctgtgttc actagcgtgc   6480
aattcagagg tgggtgaaga taaaaggcaa acatttgagg ccatttcctt atttggcacg   6540
gcacttagga agtggaacat gcctaatcta ctggtttgta ccacctttcc ctataatgga   6600
ctgtttggga agctcctggg caaccgattc tggcatctca ttggtcagag gcctgttaaa   6660
tggtactctt atttgcaaag aaggctgtaa cttgtagctt taaaagcctc tcctcaagaa   6720
agaagggaga aaggatatgg ctagacatat ctaatagact taaccactgt gaaaagcctt   6780
agtatgaatc agatagaacc tatttttaac tcagttttga aaaaaataat ctttatattt   6840
atttgtgtgt gtgtgtgtgt gtgtgtgtgt gtgtgtgtgt gtgtgtgtgt gaaccacatg   6900
tagcaggtgc tggaggaggc cagaagaggg caccagatct cctggaactg acaccacaca   6960
tggttatgag ctgcctgatg tgggtgctgg gaactgaact ctcgtgttct gcaagagcag   7020
caactgttct cttaactgat gagccatctc tccagccccc cccataattt taattgttca   7080
ttttagtaaa ttttattcat aatcaattat cacagtataa aacaatgatt ttatatatat   7140
catatacata tcaaggatga cagtgagggg gatatgtgtg tgtgtgtgtg tgtgtgtgtg   7200
tgtgtgtgtg tgtgttattt gtgtgtgtgc tttttaagaa ggtgccatag tcactgcatt   7260
tctctgaagg atttcaaagg aatgagacat gtctgtctgc caggaaccct atcttcctct   7320
ttgggaatct gacccaaatg aggtattctg aggaactgaa tgaagagctc aagtagcagt   7380
gtcttaaacc caaatgtgct gtctagagaa agtcaacgtc atcagtgagc tgaggagaga   7440
tttactgagc ggaagacaag cgctctttga tttaagtggc tcgaacagtc acggctgtgg   7500
agtggagcct gtgctcaggt ctgaggcagt ctttgctagc cagctgtgat gagcagtgaa   7560
gaaagggtgg agatggaggc agggtgggag cagggctatg gttcagacta ggtatcgtga   7620
gcacaccagc tggttgactt gtggtctgtg ggtcaggcgt tgtaaacgcc ctcagggtca   7680
ggcagtcaca ttgcttgaag ctgaatgggt gaggcaacac agagagtgca aagaaggcaa   7740
agtaccacct cttccccgac ccaggtcact tctgggttat agctgagact ccggacagca   7800
tgcaaccagc tggttagagc ttcagggaaa acttgatgtc tgcatgttgc tatgaaatgt   7860
gattcggtac atctggagaa aatttataat gctggctcag tcaagcactg aacaaaggta   7920
ccttggcttt gggagctaca tgacattgac ttgtaggcag actttttttt ttctgcccgc   7980
caattcccag ataaccaata tggaggctca atattaatta taaatgctcg gctgatagct   8040
caggcttgtt actagctaac tcttccaact taaatgaacc catttctatt atctacattc   8100
tgccacgtga ctttaccttg tacttcctgt ttcctctcct tgtctgactc tgcccttctg   8160
cttcccagag tccttagtct ggttctcctg cctaacctta tcctgcccag ctgctgacca   8220
agcatttata attaatatta agtctcccag tgagactctc atccagggag gacttgggtg   8280
ctccccccctc ctcattgcca tccgtgtctt cctcttccct cgcttccccc tcctcttcct   8340
gctcttcctc ctccacccct cctttcatag tattgatggc aagggtgttc tagaatggag   8400
gagtgcccat aggcatgcaa agaaaccagt taggatgctc tgtgaggggt tgtaatcata   8460
agcgatggac acaattcaag ccacagagtg aagacggaag gatgcactgt gctctagagc   8520
aacttctggg gcagaatcac agggtgagtt tctgacttga gggcgaagag gccacgagga   8580
agggagtgag tttgtctgag ctagaagcta cggcccacct cttggtagca gacctgccca   8640
```

-continued

```
caagcatgct ttgttaatca tgtgggatct gattttcctc taaatctatg ttcaactctt   8700
aagaaaatgt gaattctcac attaaaattt agatatacgt cttttggtgg ggggggtgta   8760
aaaaatcctc aagaatatgg atttctgggg gccggagaga tggctcagag gttaagagaa   8820
ctggttgctc ttctagacat tctgagttca attcccagca accacatggt ggctcacaac   8880
catctgtaat gcgacctggt gccatcttct gacatgcatg gatacatgca ggcagaaagc   8940
tgtatacata gtaaattgat aaatcttttt ttaaaaagag tatggattct gccgggtgtt   9000
ggtggcgcac gcctttaatc ccagcactct ggaggcagag gcaggtggat ctctgtgagt   9060
tcgagaccag cctggtctat aagagctagt tccaggacag cctccaaagc cacagagaaa   9120
ccctgtctcg aaaaaccaaa aaaaaaaaaa aaaaaaaaaa aaaaaaaaga gtatggattc   9180
taagaaagcc gtaacagctg gagctgtgta cggagttcag cgtggtacta gaagaacaga   9240
cattcatgat gaaacacccc aggattttta cttagtatct agtttccatt gttgttttga   9300
gaccggctct tatgctctcc aggctggcct caaactgctg atcttcccgc ctctacctct   9360
caagtcctgg gactacttgg ctcataaaac agtttttgtc gggctccctg aagttatggt   9420
tgtacaaacc gtgggggtca atatactcac ttgggcagag agagaaggtc tgaatcccag   9480
acaatgactg catctcagga cagttgggaa gaggacaatg gcagaaggac ttagaaaaga   9540
tagactggag ggtggaaaag cagcaggaac agagaaacaa aacaggaagc ttgctatcca   9600
gggccactct ggagtcctgt ggcaagatgg aagcgggcta ggggaataca tttgtgctac   9660
tgtgtgtgtg tgtgtgtgtg tgtgtgtgtg tgtgtgtgat caatgcctat caatgttgaa   9720
ggggaaatat gtataccaca ttgattctgg gagcaattct cagtatctgg cctagagaaa   9780
ggaatggccc ctgcagaata gacagagtga atggtgccct ttatcatttg ctaaagtgaa   9840
ggagaaataa acatccttcc atagagtttc aggtaaatga accccacagt tcatctgtgc   9900
cgtggtggag gcctggccaa cagttaaaaa gattagacac ggacaaagtc tgaaggaaac   9960
acctcgaata ggaagaggag agccacctca ttctgtaact ttcctcaagg ggaagatgtt  10020
ccaagagtgg gaataaatgg tcaaaggggg gatttttaat taggaaaacg atttcctgta  10080
tcacttgtga aactggaggt tgatttgggg cataggacaa tagatttgat gctttgcaaa  10140
aagctgtttc aaagcagaga aatggaatag agacaattat gtagcgagga gggagggtgg  10200
ggcgaagatg gagacagaga agtggaagct gactttaggg aagaggaaca tagaccacag  10260
gggcggggcg gggggcaggg gcggggggcg gggctcaaag gaggcagtgg gaacgttgct  10320
agtgttcgca gcgtaagcgt gaatgtgcaa gcgtctttgt ggtgtgtgac caggagtagc  10380
gtggctggct tgtgtgctgc ttgtaatccc agtctttgag gtttccacac tgttccacag  10440
tgggtgtgat tttccctcgg agagcatgag ggctctgctt tccccacatc ctccccagcg  10500
ttcgttggta tttgtttcca agatgttagt gggtgagaca aagcctctct gttgatttgc  10560
ctttaacagg tgacaaaaaa agctcaacca ggagacattt ttgccttctt ggaaggtaat  10620
gctcccatgt agagcaatgg gacccatctc taaggtgagg ctactcttgc agtttgcacc  10680
cagctcttct gatgcaggaa ggaagttggt gggcaagcaa gactgtttgc ttcttgcgat  10740
ggacacattc tgcacacaaa ggctcaggag gggagaaggc tgtttgatgt ttagcactca  10800
ggaaggcccc tgatgcatct gtgattagct gtctccatct gtggagcaga cacggactaa  10860
ctaaaaacca gtgtttttaa attgtcaagc ctttaaggtg aggaaattga cttattgtgc  10920
tgggccatac gtagagcaag tgctctgcat tgggccaacc cccggctctg gtttctaggc  10980
```

```
accagaatgg cctagaacta actcacaatc ctcccattcc aggtctcagg tgctagaatg  11040
aaccactata ccagcctgcc tgcctgccta cctgccttcc taaattttaa atcatgggga  11100
gtaggggaga atacacttat cttagttagg gtttctattg ctgtgaagag acaccatgag  11160
catggcaact cttataaagg aaaacattta gttgggtggc agtttcagag gttttagtac  11220
attgtcatca tggctgggaa catgatggca tgcagacaga catggtgctg gagaaaggga  11280
tgagagtcct acatcttgca ggcaacagga cctcagctga gacactggct ggtaccctga  11340
gcataggaaa cctcacagcc caccctcaca gtgacatatt tccttcaaca aagccatacc  11400
tcctaatagt gccactccct atgagatgac agggccaatt acattcaaac tgctataaca  11460
ctttaaagta ttttattttt attattgtaa attatgtatg tagctgggtg gtggcagccg  11520
aggtgcacgc ctttaatccc agcacttggg aggcagaggc agatggatct ctgtgagttc  11580
aagaccagcc tggtctataa gagctagttg caaggaagga tatacaaaga acagttctag  11640
gatagccttc aaagccacag agaagtgctg tcttgaaaac caaaaattgt gctgggacct  11700
gtctctgctt tggttgcttc ccactccccc agagctggac tcttggtcaa cactgaatca  11760
gctgcaaaat aaactcctgg attcctctct tgtaacagga gcccgaagtc aggcgcccac  11820
ttgtcttctc gcaggattgc catagacttt ttctgtgtgc ccaccattcc agactgaagt  11880
agagatggca gtggcagaga ctgggaaggc tgcaacgaaa acaggaagtt attgcaccct  11940
gggaatagtc tggaaatgaa gcttcaaaac ttgcttcatg ttcagttgta cacagactca  12000
ctcccaggtt gactcacacg tgtaaatatt cctgactatg tctgcactgc ttttatctga  12060
tgcttccttc ccaaaatgcc aagtgtacaa ggtgagggaa tcacccttgg attcagagcc  12120
cagggtcgtc ctccttaacc tggacttgtc tttctccggc agcctctgac acccctcccc  12180
ccattttctc tatcagaagg tctgagcaga gttggggcac gctcatgtcc tgatacactc  12240
cttgtcttcc tgaagatcta acttctgacc cagaaagatg gctaaggtgg tgaagtgttt  12300
gacatgaaga cttggtctta agaactggag caggggaaaa aagtcggatg tggcagcatg  12360
tacccgaaat cccagaactg gggaggtaga gacggatgag tgcccggggc tagctggctg  12420
ctcagccagc ctagctgaat tgccaaattc caactcctat tgaaaaacct ttaccaaaca  12480
aacaaacaaa caaataataa caacaacaac aacaacaaac taccccatac aaggtgggcg  12540
gctcttggct cttgaggaat gactcaccca aacccaaagc ttgccacagc tgttctctgg  12600
cctaaatggg gtgggggtgg ggcagagaca gagacagaga gagacatgac ttcctgggct  12660
gggctgtgtg ctctaggcca ccaggaactt tcctgtcttg ctctctgtct ggcacagcca  12720
gagcaccagc acccagcagg tgcacacacc tccctccgtg cttcttgagc aaacacaggt  12780
gccttggtct gtctattgaa ccggagtaag ttcttgcaga tgtatgcatg gaaacaacat  12840
tgtcctggtt ttatttctac tgttgtgata aaaaccgggg aactccagga agcagctgag  12900
gcagaggcaa atgcaaggaa tgctgcctcc tagcttgctc cccatggctt gccgggcctg  12960
ctttctgcaa gcccttctct ccccattggc atgcctgaca tgaacagcgt ttgaaatgct  13020
ctcaaatgtc actttcaaag aaggcttctc tgatcttgct aactaaatca gaccatgttt  13080
caccgtgcat tatctttctg ctgtctgtct gtctgtctgt ctgtctatct gtctatcatc  13140
tatcaatcat ctatctatct atcttctatt tatctaccta tcattcaatc atctatcttc  13200
taactagtta tcatttattt atttgtttac ttactttttt tatttgagac agtatttctc  13260
tgagtgacag ccttggctgt cctggaaccc attctgtaac caggctgtcc tcaaactcac  13320
agagatccaa ctgcctctgc ctctctggtg ctggggttaa agacgtgcac caccaacgcc  13380
```

ccgctctatc atctatttat gtacttatta ttcagtcatt atctatcctc taactatcca 13440
tcatctgtct atccatcatc tatctatcta tctatctatc tatctatcta tctatcatcc 13500
atctataatc aattg 13515

<210> SEQ ID NO 6
<211> LENGTH: 14553
<212> TYPE: DNA
<213> ORGANISM: Mus musculus

<400> SEQUENCE: 6
cttgaagaac acatgttttc caagagggag cacccatgtt ggaatgacaa tgtagttagt 60
gctcctctcc tgtaggttag tgctcctttg ctataggtaa gtgctcctct cctataggtc 120
agtgctcctc tcctataggt tagtgctcct ctcctatagg ttagtgctcc tctcctacag 180
gttagtgctc ctctgctcta ggttagtcct gctctcctat agtacctaga gagctagggc 240
aaatgggcta ggcccgaagt gcagagacaa acagctatgg aagactgggt aagcacttcc 300
aagctacgaa agagcagtgt gaagggtcag ggcttgtgca gttagtaggg gagatcttcc 360
agttgaagaa acagaagaac tgagagccac tgggtatcat cctcctgcgc catgccttcc 420
tggatactgc catgctccca ccttgatgat aatggaatga acctctgaac ctgtaagcca 480
gccccaatga aatattgttt ttatgagagt tgccttggtc atgctgtctg ttcacagcag 540
taaaacccta aataaggcag aagttggtac cagtattgct gtgatagacc tgaccatgct 600
ttcctttgaa agaatgtgga tttggtgact ttggatttgc aacacagtgg aatgctttaa 660
atggagatta atgggtcatc aattcctagt aggaatatgg aagactttgt tgctgggagt 720
atttgaactg tgttgacctg gcctaagaga tttcaaagga gaagaatttc agaatgtggc 780
ataaagacag tttttgtggt attttggtga agaatgtggc tactttttgc ccttgtctga 840
aaagtctgcc tgagactaaa gtgaagagaa tcagattaat tgcattgaca agggaagttt 900
gtggctgcgc tatctggaaa cttacagcca gcctcttgga cctcgggtga cttacgcaaa 960
tactcaggga cagagatgct tgactctgta ctgatgagtt gtcttggatg caaatatggg 1020
ctcttcattt gactacatgt cacgatgagt caggagctgc tctctccaga gtgtgacaaa 1080
gcgaggggat gctgacggta gctgttctag ctttgaaggt aagcctgcac ttatgctaaa 1140
gtcacacata cacgagccgg gtggagaacc tgtctgtgtg gagacacctt tcattacctg 1200
tggcatccag cctctcaagc ttggactgcc tgtgtgctcc tggactctgg aggtcccact 1260
gctctgtcct ctgctgctta tgatactgac attttaaaag aatccagtgg ttcccccctg 1320
tactcggtgt ctacttctac ctggatgttc ctcatttatg ttctgtgaca cttctctgtg 1380
actctgctgc attcctgggt gacatgtgga caccctgtcc ctttgcagac catgatgtca 1440
ctgtcactag tggaatcaga tgccccaagt gttgtcctgt gtttgggaac gtgacaggca 1500
gtacagaagc agaagaggaa gggtgaaaac ggaaatgtca cagcagcatc tgatgtgtgc 1560
ctcagtcacg catgctgctg attggaacta ctcagcatga gagagggcca tggtgaatac 1620
acaaccctat acacactgtg tccatttctc tctctctctt acacagagag agagggagga 1680
gggggagggg gaggcggagg gggaggggga gggagaggga gtgggagagg gagagggaga 1740
gggagaggga gagggagagg gagagggaga gggagagttt aatgtctgtg aagagatacc 1800
atgaccaaag caactcttat aaaggacaac atttaattgg ggctggctta caggttcaga 1860
aattcagtcc attctcacca tggtgggaag catgcaggta gatgtggtgc tggaggaacc 1920

-continued

```
aagagttcta tatcctgatc tgaaggcagc caggagaaga ctgcctcttc tgcacagggc   1980
agagcttgag catagaacat caaagccctt ccccacactt cctccaacaa ggtcatacat   2040
acttcaacaa agacacacct cctaacggtg ccactccctg tggaccaacc atttaaacgc   2100
atgagtctat gagggtcaaa gctcttcaaa ccaccacact catgtacaca cacacacaca   2160
cacacacaca ctctcataca cacacacaca cacactcaca cacacacaca cacacacaca   2220
cacacacaca ccacacacac acacacacac agagttctat tttgcactgt ttcactgtca   2280
caaggttcta cttatctcag acacactgcc aggaattgtg tgggaagact ttcagtttct   2340
ttgggttcac atggacttag cagttcttgg tgatcctgaa agatttctgc agaaagaagc   2400
caaagtgttg agcccaaggc ctggccacac attagtcctg tctagatgaa caggggttta   2460
aaaataaggg ggcatcaagg tgaagccagc aggggctgac ttagagagga gacccaccca   2520
agccaactgc tcgaagtcaa aagcgatgaa tccccatatc cagctgtgcc cggtgctgtc   2580
ttgctacatc tttagtaaat gttcttttag ttgtatgcgt atgaatattt tgcttgcata   2640
tatttgtgta caccataggt gttcctaggg cctatggagg ccagaagagg gcatcagatc   2700
ctttggaact ggaattatag acacttgtta cccatagagt agattgtggg aaatgagcct   2760
ttagtcttcg agagcggcca gtgctcttaa cctttggtcg tttctccagg tctttgagac   2820
tttattttct tggacatcag gacaggatcc agggctttga gcttgtttct tcagccagct   2880
ttcttttcat gtatattaaa ttttatgtta ttttgctttc tttttcccca agacagaatc   2940
acactctata tagctcaggc tgggtttgaa ttcagtttcc ctgtctcagt ctaccgggta   3000
atatgattac agatgtgagt ctgactttgg tatcaaagtc cccagccctt ctggatatgt   3060
gttttaagga tatcagatat atccttgatt tgctttgaat tttcttttta gttacaacat   3120
aattagttcc gtgtcacctg aatatgtgta tgtcacctac atagtcttcc ttcttctctt   3180
cttccctctc ccaccttccc aggtacctgt ctgtcttcat atccttgtgc tgagagtctt   3240
gttgagggag atgatgaccg agacagagcc actggggaag ggagatgggc tagtgcaggt   3300
cttcagagag gagctcgtga atattgtagc ccctttagtc cctggcatgt cctcttgtat   3360
agccaccgcc atgctgtggc ctggcagaag tgaataagtt gtccagctgt tgacaggcct   3420
gccctccaga cccagtctga tcccaagaaa gggcatctgt gtctgtctct gaggccgtaa   3480
gtgctgcctg gttgtctcca gcttgacttg acactccctc cttaataaga gtaccacaga   3540
acagggtctg cagagtccct gggccaggtc cctgtgctgt cctggaatgc caggcgtgaa   3600
tttcctgtga agtaggactt tgctcgccaa gctcccacgg cttgcccttc agatagccag   3660
aattatctgg taccctgcat tgccgttcaa tacgcagagt atcactggaa gcgcgcgcgc   3720
gcacacacac acacacacac acacacacac acacacacac acacgcccac tccatcttta   3780
aaccccaccc cccagcaacg gcggtgtaaa cactctccat caggaagctg aaacgcagtt   3840
gccctctgct ggggagatga aggcagcttg ctgggggcga ggaccgtgct agcaaccttc   3900
cctggtgcac acgggctctg gtgcatgacg ggaacggaaa cgcggaacta aagtcagtcc   3960
tgcttttttt tttttttttt tttttttttt tttttttttt tttttttttt ggcgttggtg   4020
gtggactgag tgacaatcag tgaaatcact taggttgttt ttctcttctt cgttgggttt   4080
gatagacggt gggagagggt cagaggagaa ggggagggat ggggagagag ggaggaggga   4140
ggggcgggag gcgggggcg aggaaaacgt gctaacttct ccaatcctac aagacaaagg   4200
tttggagaaa gccgcactga gtgacccagc agaaggaatc caggaatgtc cgctggaatc   4260
tgactgttga ttccagcgcc atgcagagaa tctaggctgg taggaacatt ctttgtccta   4320
```

-continued tccgacataa taactccaac caacacggaa aagaaaggct atacaagtga agaaatggca 4380
ttttcacttt catgactata caatcacttc caggtagtaa cacgtgtcta gcacagcggt 4440
tctcaacctg gggtcacga tcccccactt ttctgcatat cagacatttt tacgttgtta 4500
ttcataacag tagcaaaatt gcagctatga agtaacaatg aaatgcattt atggtgcgtg 4560
tgtgtgtgtg tggggggta tcaccttaac atttactgta agaaggttga gaatactgct 4620
ccagcagcta gtgtgttgga cttaggttct gggtatatta ttagcaatag ccaaccagaa 4680
tccccaccca ccacagcatt gaggccccat gcagggcttg ctgggagagg cactgataag 4740
acttctttat gtatttattt agagacgaat actcattagg taggccaagc tagcgtcaaa 4800
ctcatggcaa ttctcctcct ccagtttcct aagtactgga ctcaggagtg tgttgccatc 4860
atatacagta aggatttatt gactgaagaa aatctcaagt ggctttggtt aatccctact 4920
acgccagagg ctgaggcagg aggcgcgcaa ggtcaaggct tgcctgggct acatatagag 4980
tgagctcaat tttgacactt ggtgcggtgt tagtagtaat agtaaagatg aaggtgtggc 5040
tcaggtgggg ccggtgattg gacacacttg ggtctcctg gtccatctgc agctgtgcaa 5100
caggaagagc ggagaatgag aggaaagaga gaaaagacag aatgagagag agggaggaag 5160
agagaaaaag gaaaagagag aggaaaggaa aaaggaaaat gaggaaagcg agaaagaaga 5220
aatgagaaag aggaaaggga gaaagaaatg agagagagaa aagaaaagac agaatgcgag 5280
agagggagga agagagaaaa aggaaaagag agaggaaagg aaaaaggaaa atgaggaaag 5340
cgagaaagaa gaaatgagaa agaggaaagg gagaaagaaa tgagagagag aaaagaaaag 5400
acagaatgcg agagagggag gaagagagaa aaaggaaaag agagaggaag ggaaaaagga 5460
aaatgaggaa agcgagaaag aagaaatgag aaagaggaaa gggagaaaga aatgagagag 5520
agaaaagaaa agacagaatg cgagagaggg aggaagagag aaaaaggaaa agagagagga 5580
agggaaaaag gaaaatgagg aaagcgagaa agaagaaatg agaaagagga aagggagaaa 5640
gaaatgagag agagaaaaga aaagacagaa tgcgagagag ggaggaagag agaaaaagga 5700
aaagagagag gaagggaaaa tggaaaatga ggaaagcgag aaagaagaaa tgagaaagag 5760
gaaagggaga aagaaatgag cgagataaaa gacagaattt gagagaggga ggaagaaata 5820
ggaaaagaga ggaaaggatg gagaaaagag agaaagaaag agagatgaaa gagagaaagg 5880
agaaatgaaa tgagagagag agagagacac aaagagccag agagagaaga aaaaagggga 5940
aagagaaaga gaaagaggaa ggctcctctt ggacacatct tcctttatct ttccctgggg 6000
accgccaaag cctggtggca tactgtacat tctgtacact gttcattcaa aacaggctct 6060
gtcttaaaga tggtctgagc ggtcagaaaa gggtattgtt aacttgtttg caaaactgcc 6120
tcaggagagt gctgagtgcg tgaaagttgc tgcccgttaa ggagaagtct ctactacttg 6180
tgatctcacc atcgaaaatt tctttaattg tctcctggtg ttctgggttt tgcagttttg 6240
tttctaagga tacattcttg ggtgatgtca caaagtcccc aaagacacgg tggagctgtg 6300
ttagatgggg aaagacagtc tgctgaggat ttatctggaa ctgtcagaag gaaaagaagg 6360
taaatggggc acttgggaaa gtggcctcta gtttgacttc tggcttagca aaggttgtgg 6420
ggagataagg catacacagt agttagcagg aggcaacagg gtcctgggag gacgcgaggc 6480
agaaggagag gctgggctga cagcatgcaa tcattgcata gtctccaaag gagattgcaa 6540
catggctgag ttttcagagg tcctacagag cccgtggtag agattctgtg ggttctgaga 6600
caacttgact ttagccagat ggtatttgag taatctggga gagagaaaac agctacagca 6660
aacagggcca catttagtga cgaaactctc actttgactg ttgagtcatt tgcagtgggc 6720
cctgaggtca ggctggccct cagctcaaaa acaagcgagg aactgaagca attactcaga 6780
taatccacag ccacagccac tggaaagggc cacatcccca gagacagcac agcaggggtg 6840
ggggtggggc tatgagaaag ttagtgattg tagcagttat ctagaatgtg cggagcagag 6900
gaggttacac aaaaacctag aatgtcattc aatgtgggaa accgagaggc tcccaagccc 6960
taaaaggaac agtttgcttt cagccaaaat ggaaataaaa tttggggctt aaatctggca 7020
aatgattcag accttctgtg taggtgtctt taaatgcaca gcagattgat tttcatgttg 7080
gagtttattt gaactaaaag acagaaatgg tgaaaagcac acctgaagaa attgagatgc 7140
tatgaataaa atcatttact tacagctatc acttaattag tacctccttc caccttgctg 7200
atttattggg ctagtcaagg aagaaaagat cttccctcct ccttctctcc tcctccccct 7260
cctctcctcc tcccctcccc tccttgacct tcctctcctc cttttccctc ctccccctct 7320
tcttctcttc acccccctcct cccctcccct cctctgtact cctccccttt cctcccaatc 7380
tcttttttct ccccccttctt ctctttctcc cccctcctct tccctcctct tcctccctcc 7440
ctccctcctc ctcctcatcc tcctcttcct cttcatcctc ttctccttcc tccctctcct 7500
cctcctcctt ttccagccct acctaccttc cctttcttct tcatttattc aaagtagctt 7560
tgaacagcac tactcggttt agttgtgtat aaaaggaaaa tgcaggtcca agcagcttgg 7620
ggaagattgc tttttgctct ctggaggcag atgatgacag ttcaagatca ttccttttgc 7680
tccatgtcac aggaaggggg acatgccgaa tctaccagtt tgcagccacc tacacaggat 7740
ccaccttcac ttctaaggaa atgtttggga agctacctac caaccacttc tggcatctca 7800
tgggctagag gactcttaaa tggcactctt atttgtttaa taaaggaggt tgtgacgtgt 7860
agttttaaat cccttccaca caacaattgc tactctctga ccaaaaaaga agggagacag 7920
gatacggcta ggtgtctagt agactttacc actttgaaaa gccttaatat aaatcaggta 7980
gatacatctt tttaacttat tcttgtaaag acaaaaacaa aactttattt ttatttgtgt 8040
gtatgcttgt gtgtgtgtgc ctgtgtgtat accacatgtc gctggtgccg gagaacacca 8100
gaagagggga cctgatctcc tggagctaaa gctatccatg gttctgagct gcctgatgtg 8160
ggtgctggga acagaactct ggtcttctgc aagagcaaca agcctcctct taactacgaa 8220
tctcctcccc atccccccaa atacatttaa ttattcattt tagcagcttt atttcgtaac 8280
tacttatcac agcataaaac aaggatttta tatatattac atgcaatcga ggataagagt 8340
tgaggggaga tgcgtgtgct ccttctgggt gtctgtgctt ttgaagaatg taagcagtgc 8400
acaagggacc gaggcgtgcc tgtctgccag gagctgtctt cttcccttgg actctgagct 8460
gagtgcagtg ctccgaagaa gtaaaagacg acctcatgaa gcaatgtctt caacccaaac 8520
atgctgtcca gacaaagtcc agcttcatta gtgctctgag gagagactta ctgagcctca 8580
ggaaagcccc cctcagcatg gcgaaagtcc actttgattg aagtgactcg aaagccatgg 8640
cagtgcggcg gcggccgcgt ggagcttgtg ctcgagtcgg aagcggcatc tttgtcaggc 8700
ggctgtgatt agcacgggga ggcaggactg gagtgaagga agagttgggg gcggggctta 8760
gcgctctggt ctcctaagct gtagtcagcg cctcaagatt tgtaacctgc cttctgcctt 8820
cccagccagg cagtcaagtg gctccaagct gaagactgca aagtgcccct aacctttggg 8880
ttatagcgag gctgaagaca ccgtgctctt tcatgaaagc cggatgtctg aaatccgatt 8940
tgataaatat ggataaaacg tataacgctc gatcaatcga atcgaaggag ctcacgattg 9000
gcaccacggc tttggggaca acagagtact gactcgttgg gaggacttgg atacttcccc 9060

```
tcctcttcca tctcttcccc tttcctcact tcctcctcct tccttctcca ttttctccct   9120
cttcactgtt tcttactatt tttacaaaag attttattta tttatttatt tatttattta   9180
tttatttatt tatttattta tttatttaat gtatgcgagt acactgtagc tgtcttcaga   9240
cacaccagaa gagggcgtca agttccatta gagatggttt cgagccacca tgtggttgct   9300
ggggcctctg gaaggaccgc cagtgctctt aacccctgag ccatttctcc agtacccttc   9360
tcaccgtttc tcttcaatct tcttcctctt ccttctccac tttccttgtc ttcttggttt   9420
cattatcttt ctccctttct tcctcttctc cccttcttcc tcctccactg tagttttcct   9480
tccctactct tttcctgcct ccctcctcct cccctctcat tccccctcct ctttcctcct   9540
tctccctcct cctccttcct tctccctctc ccctctcccc tctcccttct cccttctccc   9600
cctcctcttc ctctttctcc ttctccaccc ctcctgtcac agtatcaatg gcaagggtgt   9660
tctagaatgg aggagtgtcc cctaggcact aacgaaagcc agttaggatg ctctgagacg   9720
ggtacaattc agggagggcc gtggggatgg aagggttgtg ctgcgattca ttctggagca   9780
acccccaggc agaatcatga ggttggttcc ggattcgcag ggcacaattc agaagaggaa   9840
ggtttcagga aggacgagtt tgtctgagat aggagttaca tctgatgtct tggcagcaga   9900
gccactgtac aagcgtgctt tattaaccac gtgggattaa atcttctttt aaatttattt   9960
tcaactctta aggaaacgtg aactttcaca ttcaaattta gacttgcagc tcttatgggg  10020
aaaaaaaggg gatcttaaga atattaagca taggcggctg gagagatggc tcagcggtta  10080
agagcactct ctgctctccc agaggtcctg agttcaattc ctagcaacca cataatagtt  10140
aacaacagtc tttaatgaat tctaatgccc tcttctggtg tgtctgaaga cagttacagt  10200
gtactcatat aaataaaata aagaaattta aaaaaatgaa tattaggcat agattcctgg  10260
atcctaagaa agccatcaga gctggagcca tgtgtgggat cctgcttggt gctggagggg  10320
cagagttcat gcccccgggg tttttactta ttatcacatt ttcatcgttg ttttgaaaca  10380
gggtcttgtg tggtccaggc tggccttgaa ctcatctttc agcctctacc tcacaggttc  10440
tgggattact tggttcctaa aagtatctcc gtcaagctcc ctggtgttat ggctgtgcca  10500
accaggaggg tctatacact cgctcaggta gagggagaag atccgaatct ctgacaggga  10560
ctgctgcctc tcggggcaaa tggagtgaag gacagcggca gaaggattta ggaaagatgg  10620
acgggagagt ggaaatgctg cagaagccag aaaacaaagc aggaagcctg ctgtccagtg  10680
gggctcaaga gcggagggat gcgagggggc tgcgcaggaa catttagcgt ctgcgtctat  10740
gggggtaggg gcggggtgcc agcacctagt cacctgaagg ggaaatgctt gcccagggag  10800
caggtctcag tagctgacct agagaaagga gcggccccta cagaggagac acgggtcact  10860
gtttgttaaa gtgaaggaga aataaatatt ctttcaaaga atcttaggtg agcccagttc  10920
atctgcgctg tggaggcctg gggaacagtt aaaaagaccc tgacacacac ccaaggcaaa  10980
caagcaacac acggctcctt ccgtaagggt ccatgattct ctgaagaatc agccccggaa  11040
tcagccccgg aatcaggtag tccgtaaaca caatgagtgt tttactctgc agaagtccag  11100
cctgctggcg tctcccatta ccaaaataga gggatagtca cgtgagctca ccggctcgat  11160
ttaaggcacg tggttttcca gggtagatga gctttggctt ctggaaccat tatggggcac  11220
gaaggatgga gccaggattt tttttttttt tttttttttc tattagcaat tgatttgctt  11280
gggcttggct ggacttgccc agttcttagg cccagtcttc ttaactgccg atctgaagtc  11340
tgtcatggag tcagcctagc cttctcactt cccttcagct cgaataggaa gaggaggtgc  11400
```

-continued

```
acaccagatg gtctgagagc agggataaat ggtgtgcctt tgtctttcag tatttcgtta  11460
ttttaagtag gaagatgctt ttctgtatta cattgcttgt gaaaccggaa gttgattcgg  11520
ggcacaggac aatggatttg gtgttttgca aggactgttt cagaagagag aggagtggaa  11580
gggtggttag agtgaggagt ggggtgggac gggatggggg aagagaagga agggccagac  11640
aggctaggta gggctgagag gaggcggtgg gaacttcttg agttagcgca gcagtaaact  11700
tggatgtgcg tgtatctttg tgatatatga cccggagccg tgtagctggc tccgatagta  11760
ctgctaatgt cagtgtcggg gggggggggt cccatactgt tccacagggg ctgcacattc  11820
ccatcgagag caggagggct cctctctcca tacatcctcg ccagcattcc ttgttgtttc  11880
tgtgatgaca gggggtggga tgaaatctct ctgttggttt gagagaccgt gaagaagctc  11940
aaccccagga cattttgcag tcttggaagg cagtgcctcc atgtggagcc gtggagccca  12000
tctctgagtc caggtcactc ttgcagttcg cactcagctc ttcagatgca ggagagacgt  12060
tggtgggaaa gcaagattgt ttgcttgttg agatagacac attctccaca caaaggctca  12120
cgtggggcaa aggctgattg acgtacagcg ttcaggaacg cctgtggtag agctatgatt  12180
agctgtctcc atctatgaag cagacaaaga gttataaaaa aaatcaatgt tttcaaattg  12240
tcaaactttt aacccgacag caagcgctct gtccctgggc taatccctag ccctggtttc  12300
ttgagatggg gtcttttgtg cactagactg gcctagaact cacgatctta gtgttccagc  12360
ctcccagctg ctgggatgag ccgctataac cagtctgcct gccttcctaa attttaagtg  12420
atgggaagtg gggagaata cagtttaaag tatgcagatc tgagagcagg aacctggcaa  12480
agccaagggg ccggagttac aggcggctaa catgggtgct gggaactgac ccaggtcctt  12540
gagaggagca gtgtgtactc ttgaccaaac aggtccgtct ctccagtccc cgtagtatta  12600
aaaataggta ctacgggcat ggtggtgcac acctttaatc ccagcactag ggaggcagag  12660
gcaggtggat ttctgagttt gaggccagcc tggtctacaa aatgagttcc aggacagcca  12720
cggctataca gagaaaccct gtcttgaaaa caaaacaaca acaaaatagg tactacaaag  12780
cgatgtaatt gtgctcaaac atgcaaaccg aggggactgt atgcataaga aagagaaaga  12840
cggccacact ggttctatct gggtgacagg aaatcagtat ttttattttt cacattcatt  12900
tttttgttgt tgttgttgac acagtgattt ttctatcaaa aacattattt cttttatagt  12960
tcccctgagg agctgttttt aaagccgtgc tttgaaaaac cattgaagga gcagaggcag  13020
ggagactcct gtgtggcagt cggtgaagca ggccctctgc aggcaggctg gccctggact  13080
tgggagtctc tttccctccc tcctgtgctc aaatagcaaa tgtcaggctt caatgtagct  13140
agaaggttct agaatgatta agtttccaag gctgaagagc ttccctgttt gcctttcact  13200
tccctggaga ggtcgttgtg tgttccggag tctgcaaggt gcctttggtg atgcgggtgg  13260
ttcatctcgg gagattccgc ctggaggacc caagttcaag ccctgcctga gctacagagt  13320
gactttcagg tcttctgcgc aattcagtga gacccagtct acaaataaaa agtaaaaaga  13380
aggctgtgga tggaactcgg tggtagagtt ctgggtttac tccctagagg aggggagaag  13440
gaggaggagg gaggaggaag aggaagaaag aagaagagaa gggaagagga gaaggaaggg  13500
agggaagggg ctgacaagaa gagagaagag ggagggaggg gagggaaagg aaggggaaag  13560
gaagggaggg aaggggctga caagaagaga gaagagggag ggaggggagg gaaaggaagg  13620
ggaaagaaga gaagggtaag aagaaactgt tccaatggtc tgggccacag agtgatggcc  13680
ttttgtggtg atcagctgta atccttgatt tgacacaacc tagaatctgg gaagcgagtt  13740
tctgtgaagg agcattcaca ctggctggcc tgtgggcgtg catgtgggag actgtcataa  13800
```

ttaggttcat taatacagga agtcccagcc cactacaaat ggcttcgttc catacccaag 13860
agatgctaac tgtagacggt tggagaaagc aagcaagctg tggatacccc acgctctttc 13920
acctcggctc ctggggggtg ggtgcactgt gtctcttggt attttaaagt cctgccttga 13980
cgtccctgct gtgacagact gtaactggaa ttgtgagctt tagtccttta gttttctacg 14040
ttggtttttc tcaggatatt ttatcgcagt aacagaaaca agaccaggac acttgatctc 14100
ctctgatcaa cactgaagag ttacaaaaca ggctgaggaa acaaactttc ttctccctct 14160 ccccccttctg tccctcccct tccttctcgc tccctccctt gccccctctc tccctgtctc 14220
tgtctctgtc tctgtctctg tctctgtctc tgtctctgcc tctcccctcc cctcccctcc 14280
ctctgtctct gtctctgtct ctgtctctgt ctctgtctct gtctctgtcc ctttctcctc 14340
tatctcctaa atggctggag gccatgctag ctcaatgttg aactttgaac acgtatttag 14400
gaaatctttg ttcttaacag ttctgaagtg ctgaagtggt ggtttagtct ctcggcctga 14460
caagctcact tcctctcact ctgtcttaat gaccaaatct gccatttccc taaaacagca 14520
caggctccag ctccaggttg ctccggagcg gag 14553

<210> SEQ ID NO 7
<211> LENGTH: 34
<212> TYPE: DNA
<213> ORGANISM: Artificial sequence
<220> FEATURE:
<223> OTHER INFORMATION: synthetic

<400> SEQUENCE: 7
ataacttcgt ataatgtatg ctatacgaag ttgt 34

<210> SEQ ID NO 8
<211> LENGTH: 34
<212> TYPE: DNA
<213> ORGANISM: Artificial sequence
<220> FEATURE:
<223> OTHER INFORMATION: synthetic

<400> SEQUENCE: 8
ataacttcgt ataatgtata ctatacgaag ttag 34

<210> SEQ ID NO 9
<211> LENGTH: 60
<212> TYPE: DNA
<213> ORGANISM: Artificial sequence
<220> FEATURE:
<223> OTHER INFORMATION: synthetic

<400> SEQUENCE: 9
agattctgtg ggctctgagg caacttgacc tcagccagat ggtatttgaa taacctgctc 60

<210> SEQ ID NO 10
<211> LENGTH: 54
<212> TYPE: DNA
<213> ORGANISM: Rattus norvegicus

<400> SEQUENCE: 10
agattctgtg ggttctgaga caacttgact tcagccagat ggcatttgaa taac 54

<210> SEQ ID NO 11
<211> LENGTH: 59
<212> TYPE: DNA
<213> ORGANISM: Mus musculus

<400> SEQUENCE: 11
agattctgtg ggttctgaga caacttgact ttagccagat ggtatttgag taatctggg 59

<210> SEQ ID NO 12
<211> LENGTH: 59
<212> TYPE: DNA
<213> ORGANISM: Homo sapiens

<400> SEQUENCE: 12
agattcagtg ggctttggga cagcttgact tcaactagat ggtatttgaa taatctgct 59

<210> SEQ ID NO 13
<211> LENGTH: 624
<212> TYPE: DNA
<213> ORGANISM: Artificial sequence
<220> FEATURE:
<223> OTHER INFORMATION: synthetic

<400> SEQUENCE: 13
ttcttgagtt ccgccaacgc ctagtgacat cctgtgcaca ccctaaggtg gcctttgtgt 60
ggcactggct tgggtggtcg ggaaaggcat tttcagcttg ttgcagaact gccacagtag 120
catgctgggt ccgtgaaagt ttctgcccgt taacaagaag tctctactac ttgtgacctc 180
accagtgaaa atttctttaa ttgtctcctg gtgttctggg ttttgcattt ttgtttctta 240
aggatacatt cctgggtgat gtcatgaagt ccccaaagac acagtggggc tgtgttggat 300
tgggaaagat gatttatctg ggtgtcaaa aggaaaagaa gggaaacagg cacttgggaa 360
aatgtcctcc cgcccacccg aattttggct tggcaaccgt ggtggaggag caagaaacac 420
gtggacgttt gaggaggcat ggggtcctag gaggacagga agcagaagga gagagctggg 480
ctgacagcct gcaggcattg cacagtttca gaaggagatt acagcatgac tgagttttta 540
gggatccaac agggacctgg gtagagattc tgtgggctct gaggcaactt gacctcagcc 600
agatggtatt tgaataacct gctc 624

<210> SEQ ID NO 14
<211> LENGTH: 665
<212> TYPE: DNA
<213> ORGANISM: Rattus norvegicus

<400> SEQUENCE: 14
tttatctttc cctggggaca gccaaagcct ggtggcatcc tctgtgaagt gttcattcaa 60
gacaggctct gtcttaaagg tggccttcgc atggcgctgg cactggccgg ggcagtcagg 120
agagggtatt tttagcttct ttgcagaatg gcctcaggag cgtgctgagt ctgtgaaagt 180
tgctgccagt taaggagaag tctctaccac tcgtgacctc accattgaaa atttctttaa 240
ttgtctcctc gtgttctggg ctttgcagtt ttgttcctaa ggatacattc ttgggtgatg 300
tcacgaagtc cccaaagaca cagtggggct gtgttagatc gggacagaca atattgctga 360
ggatttatct gaaggtgtca aaaggagaag aagggaaaca gggcactcag ggaaatggcc 420
tctagtctga gttctggctc agcaacagag gtggggagat aaggcacaca cagtggttag 480
aaggagtcat cagggttctg ggaggacagg aggcaggaga ggcagggctg acagtgtgca 540
atcattgtgt agtctcccaa ggagattaca acatggctga attttcaggg gtccaacgga 600
gactgtagtg gagattctgt gggttctgag acaacttgac ttcagccaga tggcatttga 660
ataac 665

-continued

<210> SEQ ID NO 15
<211> LENGTH: 655
<212> TYPE: DNA
<213> ORGANISM: Mus musculus

<400> SEQUENCE: 15

```
tttatctttc cctggggacc gccaaagcct ggtggcatac tgtacattct gtacactgtt     60

cattcaaaac aggctctgtc ttaaagatgg tctgagcggt cagaaaaggg tattgttaac    120

ttgtttgcaa aactgcctca ggagagtgct gagtgcgtga aagttgctgc ccgttaagga    180

gaagtctcta ctacttgtga tctcaccatc gaaaatttct ttaattgtct cctggtgttc    240

tgggttttgc agttttgttt ctaaggatac attcttgggt gatgtcacaa agtccccaaa    300

gacacggtgg agctgtgtta gatggggaaa gacagtctgc tgaggattta tctggaactg    360

tcagaaggaa aagaaggtaa atggggcact tgggaaagtg gcctctagtt tgacttctgg    420

cttagcaaag gttgtgggga gataaggcat acacagtagt tagcaggagg caacaggtcc    480

tgggaggacg cgaggcagaa ggagaggctg ggctgacagc atgcaatcat tgcatagtct    540

ccaaaggaga ttgcaacatg gctgagtttt cagaggtcct acagagcccg tggtagagat    600

tctgtgggtt ctgagacaac ttgactttag ccagatggta tttgagtaat ctggg         655
```

<210> SEQ ID NO 16
<211> LENGTH: 706
<212> TYPE: DNA
<213> ORGANISM: Homo sapiens

<400> SEQUENCE: 16

```
agaaacacaa cttctcccag ggagagtcaa gagagcagtg tcatttccta taaaatgtcc     60

aaggccaatc ccaggtcccg gtgtcagccc ttgcgtgtgg cactggcacc agcagccaga    120

aaggttactt gtgacttgtt ttcagtgctt tcctgggagt gtcctgaaag ctggcagtgt    180

ttctgcctcg tcagaagagg cctcattcat ttggggttgt accagcaact taaaaagttt    240

tttttttct tccctcttcc agtgttaata gattttgaaa gaggcatttt tgtttctaat    300

tacaaattcc tgggtgatgt cattaagccc tcaaacaccc ggtgagggcg gcactgaatg    360

gggaaagaca atatgctaac aagttatctg agggtgtcag aaagaaatga tgaaaaacag    420

tacagttggg ggaaatgttt tccagcctgc tttctggttt tagcgactgc atgggaagag    480

ataagacaca catggctttt ataaggagcc atcgggatct ctaggggaca tgaggcagga    540

gaaaagaatt gggctgaaag catccaatca tcacatattc acggagaaag agattacaat    600

atagcagagg aagctcttcc agggctccta cagggacctt tggcaaaga ttcagtgggc    660

tttgggacag cttgacttca actagatggt atttgaataa tctgct                   706
```

<210> SEQ ID NO 17
<211> LENGTH: 268
<212> TYPE: DNA
<213> ORGANISM: Artificial sequence
<220> FEATURE:
<223> OTHER INFORMATION: synthetic

<400> SEQUENCE: 17

```
ttagagggaa aacagacata gcaaacagag ccacgtttag tgatgaaact ctcactttgc     60

ctgagtcatg tgcggccatg cccaggggtc aggctgacac tcaactcaaa aacaagtgag    120

aaattgaaga caatccgtgg tggcagctac tggaagggcc accacatccc cagaaagagt    180

ggagctgcta aaaagccatt tgtgataggc acagttatct tgaatgcatg gagcagagat    240
```

-continued

```
tacggaaaaa tcgagaatgt taatgagg                                         268


<210> SEQ ID NO 18
<211> LENGTH: 265
<212> TYPE: DNA
<213> ORGANISM: Rattus norvegicus

<400> SEQUENCE: 18

agctccagca agcacagcca catttaggga tgaaactctc actttgactg tgagtcacgt      60

gtagctgtgt cccgaggtca ggctggccct cagctcaaaa acaagtgagg gattgaagca     120

attactcaga taattcacag ccacagctac ggggagggcc gcatccccag aaacatcggg     180

gttactataa agctagtggt ggtcacagtt atcttgaatg tatggagcag aggagattac     240

agaaaaacct agaatgttaa tgagg                                            265


<210> SEQ ID NO 19
<211> LENGTH: 284
<212> TYPE: DNA
<213> ORGANISM: Mus musculus

<400> SEQUENCE: 19

agagagaaaa cagctacagc aaacagggcc acatttagtg acgaaactct cactttgact      60

gttgagtcat ttgcagtggg ccctgaggtc aggctggccc tcagctcaaa aacaagcgag     120

gaactgaagc aattactcag ataatccaca gccacagcca ctggaaaggg ccacatcccc     180

gagacagcac agcaggggtg ggggtggggc tatgagaaag ttagtgattg tagcagttat     240

ctagaatgtg cggagcagag gaggttacac aaaaacctag aatg                       284


<210> SEQ ID NO 20
<211> LENGTH: 287
<212> TYPE: DNA
<213> ORGANISM: Homo sapiens

<400> SEQUENCE: 20

ggagagaaaa cagatatagc acacactgtc acatttagcg ttgaaactct cggtttgact      60

atgagtaatg ttcagccatg cccaagggtc aggcctacac tcactcagaa acaagtgggg     120

aattgaagca attattcaga taatccatag acatagctac tggccagtgc tgcacccctg     180

atttagccca gaaacagtaa tgctattata agctgttggt gatttgtgga gcaatcttga     240

atttattaag gaaaggagat tatagaaaaa tccagaatgc caatggg                    287
```